(12) United States Patent
Lisy et al.

(10) Patent No.: US 11,950,912 B1
(45) Date of Patent: *Apr. 9, 2024

(54) DRY PHYSIOLOGICAL RECORDING DEVICE AND METHOD OF MANUFACTURING

(71) Applicant: Orbital Research Inc., Cleveland, OH (US)

(72) Inventors: Frederick J Lisy, Euclid, OH (US); Brian M Kolkowski, Leroy, OH (US); Mark Pennington, Medina, OH (US)

(73) Assignee: Orbital Research Inc., Cleveland, OH (US)

( * ) Notice: Subject to any disclaimer, the term of this patent is extended or adjusted under 35 U.S.C. 154(b) by 567 days.

This patent is subject to a terminal disclaimer.

(21) Appl. No.: 17/130,004

(22) Filed: Dec. 22, 2020

Related U.S. Application Data

(63) Continuation of application No. 16/451,815, filed on Jun. 25, 2019, now Pat. No. 10,898,094, which is a continuation of application No. 14/885,219, filed on Oct. 16, 2015, now Pat. No. 10,376,168, which is a continuation of application No. 13/826,185, filed on Mar. 14, 2013, now Pat. No. 9,192,313.

(51) Int. Cl.
*A61B 5/25* (2021.01)
*A61B 5/00* (2006.01)
*A61B 5/24* (2021.01)
*A61B 5/296* (2021.01)

(52) U.S. Cl.
CPC ............ *A61B 5/25* (2021.01); *A61B 5/24* (2021.01); *A61B 5/296* (2021.01); *A61B 5/6832* (2013.01); *A61B 5/6833* (2013.01); *A61B 5/6839* (2013.01); *A61B 2562/0209* (2013.01)

(58) Field of Classification Search
CPC .. A61B 5/25; A61B 5/296; A61B 5/24; A61B 5/6832; A61B 5/6833; A61B 5/6839; A61B 2562/0209
See application file for complete search history.

(56) References Cited

U.S. PATENT DOCUMENTS

| | | | | |
|---|---|---|---|---|
| 4,685,466 A | * | 8/1987 | Rau | A61B 5/252 600/387 |
| 8,201,330 B1 | * | 6/2012 | Rood | A61B 5/25 29/882 |

(Continued)

*Primary Examiner* — Adam Z Minchella
(74) *Attorney, Agent, or Firm* — Brian Kolkowski

(57) ABSTRACT

The present invention is directed to a physiological recording device and, more particularly, to a physiological recording device that can be used without skin preparation or the use of electrolytic gels. The invention is further directed to an encouragement ring which stabilizes and helps situate the physiological recording device on a subject's skin to help provide a better electrical signal, increase surface area, and reduce and minimize noise and artifacts during the process of recording or monitoring a physiological signal. The invention is still further directed to surface features on a surface of the physiological recording device with a size and shape that will not substantially bend or break, which limits the depth of application of the recording device, and/or anchors the recording device during normal application. The invention is even further directed to a method for manufacturing a physiological recording device, and minimizing cost of manufacture.

20 Claims, 26 Drawing Sheets

(56) References Cited

U.S. PATENT DOCUMENTS

| | | | |
|---|---|---|---|
| 2006/0047194 A1* | 3/2006 | Grigorov | A61B 5/28 600/372 |
| 2008/0114220 A1* | 5/2008 | Banet | A61B 5/316 600/382 |
| 2011/0295100 A1* | 12/2011 | Hegde | A61B 5/291 600/372 |

* cited by examiner

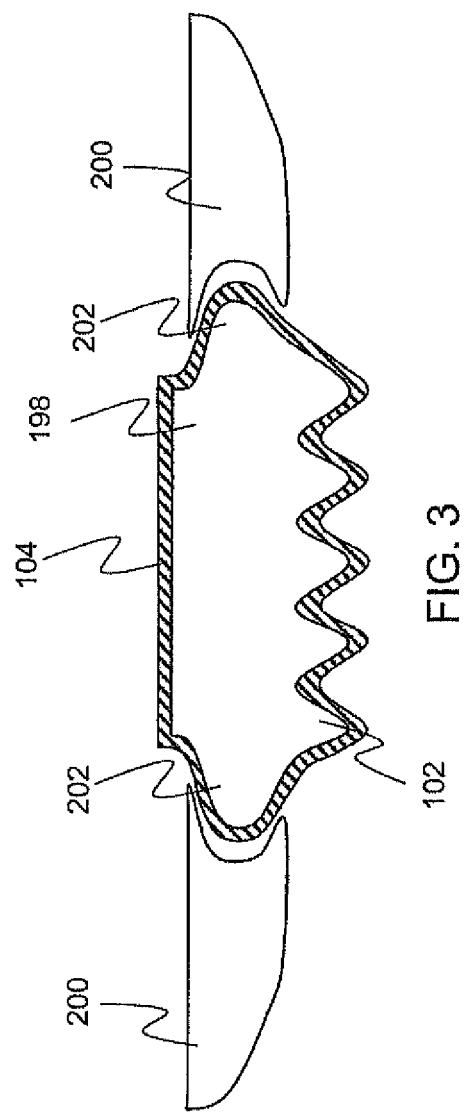

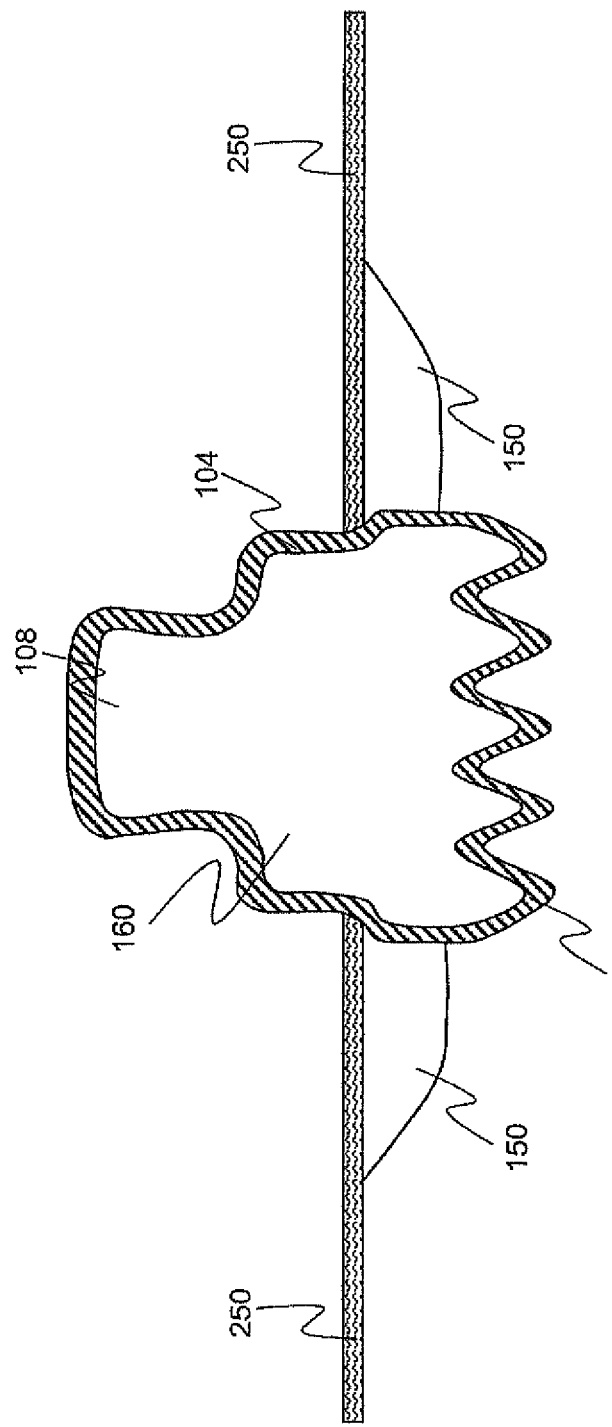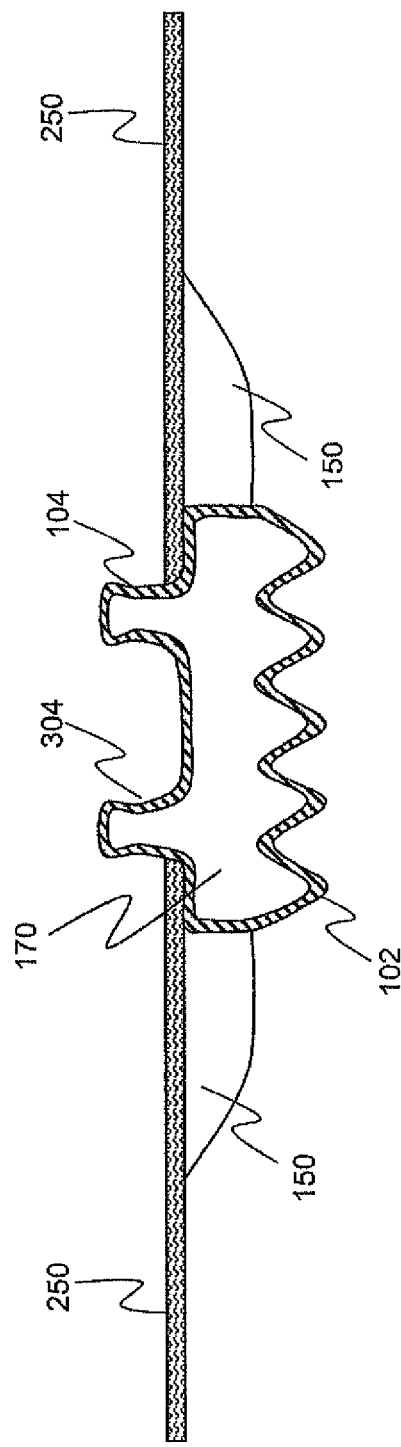

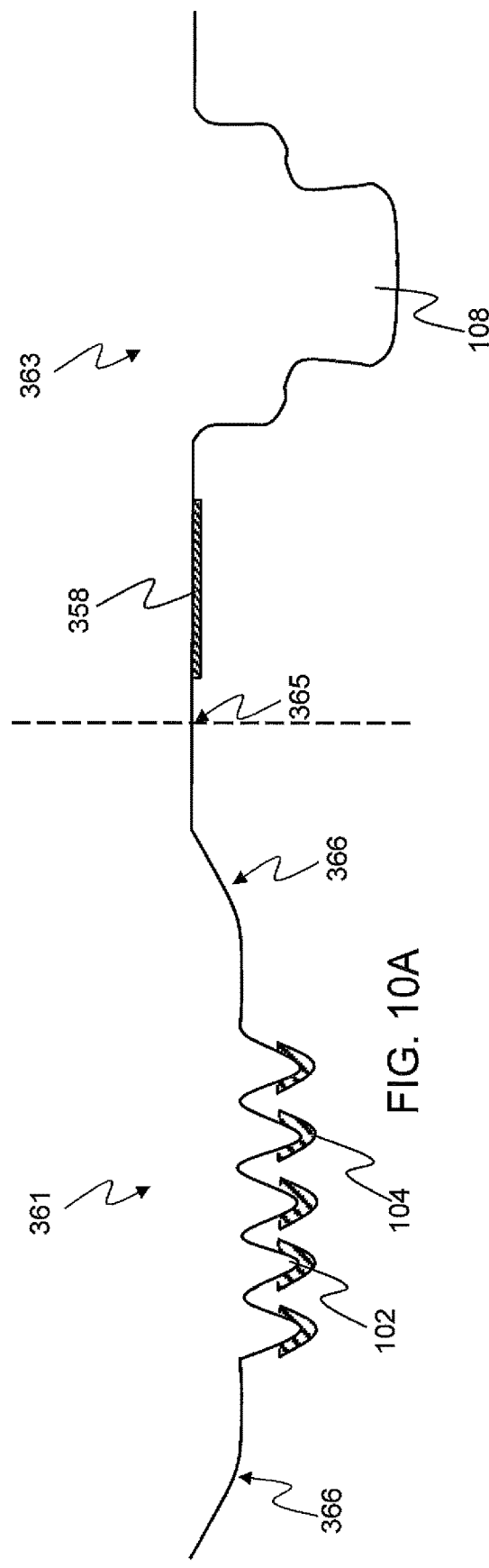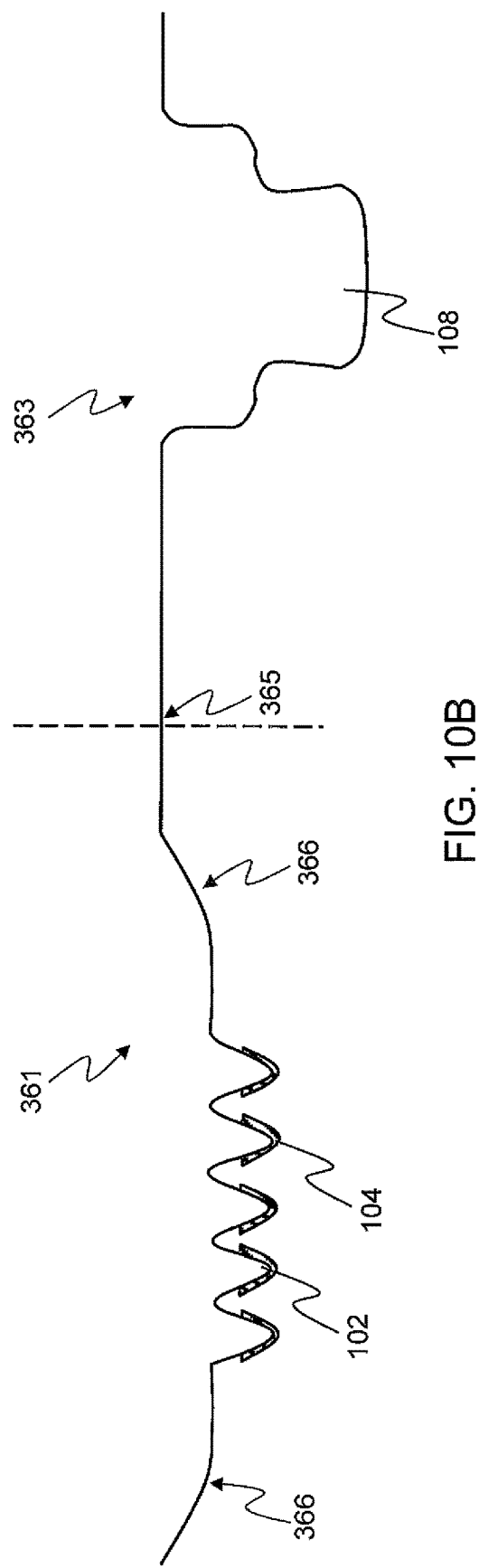

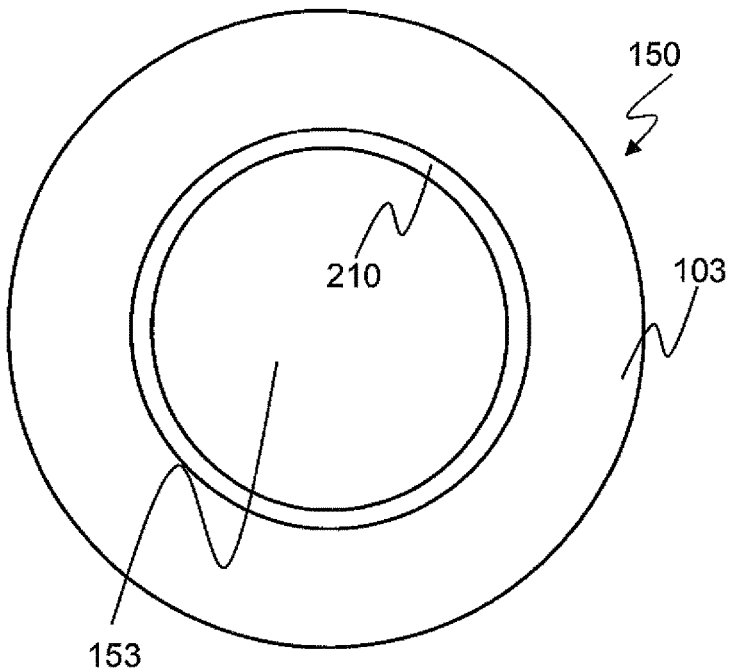
FIG. 20A
FIG. 20B
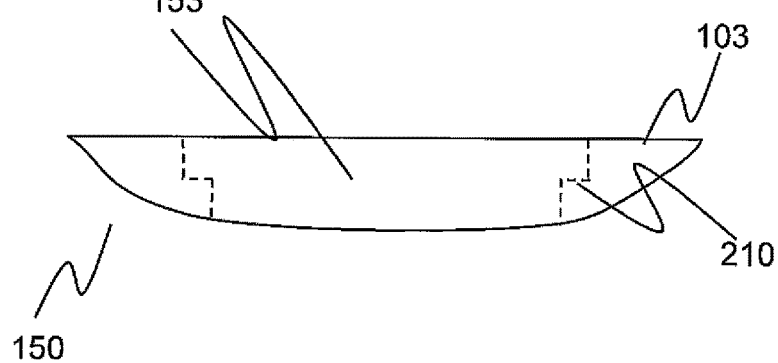
FIG. 20C
FIG. 20D
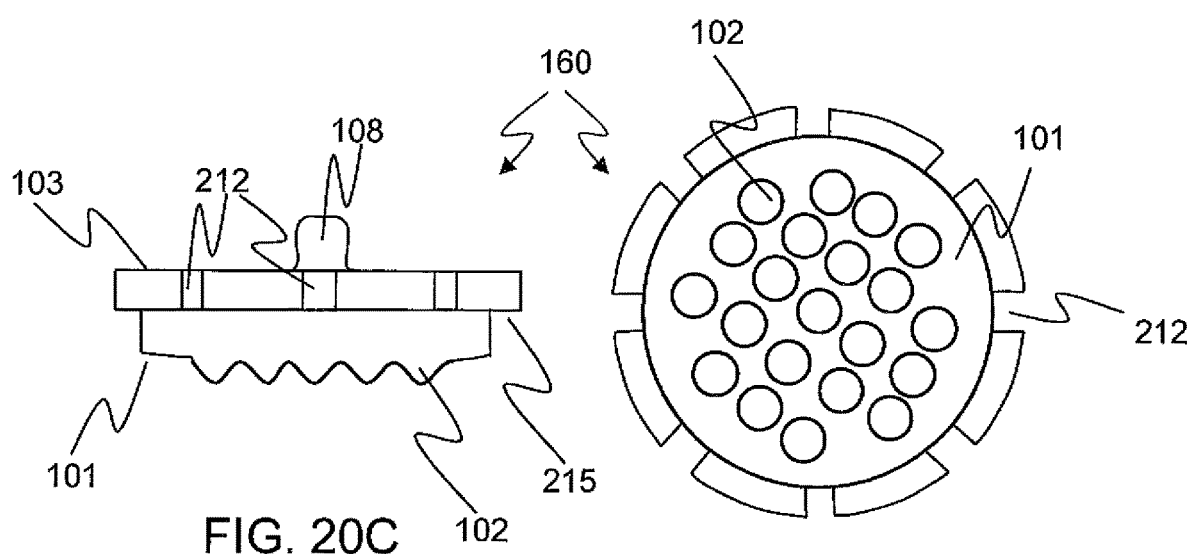

DRY PHYSIOLOGICAL RECORDING DEVICE AND METHOD OF MANUFACTURING

CROSS REFERENCE TO RELATED APPLICATIONS

This application is a continuation of U.S. patent application Ser. No. 16/451,815, which was filed on Jun. 25, 2019 and which is a continuation of U.S. patent application Ser. No. 14/885,219, which was filed on Oct. 16, 2015 and issued as U.S. Pat. No. 10,376,168 on Aug. 13, 2019, which is a continuation of U.S. patent application Ser. No. 13/826,185, which was filed on Mar. 14, 2013 and issued as U.S. Pat. No. 9,192,313 on Nov. 24, 2015.

BACKGROUND OF THE INVENTION

1. Field of the Invention

The present invention is directed to a physiological recording device and, more particularly, to configurations thereof maximizing performance while minimizing material cost, and that can be used without skin preparation or the use of electrolytic gels. The invention is further directed to an encouragement ring which stabilizes and helps situate the physiological recording device on a subject's skin to help provide a better electrical signal, increase surface area, and reduce and minimize noise and artifacts during the process of recording or monitoring a physiological signal. The invention is still further directed to surface features on a surface of the physiological recording device with a size and shape that will not substantially bend or break, which limits the depth of application of the recording device, and/or anchors the recording device during normal application. The invention is even further directed to a method for manufacturing a physiological recording device, and minimizing cost of manufacture.

2. Technical Background

Electrodes for measuring biopotential are used extensively in modern clinical and biomedical applications. These applications encompass numerous physiological signal acquisition and monitoring modalities including electrocardiography (ECG), electroencephalography (EEG), electrical impedance tomography (EIT), electromyography (EMG) and electro-oculography (EOG). The electrodes for these types of physiological tests function as a transducer by transforming the electric potentials or biopotentials within the body into an electric voltage that can be measured by conventional measurement and recording devices. Such electrodes traditionally required preparation of the skin in order to increase the quality of the transmitted/recorded signal. Such preparation may include removing hair, abrading the skin, and/or application of electrolytic fluids or gels. However, more recently, "dry" electrodes, requiring no electrolytic fluids or gels, have been developed which eliminate the need for skin preparation in order to transmit higher quality signals.

Both traditional "wet" electrodes and existing varieties of "dry" electrodes give rise to issues in recording of physiological biopotential signals. Whereas existing varieties of dry electrodes improved over wet electrodes by eliminating the need for messy electrolytic gels, these dry electrodes still suffer from their own shortcomings. Most notably, manufacturing costs of those devices are traditionally very high, making production on a large scale difficult and not very cost effective. These electrodes typically need to be made from expensive polymers which are typically non-conducting. The overall expense of the electrode is increased significantly over the cost of just the base polymer material by the requirement of adding a conductive coating and/or ionic compound to the entire surface of the electrodes in order to ensure an electrical pathway exists whereby the biopotentials may be transferred from the patient or subject to the appropriate monitoring equipment. The most common conductive coating and/or ionic compound used in electrodes, and particularly to coat dry electrodes, is silver/silver chloride (Ag/AgCl), which is preferable due to its high biocompatibility and conductivity properties. This Ag/AgCl coating will not harm the patient, nor generally cause any adverse reactions, while still providing the high conductivity required for transmitting the biopotential across an otherwise non-conductive electrode body. The compound of silver chloride itself is approximately 75.2% silver. Thus, when a combination of silver and silver chloride is used, a large percentage of silver is actually required to coat the entire electrode surface to meet the conductivity requirements for using such electrodes to transmit biopotentials. Typically, dry electrodes are monolithic in nature, that is, constructed in a single piece, and coated about their entirety in a conductive or ionic compound such as Ag/AgCl. Thus, these dry electrodes, while addressing many disadvantages of traditional "wet" electrodes, are expensive to manufacture, and thus present some obstacles in actually being adopted over traditional electrodes in spite of the shortcomings thereof, which are much less expensive.

Therefore, an object of the present invention is to provide a dry electrode that is significantly less expensive to manufacture and produce than prior dry electrodes. It is further an object of the present invention to provide a dry electrode that minimizes the amount of expensive conductive coatings or ionic compounds required to accurately and effectively transmit biopotentials. It is still further an object of the present invention to provide a separate encouragement ring, constructed of a separate and less expensive material, which helps to reduce cost and also provide stability to the device when placed on a subject's skin.

In view of the foregoing inherent disadvantages with presently available wet and dry electrodes, it has become desirable to develop an electrode that does not require skin preparation or the use of electrolytic gels and overcomes the inherent disadvantages of presently available dry electrodes.

SUMMARY OF THE INVENTION

The present invention is directed to a physiological recording device and, more particularly, to configurations thereof maximizing performance while minimizing material cost, and that can be used without skin preparation or the use of electrolytic gels. The invention is further directed to an encouragement ring which stabilizes and helps situate the physiological recording device on a subject's skin to help provide a better electrical signal, increase surface area, and to further reduce and minimize noise and artifacts during the process of recording or monitoring a physiological signal. The invention is still further directed to surface features on a surface of the physiological recording device with a size and shape that will not substantially bend or break, which limits the depth of application of the recording device, and/or anchors the recording device during normal application. The invention is even further directed to a method for manufacturing a physiological recording device, and minimizing cost of manufacture.

The physiological recording device of the present invention can be used in a variety of applications including for measuring various biopotentials including but not limited to ECG, EEG, EMG, and EOG, and for taking other physiological measurements, such as galvanic skin response and temperature, that can be determined from the skin or subcutaneous layers of the subject. The physiological recording device can further be used for any other application wherein ionic potentials are measured. The ionic potentials can be acquired and transmitted via the physiological recording device in similar manners as biopotentials using a "wet" electrode, and thus various measurements and calculations can be obtained and/or performed from those potentials. Further still, the physiological recording device may be used for point to point measurements between electrodes. Examples of these other types of applications may include, but are not limited to blood composition measurements such as glucose or alcohol concentration, or electrical impedance measurements such as electrode impedance, skin impedance, or impedance of fluids in the body.

The physiological recording devices of the present invention are applied to a subject, which can be an animal or human body having skin comprising an epidermis comprising a stratum corneum layer and lower layers of the epidermis, and a dermis. The physiological recording devices of the present invention further preferably comprise at least one surface feature on the lower surface of the device, the surface that comes into contact with the subject's or patient's skin. The surface feature(s) increases the surface contact with the skin and transforms a portion of the ionic current into an electric voltage that can be transmitted through these individual surface feature(s). The surface features further enhance the stability of the device when placed on the subject's or patient's skin, and serve to decrease electrical impedance, thus facilitating transmission of a stronger, higher quality signal.

The physiological recording device of the present invention has an upper and a lower surface. The lower surface of the physiological recording device is preferably the surface that comes into contact with the patient's or subject's skin, when the physiological recording device is placed onto the patient or subject. The lower surface may take on many shapes or arrangements, and may further include a number of surface features for displacing, cracking, or perturbing the stratum corneum or outer layer of the epidermis, and accessing the lower layers of the epidermis, thus decreasing the electrical resistance of the electrical pathway from the lower layers to the physiological recording device. These surface features may take one of many forms including but not limited to ridges, columns, penetrators, anchors, epidermal stops and combinations thereof. These surface features, in general, protrude from the various shaped substrates described above. Preferably, there is at least one structure or surface feature protruding from the device's lower surface. One of the important secondary functions of the configuration of surface features is to displace or move the hair, dead skin cells and/or detritus so that the surface features can better collect the electrical biopotentials generated by the body.

The physiological recording device of the present invention further comprises an upper surface. In several embodiments of the present invention, the upper surface can have various types of connectors formed or attached on the top or upper surface of the physiological recording device. The connector can simply be a common button type connection in order to connect to standard terminals for various devices or can be shaped to provide for unique connecting features in order to require special terminals to be created for the monitoring device. These connectors may be integrated into or with the upper surface or may be a separate component attached to the upper surface.

Various embodiments of the present invention comprise a separate encouragement ring. The encouragement ring has an opening into which an electrode, or recording portion of the physiological recording device can be placed, and which allows the encouragement ring to surround and hold, preferably firmly, the recording portion. This encouragement ring provides stability to the physiological recording device such that when the device is placed on a subject's skin, the ring encourages the device to become seated in contact with the subject's skin and to minimize movement of the device. This encouragement ring effectively helps to further anchor the physiological recording device to the patient's or subject's skin by providing a biasing force that tends to drive or hold the device down onto the patient's or subject's skin and thus seating the device, and more importantly the surface feature(s), securely in contact with the patient's or subject's skin. This helps to increase signal quality and efficacy while minimizing artifacts, particularly movement artifacts, in the physiological signal being acquired. Additionally, the encouragement ring provides increased surface area to the upper surface of the physiological recording device which allows the device to be combined with an adhesive collar or some wearable device, system or garment to be applied to the subject's skin in a more stable and secure fashion. The encouragement ring may be of any shape (such as circular or rectangular) to accommodate the wearable garment or adhesive that may be used to apply the device to a subject.

Other embodiments of the present invention may not include a separate encouragement ring, but rather have a lip which may curve up from the lower surface of the physiological recording device acting like an encouragement ring, and which surrounds and provides an edge for a stamped or molded sheet metal or plastic piece. This lip provides the same function and utility as the separate encouragement ring described above, but is integrated into the physiological recording device when manufactured, and thus is not separate.

Many embodiments of the present invention, particularly those where the physiological recording device is constructed of a non-conductive material, comprise a conductive coating and/or ionic compound which helps to create an electrical pathway for signals to be transferred from the subject to the monitoring equipment, and to minimize electrical impedance of the device. Conversely, some embodiments may not require or utilize a conductive coating or ionic compound at all, most notably those embodiments wherein the device is constructed of a conductive metal. Alternatively, some embodiments may be coated in a less expensive metallized conductive coating (typically a polymer or plastic device), and receive a conductive coating and/or ionic compound on only a portion of the device, such as just the surface feature(s). Typically, this coating is a silver/silver chloride (Ag/AgCl) coating, but it may be of any conductive or ionic compound known to those in the art presently, or later developed for such use. Alternatively, Ag/AgCl or other conductive inks, such as those sold by DuPont (DuPont 5874), Ercon, and the like may be used, as well as any with the appropriate electrical and/or ionic properties, and which can be compounded and used for such applications as described herein.

The Ag/AgCl coating utilized may help to ensure the physiological recording devices are substantially nonpolarizable. Nonpolarizable electrodes are those in which current passes freely across the interface between the electrode and the skin, and thus require no energy to make the transition. A physiological recording device utilizing Ag/AgCl is typically governed by two separate reactions: 1) oxidation of silver atoms on the electrode surface to silver ions in the material at the interface, and 2) the combination of silver ions ($Ag^+$) with chlorine ions ($Cl^-$) at the material at the interface. In this case, the material at the interface containing the chlorine ions may include biological fluids of the subject. Thus this reaction may further be enabled by the concentration of chlorine ions in biological fluids. Thus, when the physiological recording device is placed in contact with the subject's skin, the Ag/AgCl coating on the device may first oxidize creating silver ions, and then those silver ions combine with free chlorine ions contained in the material at the interface including the biological fluids of the subject. This interface creates a substantially nonpolarized connection that allows for the free flow of biopotential signals from the subject into the physiological recording device with a minimized impedance. Preferably, the amount of Ag/AgCl used to create these reactions and minimize electrical impedance of the device is minimized in thickness, weight, and/or surface area in order to keep manufacturing costs low.

The physiological recording device can be formed from a variety of materials and processes known to those skilled in the art. The substrate from which the penetrators or other surface features are formed or to which they are added can, by way of example but not limitation, be made from the following: a conductive metal sheet, where such conductive metals include, but are not limited to, stainless steel, nickel, copper, aluminum, and the like; a semi-conductive materials including for example silicon and doped silicon wafers; ceramics including for example oxides; polymers including for example electrically conductive polymers such as polyimides; and other varieties of plastics. Preferably, all non-conductive substrates are coated, such as with Ag/AgCl, or doped to make the substrate semi-conductive or conductive. There are in general four processes by which embodiments of the present invention are preferably manufactured: injection molding, casting or depositing; replication; micromachining; or stamping or pressing from a sheet of metal, polymer sheet or polymer powders.

Other manufacturing methods that may be possibly, though less preferably, used to manufacture the physiological recording device include, but are not limited to: forming the physiological recording device from silicon wafers; additive deposition; drawing; extrusion; blow molding; thermoforming; rotational molding; casting; foaming; compression molding; transfer molding; laser machining; abrasion; or other metal working techniques, and the like.

In many embodiments, secondary processes are used to coat the device substrates with a metallized layer and/or a layer of conductive coating and/or ionic compound. These embodiments involve coating some portion of the device in a less expensive conductive coating. This coating may be a metallized coating, or a conductive coating or ionic compound that is less expensive than Ag/AgCl in order to transmit the biopotential or electrical signals from the surface features and/or lower surface of the device to the connector and to the monitoring equipment. This typically is useful for physiological recording device embodiments where the device is constructed of a polymer or plastic that is not conductive itself. Many of such embodiments will still utilize a minimal amount of conductive coating and/or ionic compound, such as Ag/AgCl, but only on a minimal portion of the lower surface, or more preferably, only on the surface features, or only on a portion thereof, such as just the tips. This allows the conductive coating and/or ionic compound to facilitate the desired redox reaction with ions in the material at the interface and thus drive the transfer of biopotential or electrical signals from the subject to the monitoring equipment, using the less expensive coating as an electrical pathway, while allowing the cost of the device to be minimized further.

The physiological recording device can be packaged by conventional packaging techniques, however, preferably the package provides: 1) adequate structural support for the device so it can be handled roughly (i.e., dropped, crushed, etc.) without damage; 2) a means (e.g., tape, belt or spring) preferably, to force the device against the subject's skin with a consistent pressure; 3) a low impedance path from the device's surface to the package's output connector; and/or 4) a design which allows for easy cleaning and sterilization for applications requiring reuse. These physiological recording device packages also can be mounted to the skin using conventional techniques such as adhesives, harnesses, straps or bands. Preferably, the physiological recording device and packaging are constructed to be reusable and/or disposable such that each device may be utilized multiple times, but are also easily disposable and replaceable.

It is understood that the physiological recording devices of the present invention may have a combination of the various surface features described throughout this application. Various features of the present invention are described within this patent application. It is understood that the present invention can be considered to embody many of these features in various combinations without departing from the spirit of the present invention. A small number of examples of the present invention are described in the following embodiments. Various features and functions of the present invention are discussed in greater detail in U.S. Pat. Nos. 6,782,283, 6,785,569, 7,032,301, 7,286,864, 8,201,330, 7,489,959, and 7,881,764, all of which are hereby incorporated by reference into the present application for patent.

One embodiment includes a physiological recording device comprising an recording portion further comprising an upper surface and a lower surface, the lower surface comprising at least one surface feature for displacing, cracking, or perturbing the stratum corneum and obtaining at least one physiological signal from the lower layers of the epidermis, the upper surface comprising a conductor connecting the recording portion to a physiological monitoring or recording device for passing along the at least one physiological signal from the lower surface, and in some embodiments may include a separate encouragement ring, the encouragement ring having an opening for surrounding and holding the recording portion.

Another embodiment of the present invention includes a physiological recording device comprising a stamped or molded sheet metal piece having an upper surface and a lower surface, the lower surface comprising at least one surface feature for displacing, cracking, or perturbing the stratum corneum and obtaining at least one physiological signal from the lower layers of the epidermis and a lip surrounding and providing an edge for the stamped or molded sheet metal piece, the lip curved up from the lower surface, and the upper surface comprising a connector for passing along the at least one physiological signal from the lower surface, and the lip curved up from the upper surface.

Still another embodiment of the present invention includes a physiological recording device comprising a stamped or molded sheet metal piece having an upper surface and a lower surface, the lower surface comprising at least one surface feature for displacing, cracking, or perturbing the stratum corneum and obtaining at least one physiological signal from the lower layers of the epidermis and a lip surrounding and providing an edge for the stamped or molded sheet metal piece, the lip curved up from the lower surface and from the upper surface.

Yet another embodiment of the present invention includes a method of manufacturing a physiological recording device comprising steps of forming, by molding, casting, extruding, thermoforming, foaming, or the like, an recording portion comprising an upper surface and a lower surface, the lower surface comprising at least one surface feature for displacing, cracking, or perturbing the stratum corneum and obtaining at least one physiological signal from the lower layers of the epidermis, and forming by molding, casting, extruding, thermoforming, foaming, or the like, a separate encouragement ring having an opening for surrounding and holding the recording portion in such a way that the lower surface of the recording portion can obtain at least one physiological signal from the lower layers of the epidermis.

Even still another embodiment of the present invention includes a method of manufacturing a physiological recording device comprising steps of forming, by molding, casting, extruding, thermoforming, foaming, or the like, an recording portion comprising an upper surface and a lower surface, the lower surface comprising at least one surface feature for displacing, cracking, or perturbing the stratum corneum and obtaining at least one physiological signal from the lower layers of the epidermis, coating the recording portion with a conductive coating and/or ionic compound, forming by molding, casting, extruding, thermoforming, foaming, or the like, a separate encouragement ring having an opening for surrounding and holding the recording portion in such a way that the lower surface of the recording portion can obtain at least one physiological signal from the lower layers of the epidermis, and assembling the encouragement ring about the recording portion of the physiological recording device.

Still yet another embodiment of the present invention includes a method of manufacturing a physiological recording device comprising steps of forming by molding, drawing or stamping a piece of sheet metal to have an upper surface and a lower surface, the lower surface comprising at least one surface feature for displacing, cracking, or perturbing the stratum corneum and obtaining at least one physiological signal from the lower layers of the epidermis and a lip surrounding and providing an edge for the stamped or molded sheet metal piece, the lip curved up from the lower surface, and the upper surface comprising a connector for passing along the at least one physiological signal from the lower surface, and the lip curved up from the upper surface, and coating the lower surface of the formed sheet metal piece on and/or around the at least one surface feature with a conductive coating and/or ionic compound.

Even yet another embodiment of the present invention includes a method of manufacturing a physiological recording device comprising steps of forming by molding, drawing or stamping a piece of sheet metal to have an upper surface and a lower surface, the lower surface comprising at least one surface feature for displacing, cracking, or perturbing the stratum corneum and obtaining at least one physiological signal from the lower layers of the epidermis and a lip surrounding and providing an edge for the stamped or molded sheet metal piece, the lip curved up from the lower surface, and the upper surface comprising a connector for passing along the physiological signals from the lower surface, and the lip curved up from the upper surface, and at least minimally coating the lower surface of the formed sheet metal piece on and/or around the at least one surface feature with a conductive coating and/or ionic compound.

Even still yet another embodiment of the present invention includes a physiological recording device comprising a separate recording portion comprising an upper surface and a lower surface, the lower surface of the separate recording portion comprising at least one surface feature for displacing, cracking, or perturbing the stratum corneum and obtaining at least one physiological signal from the lower layers of the epidermis, and the upper surface of the separate recording portion comprising a nesting connecting ring, a separate metal connector portion comprising an upper surface and a lower surface, the lower surface of the separate metal connector portion comprising an outer ring and an inner ring, and the upper surface of the separate metal connector portion comprising a connector for connecting the lower surface of the recording portion to a physiological monitoring or recording device, and a separate encouragement ring, the encouragement ring having an opening for surrounding and holding the combined recording portion and separate connector portion, wherein the nesting connecting ring of the separate recording portion fits between the inner ring and outer ring of the separate metal connector portion to form a complete recording device, and wherein the recording portion and the separate connector portion, when attached together, form a continuous electrical pathway from the lower surface of the recording portion to the upper surface of the separate connector portion for passing along the at least one physiological signal from the lower surface to the physiological monitoring or recording device.

Still even another embodiment of the present invention includes a method of manufacturing a physiological recording device comprising steps of forming by molding, drawing or stamping a piece of sheet metal to have an upper surface and a lower surface, the lower surface comprising at least one surface feature for displacing, cracking, or perturbing the stratum corneum and obtaining at least one physiological signal from the lower layers of the epidermis, and a lip surrounding and providing an edge for the stamped or molded sheet metal piece, the lip curved up from the lower surface, and the upper surface comprising a connector for passing along the at least one physiological signal from the lower surface, and the lip curved up from the upper surface, and minimally coating the lower surface of the formed sheet metal piece on and/or around the at least one surface feature with a conductive coating and/or ionic compound, wherein the minimal coating covers less than 80% of the surface area of the lower surface.

Even yet another embodiment of the present invention includes a method of manufacturing a physiological recording device comprising steps of forming, by molding, casting, extruding, thermoforming, foaming, or the like, a physiological recording device comprising an upper surface and a lower surface, the lower surface comprising at least two surface features for displacing, cracking, or perturbing the stratum corneum and obtaining at least one physiological signal from the lower layers of the epidermis, the upper surface comprising a connector, coating the at least two surface features with a conductive coating and/or ionic compound, providing a web or network of conductive coating and/or ionic compound interconnecting the at least two surface features, and providing a strip of conductive coating and/or ionic compound extending from the web or network connecting the at least two surface features to the edge of the lower surface and wrapping up and around the edge of the physiological recording device, and continuing across the upper surface to the connector.

Additional features and advantages of the invention will be set forth in the detailed description which follows, and in part will be readily apparent to those skilled in the art from that description or recognized by practicing the invention as described herein, including said detailed description, the claims, as well as the appended drawings.

It is to be understood that both the foregoing general description and the following detailed description are merely exemplary of the invention, and are intended to provide an overview or framework for understanding the nature and character of the invention as it is claimed. The accompanying drawings are included to provide a further understanding of the invention, and are incorporated in and constitute a part of this specification. The drawings illustrate various embodiments of the invention and together with the description serve to explain the principles and operation of the invention.

BRIEF DESCRIPTION OF THE DRAWINGS

FIG. 3. Cross section of a compression fitting embodiment whereby an independent dry physiological recording device is attached or inserted into an independent encouragement ring.

FIG. 4. Cross section of an assembled multi-part dry physiological recording device and encouragement ring with adhesive and integrated snap connector.

FIG. 5. Cross section of an assembled multi-part dry physiological recording device comprising a recording portion and a separate encouragement ring with adhesive and no snap connector.

FIG. 10A-C. Cross sections of a folding stamped monolithic dry physiological recording device comprising an encouragement lip, surface features, conductive or ionic compound, and snap connector depicting different embodiments wherein (A) the recording devices comprises a folding or picot point, Silver/silver chloride puck and conductive coating and/or ionic compound on the surface features; (B) a similar folding embodiment but with no Silver/silver chloride puck; and (C) another similar embodiment but with no folding or pivot point and no Silver/silver chloride puck.

FIG. 20A-D. Depiction of various embodiments of a physiological recording device comprising a separate encouragement in both a (A) top view and (B) side view, and a separate recording portion in both a (C) side view and (D) bottom view, which can be fitted together for use in monitoring electrophysiological signals from a subject.

DETAILED DESCRIPTION OF THE INVENTION

Figure 1A:
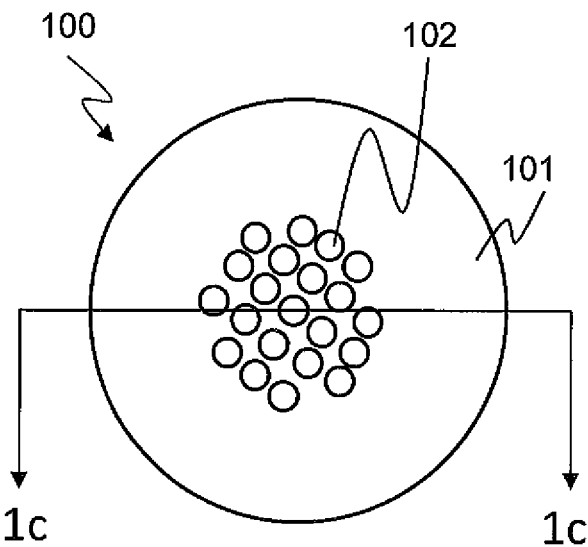
FIG. 1A-H. Illustration of several embodiments of a monolithic dry physiological recording device of the present invention from various perspectives, including: (A) bottom view; (B) top view; (C) cross-section with conductive coating and/or ionic compound; (D) bottom perspective view of lower surface; (E) side view without conductive coating and/or ionic compound; (F) bottom view of alternative reduced size embodiment; (G) cross-section of alternative reduced size embodiment with conductive coating or ionic compound; and (H) side view of alternative reduced size embodiment without conductive coating and/or ionic compound.

The present invention is directed to a physiological recording device and, more particularly, to a physiological recording device that can be used without skin preparation or the use of electrolytic gels. The invention is further directed to an encouragement ring which stabilizes and helps situate the physiological recording device on a subject's skin to help provide a better electrical signal, increase surface area, and to reduce and minimize noise and artifacts during the process of recording or monitoring a physiological signal. The invention is still further directed to surface features on a surface of the physiological recording device with a size and shape which that will not substantially bend or break, which limits the depth of application of the recording device, and/or anchors the recording device during normal application. The invention is even further directed to a method for manufacturing a physiological recording device.

The physiological recording device of the present invention comprises an upper and a lower surface. The lower surface can take many forms. For instance, the lower surface can be flat, concave, convex, or some other unique shape. The physiological recording device can be substantially flat on its lower surface. Various embodiments of the present invention could include changes in the physiological recording device's lower surface. Whether the lower surface is perpendicular to the device's vertical axis or sloped depends on the application. The physiological recording device can also be substantially concave on its lower surface. An example is where the lower surface is outwardly curved like a portion of the inner surface of a large sphere. The physiological recording device can also have a convex shape on its lower surface. An example is where the lower surface curves or bulges outward, like a portion of the exterior surface of a large sphere. The lower surface of the physiological recording device is not limited to one of the aforementioned shapes, and may take on a number of other unique shapes or some combination of the shapes listed above.

The lower surface of physiological recording device of the present invention may further include a number of surface features for displacing, cracking, or perturbing the stratum corneum or outer layer of the epidermis and accessing the lower layers of the epidermis. Such displacing, cracking, or perturbing of the skin may include the surface features physically penetrating the stratum corneum and accessing and physically contacting the lower layers of the skin. However, it may be preferable for the surface features to merely perturb, stretch, or open the stratum corneum by cracking or displacing it without actually physically penetrating it, in order to provide a lower electrical resistance pathway from the lower layers of the skin to the physiological recording device. The penetrating surface features can take many shapes including but not limited to pyramidal, needle-like, triangular, or any other shape that can be tapered to a point or tip. Preferably, the size and shape of the penetrator is such that the penetrator(s) will not break or bend during normal use, will limit the depth the penetrator enters the skin under typical application conditions, and/or will anchor the device to prevent motion artifacts or any substantial movement. Such surface features are explained in detail in U.S. Pat. No. 6,785,569 to Schmidt et al, which is herein incorporated by reference. These surface features may take one of many forms including but not limited to ridges, columns, penetrators, anchors, epidermal stops and combinations thereof. These surface features, in general, protrude from the various shaped substrates described above. Preferably, there is at least one structure or surface feature protruding from the device's lower surface. One of the important functions of the configuration of surface features is to displace or move the hair, dead skin cells and/or detritus so that the surface features can better collect the electrical biopotentials generated by the body.

The ridge(s) as used in the present invention is preferably a long, narrow structure or elevation. The ridge(s) can have a variety of cross sections over a length. Examples of these cross sections include but are not limited to a square, rectangle or trapezoid, a pointed surface like that of a triangle, a domed surface like that of an arch or arc, a cross section with a concave surface between to ridge lines forming the two ridge lines, some other unique cross-section or the like. The cross section of the ridge extends for a length. The length of the ridge is preferably substantially longer than the height or width of the cross-section of the ridge. The surface of the ridge away from the substrate, when applied to the skin surface, depresses, but does not need to penetrate the skin but anchors the device in place to prevent motion artifacts, to displace hair, dead skin cells and/or detritus, to increase the surface area of the device in contact with the skin, and to be capable, in part, of transmitting an electric potential which can be measured from the surface of the skin through the ridge.

A column(s) is another type of structure or elevation that can be used in the present invention. A column(s) can have a variety of cross sections over a length. Examples of these cross sections include but are not limited to a square, rectangle or trapezoid, a pointed surface like that of a triangle, a domed surface like that of an arch or arc, a cross section with a concave surface between two points (wherein the distance from the base to either point is greatest height of the column for the cross-section), some other unique cross-section or the like. The cross section of the column like a ridge extends for a length. However, the width of the column is preferably in proportion to the height of the cross-section of the column, and more preferably shorter than the height of the column. The surface of the column away from the substrate, when applied to the skin surface, depresses, and does not easily penetrate the skin but anchors the device in place to prevent motion artifacts, to displace hair, dead skin cells and/or detritus, to increase the surface area of the device in contact with the skin, and to be capable, in part, of transmitting an electric potential which can be measured from the skin through the ridge.

A penetrator(s) is also a surface feature that can be used in the present invention. The penetrator(s) is sized and shaped for displacing, cracking, or perturbing the stratum corneum or outer layer of the epidermis, and accessing the lower layers of the epidermis. The penetrator can take many shapes including but not limited to pyramidal, needle-like, triangular, or any other shape that can be tapered to a point or tip. The surface of the penetrator away from the substrate, when applied to the skin surface, readily penetrates the skin, preferably anchors the device in place to prevent motion artifacts or any substantial movement, increases the surface area of the device in contact with the skin and lower layers of the epidermis, and is capable, in part, of transmitting an electric potential which can be measured from the skin and lower layers of the epidermis through the penetrator.

The epidermal stop(s), which can be used in the present invention, is a structure or elevation. Epidermal stops are structures of a particular height with respect to the height of the penetrator(s) or other surface features so as to prevent the penetrator(s) or other surface features such as columns and ridges from penetrating into the dermis of the skin or unduly distorting the surface of the skin, respectively, where they might cause discomfort to the subject. An epidermal stop(s) may also be incorporated into a penetrator, ridge, column or like surface feature or can be a separate surface feature. The epidermal stops may, however, have any shape known to those skilled in the art that would effectively prevent the penetrator(s) from entering the dermis of the skin, or from being applied to deeply. The epidermal stops are preferably applied in an array among the penetrators, therefore further minimizing inadvertent deep penetration or over penetration by the penetrator(s) or minimizing significant distortion of the skin by other surface structures. If the epidermal stop is a separate surface feature or incorporated into another structure, preferably, the epidermal stop in combination with at least one other surface feature or two structures with incorporated epidermal stops create a detritus trough.

A detritus trough is the area interposed between adjacent surface structures or features. These troughs, when provided or naturally occurring in the design, allow for a more accurate placement of the surface features by allowing for displacement of the hair and other detritus on the skin in these troughs. Preferably, the detritus troughs are sufficient in number and size to allow for placement of the device on skin with a significant amount of hair such as for example the scalp or the chest of a male subject. Detritus troughs are created to maximize the area available for optimal device to skin contact, by improving the probability that hair and other detritus will enter the troughs and not preventing the surface features from either coming in contact with the skin or penetrating the skin. Thus detritus troughs may be parallel to one another, perpendicular to one another, or in any other orientation made to improve the contact of the device with the skin of the subject.

An anchor(s), which can be used in the present invention, is a structure or elevation that stabilizes the physiological device against a subject's skin. This stabilization further preferably prevents motion artifacts in the electrophysiological signal from the device, or any substantial movement. While the anchor can also be any of the structures described above, the anchor may also serve no other purpose except to stabilize or reduce movement of the device on the subject's skin. The anchor(s) can have a variety of cross sections over a length as described above for the various surface structures.

The ridges, columns and penetrators also increase the amount of surface area of the skin in contact with the physiological recording device, which is applied. This allows for greater pick up of (or stronger) signals from the skin's surface, and further allows for the physiological recording device to be better anchored to the subject's skin resulting in less artifacts to the signal through movement and the like. The electric voltage from these surface features is measured using conventional measuring devices.

The physiological recording device further comprises an upper surface which is the surface that faces away from the patient or subject when the physiological recording device is applied to the patient or subject. Preferably, the upper surface comprises some variety of connector used to connect the physiological recording device to monitoring equipment, and to complete an electrical pathway from the lower layers of the patient's or subject's skin to said monitoring equipment. The connector may be of any variety commonly known to those of skill in the art currently, or later developed. Examples of such connectors include, but are not limited to, snap connectors, button connectors, tension or compression fittings, and the like. Further, the upper surface of the physiological recording device may take on many shapes and configurations, for example it may be a flat surface, or may be curved in a convex or concave manner.

In certain embodiments, where the device is a multi-part dry physiological recording device, an independent, separate encouragement ring, to which an independent electrode component can be attached, may be provided. In such embodiments, the independent, separate encouragement ring comprises an opening in its center with a diameter equal to that of an independent, separate recording portion, preferably comprising surface features. The opening allows the recording portion to be placed inside of the encouragement ring's opening, and allows the encouragement ring to surround and hold the recording portion. The independent recording portion may attach to the opening of the encouragement ring by threads, a locking system, thermal compression, or like techniques. When the separate encouragement ring and recording portions are combined together, they form a single physiological recording device as described above, comprising an upper and a lower surface. The separate encouragement ring preferably curves up, away from the patient's or subject's skin when applied, such that, when viewed from the lower surface, the physiological recording device has a convex shape. This encouragement ring provides stability to the physiological recording device such that when the device is placed on a patient's or subject's skin, the ring encourages the device to become seated in contact with the subject's skin and to minimize movement of the device. This helps to increase signal quality and efficacy while minimizing artifacts in the physiological signal being acquired. Additionally, the encouragement ring provides increased surface area to the upper surface of the physiological recording device which allows the device to be combined with an adhesive collar or some wearable or garment to be applied to the subject's skin in a more stable and secure fashion.

The use of a separate encouragement ring provides many decided advantages over previous wet and dry electrodes alike. The separate encouragement ring allows for the physiological recording device to be manufactured using different materials for the different portions of the dive (i.e., separate encouragement ring and recording portions). The use of different materials for the different portions of the device provides benefits both in the manufacture and use of the recording devices. With respect to manufacturing, the separate encouragement ring may be constructed of a less expensive material, such as various low cost of plastics known to those skilled in the art. Thus, the entire separate encouragement ring, which constitutes a significant portion of the entire assembled recording device, may be made from a material, and by a process that reduces manufacturing costs, and therefore helps reduce overall cost of the recording device. Further, the separate encouragement ring allows for the amount of conductive coating and/or ionic compound required to be minimized by creating an electrical pathway between the two separate portions, rather than all the way out and around the edge of the encouragement ring. These cost cutting features particularly provide an advantage over existing dry electrodes which are known to those skilled in the art to be expensive to produce due to the use of expensive conductive materials, or the need to completely cover the device in an expensive conductive coating and/or ionic compound such as Ag/AgCl.

In addition to reducing costs of the device, using a separate encouragement ring allows the encouragement ring and the recording portion to be constructed of materials that have different properties to provide different features to the device. For example, the recording portion is preferably constructed of a material that has electrical conductive properties and electrical impedance properties that are conducive to transmitting biopotential signals from the subject or patient to the monitoring equipment, or alternatively (or additionally) may be a non-conductive material that is coated in a conductive layer such as Ag/AgCl to reduce the impedance, provide an electrical pathway, and provide a redox reaction promoting the flow of ions and thus allowing for better signal transmission. However, the encouragement ring being constructed of a different material allows the ring to provide additional characteristics, features, or properties to the device when assembled. The separate encouragement ring may be constructed of a material with a particular stiffness which helps anchor the device more securely to the patient's or subject's skin. Particular levels of flexibility may also be achieved with the encouragement ring, allowing the device to be situated on a curvier or less regularly-shaped part of the body while still providing the function of situating the recording portion in secure contact with the patient's or subject's skin. The encouragement ring material can be chosen based on any number of such desired features or characteristics, and still provide the reduction in cost while maintaining the secure fit of the electrode to the body. The end result of providing a separate encouragement ring constructed of a different material is that the function of the encouragement ring, to provide anchoring of the device to the patient's or subject's skin, can be optimized to better situate or apply the device in different locations of the body. Different materials yield different properties in the encouragement ring, and thus provide the applicable biasing forces causing the device to anchor to the skin, differently in different locations. Some encouragement rings may be adapted to affix the device to hairy regions of the body, or to curvier regions. Having a separate encouragement rings allows the device to be applied in many different locations and fashions, while still providing the required biasing forces to the subject's skin to drive the device down into the skin, and more securely anchor the device thereto. This ensures a higher quality signal is transmitted from the patient or subject to the monitoring equipment, and further minimizes artifacts and noise within the signal. The separate encouragement ring may be attached to the electrode or recording portion by any means currently known to those in the art or later developed, including, but not limited to, threads, compression, clips or other mechanical fixture methods, adhesives, and the like.

Other embodiments of the present invention do not include a separate encouragement ring. In such embodiments, the physiological recording device is made from a single piece of material, and the physiological recording device preferably comprises a lip extending radially outward and curving upward away from the lower surface of the recording device, surrounding and providing an edge for a stamped or molded sheet metal or plastic piece. This lip provides the same function and utility as the separate encouragement ring described above, but is part of a unitary construction of the physiological recording device, rather than being a separate piece that is later attached to a separate recording portion. The lip comprises the edge or near edge portion of the physiological recording device, and the lip is herein preferably defined as the portion where the lower surface of the physiological recording device begins to curve upward to the edge or near edge of the physiological recording device.

The distance of the curved lip portion is herein defined as the distance of curvature of the lip. The same distance of curvature definition applies to the curved portion of the separate encouragement ring in embodiments comprising a separate encouragement ring. The curvature of the lip or encouragement ring may be wholly contained in the lip or encouragement ring portion, or may begin in the lower surface of the recording portion of the device itself. That is, the lower surface itself need not be entirely flat, but may gradually curve up into the lip or encouragement ring. Many embodiments are envisioned with both constructions: either with a flat area between the lower surface where the surface features are located and where the lip or encouragement ring begins, or where the lower surface itself begins to curve up and meet the curvature of the lip or encouragement ring to form an essentially smooth curve. In all embodiments, preferably, the distance of curvature of the lip or separate encouragement ring is greater than 0.2 cm. More preferably, the distance of curvature of the lip or separate encouragement ring is greater than 0.25 cm. Still more preferably, the distance of curvature of the lip or separate encouragement ring is greater than 0.3 cm. Yet more preferably, the distance of curvature of the lip or separate encouragement ring is greater than 0.4 cm. Even more preferably, the distance of curvature of the lip or separate encouragement ring is greater than 0.45 cm. Still yet more preferably, the distance of curvature of the lip or separate encouragement ring is greater than 0.5 cm. Still even more preferably the distance of curvature of the lip or separate encouragement ring is greater than 0.6 cm. Yet still more preferably, the distance of curvature of the lip or separate encouragement ring is greater than 0.75 cm. Yet even more preferably, the distance of curvature of the lip or separate encouragement ring is greater than 1.0 cm. Even yet more preferably, the distance of curvature of the lip or separate encouragement ring is greater than 1.5 cm. Most preferably, the distance of curvature of the lip or separate encouragement ring is greater than 2.0 cm.

The lip, by its very nature, has a radius of curvature which defines the rate at which the lip curves upward from the lower surface of the physiological recording device. It is to be understood that the entire lip or encouragement ring does not need to have the same or constant radius of curvature along the entire distance of curvature. In other words, it is important to note that the radius of curvature may change along the length of the distance of curvature. Preferably, the radius of curvature of the lip or encouragement ring over substantially all of the distance of curvature is greater than 0.5 cm. More preferably, the radius of curvature of the lip or encouragement ring over substantially all of the distance of curvature is greater than 0.75 cm. Still more preferably, the radius of curvature of the lip or encouragement ring over substantially all of the distance of curvature is greater than 1.0 cm. Yet more preferably, the radius of curvature of the lip or encouragement ring over substantially all of the distance of curvature is greater than 1.125 cm. Even more preferably, the radius of curvature of the lip or encouragement ring over substantially all of the distance of curvature is greater than 1.25 cm. More preferably still, the radius of curvature of the lip or encouragement ring over substantially all of the distance of curvature is greater than 1.5 cm. Yet more preferably still, the radius of curvature of the lip or encouragement ring over substantially all of the distance of curvature is greater than 1.75 cm. Still even more preferably, the radius of curvature of the lip or encouragement ring over substantially all of the distance of curvature is greater than 2.0 cm. Even still more preferably, the radius of curvature of the lip or encouragement ring over substantially all of the distance of curvature is greater than 2.5 cm.

Numerous embodiments of the present invention, particularly those where the physiological recording device is constructed of a non-conductive material, comprise a conductive coating and/or ionic compound which helps to create an electrical pathway for signals to be transferred from the subject to the monitoring equipment, and to minimize electrical impedance of the device. Preferably, the physiological recording device comprises a silver/silver chloride (Ag/AgCl) coating over all or a portion of the physiological recording device, though other similar coatings are contemplated for use with the recording device. Silver/silver chloride, and other like conductive or ionic compounds, help provide a conductive pathway for electrical signal, particularly biopotential signals, to be transferred from the subject's skin to monitoring equipment. Additionally, the conductive coating and/or ionic compound helps reduce electrical impedance of the device, which helps provide better signal quality and reduce signal noise and artifacts.

Preferably, the conductive coating and/or ionic compound covers no more of the physiological recording device than necessary, and is minimized to reduce cost of manufacturing the device. In monolithic embodiments, the conductive coating and/or ionic compound typically and traditionally can cover the entire lower surface of the physiological recording device and at least some portion of the upper surface connecting the lower surface to the connector of the upper surface of the device, creating a continuous pathway of the conductive coating and/or ionic compound from the lower surface to the connector. The present invention provides unique methods, products, and devices to minimize the amount of this coating required in order to help reduce costs of the device. Some embodiments provide the conductive coating and/or ionic compound on a portion of the lower surface of the device, for example only coating the center most portion of the lower surface, or coating just the tips or ends of the surface feature(s) which are in contact with the subject's skin when the device is applied to the subject. In such embodiments, preferably less than 90% of the lower surface has the conductive coating and/or ionic compound. More preferably less than 80% of the lower surface has the conductive coating and/or ionic compound. Still more preferably less than 70% of the lower surface has the conductive coating and/or ionic compound. Even more preferably less than 60% of the lower surface has the conductive coating and/or ionic compound. Even still more preferably less than 50% of the lower surface has the conductive coating and/or ionic compound. More preferably still, less than 40% of the lower surface has the conductive coating and/or ionic compound. Even still more preferably less than 30% of the lower surface has the conductive coating and/or ionic compound. Still yet more preferably, less than 20% of the lower surface has the conductive coating and/or ionic compound. Even still more preferably, less than 10% of the lower surface has the conductive coating and/or ionic compound.

In other monolithic embodiments, the coating is not applied to the lower surface of the device based the inner radius of the lower surface covered, but rather such coating is further minimized by application only to the surface features located on the lower surface. These embodiments differ from the above described embodiments because the coating here is only applied to the surface features and enough of the interstitial space between the surface features to create a web-like conductive network connecting each of the surface features to each other. In other words, the coating is not applied to the entire selected inner radius of the device, thus coating the entire inside of that radius, but is rather selectively and specifically applied to the surface features and a network connecting those surface features together. This allows the amount of coating required to be minimized even further, and thus reduce costs even further. In such embodiments, preferably less than 30% of the lower surface has the conductive coating and/or ionic compound. More preferably less than 25% of the lower surface has the conductive coating and/or ionic compound. Even more preferably less than 20% of the lower surface has the conductive coating and/or ionic compound. Still more preferably less than 15% of the lower surface has the conductive coating and/or ionic compound. Even still more preferably less than 10% of the lower surface has the conductive coating and/or ionic compound. In such embodiments, the percentage of the lower surface which is covered in the conductive coating and/or ionic compound is easily managed by decreasing the amount of connecting pathways between surface features and/or decreasing the width and depth of the coating constituting those pathways.

Another way to measure the amount of conductive coating and/or ionic compound used, in order to minimize that amount, is by the amount of surface area that is actually covered. In regards to actual surface area coated, preferably, the surface area coated in conductive coating and/or ionic compound is less than 6 $cm^2$. More preferably, the surface area coated in conductive coating and/or ionic compound is less than 5.5 $cm^2$. Still more preferably, the surface area coated in conductive coating and/or ionic compound is less than 5 $cm^2$. Yet more preferably, the surface area coated in conductive coating and/or ionic compound is less than 4.5 $cm^2$. Even more preferably, the surface area coated in conductive coating and/or ionic compound is less than 4 $cm^2$. More preferably still, the surface area coated in conductive coating and/or ionic compound is less than 3.5 $cm^2$. Yet more preferably, the surface area coated in conductive coating and/or ionic compound is less than 3 $cm^2$. Still yet more preferably, the surface area coated in conductive coating and/or ionic compound is less than 2.5 $cm^2$. Even still more preferably, the surface area coated in conductive coating and/or ionic compound is less than 2 $cm^2$. Even still yet more preferably, the surface area coated in conductive coating and/or ionic compound is less than 1.5 $cm^2$. Still even more preferably, the surface area coated in conductive coating and/or ionic compound is less than 1 $cm^2$. Even still yet more preferably, the surface area coated in conductive coating and/or ionic compound is less than 0.75 $cm^2$. Still even more preferably yet, the surface area coated in conductive coating and/or ionic compound is less than 0.5 $cm^2$.

In both varieties of embodiments of the above described monolithic dry physiological recording devices, the minimized area of conductive coating and/or ionic compound on the lower surface of the device must comprise a continuous pathway of the coating from that coated area to and around the edge of the encouragement lip to the upper surface of the device, and to the connector located on said upper surface. Such continuous pathway allows the biopotential signals to be transmitted from the subject or patient to the monitoring equipment in spite of the use of a non-conductive physiological recording device body and a preferably minimized amount of conductive coating and/or ionic compound. Preferably, this continuous pathway is created by providing a strip-like path of the conductive coating and/or ionic compound from the portion of the lower surface out from the center of the lower surface towards the edge of the device, around the edge of the device thus connecting the lower surface to the upper surface, and then to the center of the upper surface of the device and to the connector. In some embodiments, multiple such strips are provided to ensure a strong, secure electrical pathway from the surface features to the connector and to the monitoring equipment, for example in case one pathway becomes damaged, rubs away, or is otherwise broken. However, preferably, only a single pathway of connective coating is provided, and is applied in a manner and with properties so as to ensure a continuous electrical connection and pathway.

The conductive coating and/or ionic compound may also be utilized in manufacturing the multi-part or non-monolithic embodiments of the present invention. In such embodiments, it is preferred that only the recording portion of the device receives conductive coating and/or ionic compound, and that the separate encouragement ring is not coated at all. In these embodiments, the conductive coating and/or ionic compound is applied according to the same preferred limitations as described above for the monolithic embodiments, specifically in terms of the percentage of the lower surface of the recording portion covered, the percentage of the lower surface covered by the surface features and an interconnecting web of coating, or the percentage of the lower surface covered that comes in contact with the patient's or subject's skin. Further, in embodiments where the entire recording portion is not covered in conductive coating and/or ionic compound, the same electrical pathway is applied connecting the surface features and lower surface of the electrode to the upper surface and connector. In such embodiments, the continuous conductive coating and/or ionic compound pathway(s) do not extend out and around the separate encouragement ring, but rather extend up the side of the recording portion and provide the pathway between the recording portion and the separate encouragement ring when assembled together.

In all embodiments, the amount of conductive coating and/or ionic compound used is preferably minimized further by decreasing the thickness of the conductive coating and/or ionic compound, the total surface area of the device coated, or any combination of such factors. With respect to thickness, preferably, the conductive coating and/or ionic compound is less than 100 μm thick. More preferably, the conductive coating and/or ionic compound is less than 80 μm thick. Even more preferably, the conductive coating and/or ionic compound is less than 60 μm thick. Still more preferably, the conductive coating and/or ionic compound is less than 50 μm thick. Yet more preferably, the conductive coating and/or ionic compound is less than 40 μm thick. Still yet more preferably, the conductive coating and/or ionic compound is less than 30 μm thick. Even still yet more preferably, the conductive coating and/or ionic compound is less than 25 μm thick. Still even more preferably, the conductive coating and/or ionic compound is less than 20 μm thick. Even still yet more preferably, the conductive coating and/or ionic compound is less than 10 μm thick. Most preferably, the conductive coating and/or ionic compound is 5 μm thick or less. With respect to the total surface area of the device covered with the conductive coating and/or ionic compound, preferably less than 60% of the device's surface area is coated. More preferably, less than 50% of the device's surface area is coated. Even more preferably, less than 40% of the device's surface area is coated. Still more preferably, less than 30% of the device's surface area is coated. Even still more preferably, less than 25% of the device's surface area is coated. Still even more preferably, less than 15% of the device's surface area is coated.

In order to help achieve a minimized amount of coating used, a selective coating application process is used. The conductive coating and/or ionic compound is preferably applied to the device(s) after formation; however, such application may be performed prior to forming the device if the conductive coating and/or ionic compound or ink or solution is adapted and modified to allow drawing and forming of the ink material during the device formation process. The conductive coating and/or ionic compound can be applied to the device(s) via numerous methods. One such method, particularized for a silver/silver chloride (Ag/AgCl) coating, involves applying a coating of a fine silver powder to the device, then ball-milling the silver-coated device to leave only a thin coating of the powder on the device. The device(s) are then run through an electrolytic chlorine bath to chlorinate the silver powder coating, and to create a silver/silver chloride coating on the device. Other methods may utilize silver/silver chloride inks or solutions (or inks or solutions of other conductive coatings or ionic compounds) for coating the device, the surface feature(s), or a combination thereof according to the designs described herein. The inks or solutions of the conductive coating and/or ionic compound can be used to screen-printing a design of the coating onto the device. Screen printing involves pressing the ink or solution through a mesh screen, whereby a stencil is used to block of the pattern in such a way that ink or solution passes through the screen, but not where the stencil is located. Thus, the stencil acts as a negative image of the desired pattern for the conductive coating and/or ionic compound ink or solution. Another process that may be used to apply conductive coatings or ionic compounds is pad printing, which involves applying the ink or solution to a printing plate that contains an image of the desired ink pattern, then applying a transfer pad to the printing plate, thus transferring the ink image onto the transfer pad, and then applying the transfer pad to the substrate (in this case the physiological recording device) to transfer the ink layer from the transfer pad to the substrate. Another method of applying the coating is via a dip coating process whereby the device is lowered into a pool, reservoir, or thin layer of the conductive material only to the point where the conductive material covers the surface features, or the tips or ends of the surface features, but not the actual lower flat surface of the device. Alternatively, a masking process may be used whereby a negative image of the desired coating pattern is placed over the lower surface of the device, the conductive coating and/or ionic compound is applied and only adheres to the device through the apertures in the mask, and the residual coating is removed from the mask and applied later to another device. This method allows for quick and easy application of increasingly complex patterns of coating to the lower surface of the device while not allowing any of the coating to go to waste and while minimizing the design costs associated with applying the complex patterns that may be desired. Other processes known to persons skilled in the art may similarly be used to apply the conductive coating and/or ionic compound to the device, including, but not limited to flexographic printing, gravure, photo-pattern printing, inkjet or 3D printing, and the like so long as the process may be adapted to apply layers of the conductive coating and/or ionic compound onto the device.

In numerous embodiments, an Ag/AgCl puck is utilized. In these embodiments, the puck is preferably placed in the electrical pathway, and the device may or may not require a conductive coating and/or ionic compound, as described above, on the lower surface, or a portion thereof, of the physiological recording device. The Ag/AgCl puck is preferably connected in series with the subject and the conductive portion of the electrode, whether it be metal or a conductive coating and/or ionic compound. The series connection thus allows the Ag/AgCl puck to drive the flow of ions according to the oxidation and reduction reaction process described above, and thus draw the biopotential signals from the subject and to the physiological recording device for further transmission to the monitoring equipment. Where no further conductive coating and/or ionic compound is provided, some other conductive pathway must be provided connecting the lower surface of the device to the connector, and the Ag/AgCl puck must be placed in series in that conductive pathway. Other conductive pathways may include a metallic strip traversing and connecting the lower surface of the recording device to the connector, or the like.

The physiological recording device can be formed from a variety of materials and processes known to those skilled in the art. The substrate from which the penetrators or other surface features are formed or to which they are added can, by way of example but not limitation, be made from the following: a conductive metal sheet, where such conductive metals include, but are not limited to, stainless steel, nickel, copper, and the like; semi-conductive materials including for example silicon and doped silicon wafers; ceramics including for example oxides; polymers including for example electrically insulating polymers such as polyimides; and other varieties of conductive and non-conductive plastics. Preferably, all non-conductive substrates are coated, such as with Ag/AgCl or some other conductive or ionic compound, or doped to make the substrate semi-conductive or conductive. There are in general four processes by which embodiments of the present invention are preferably manufactured, though manufacturing is not limited to these four methods. Rather, the devices of the present invention can be manufactured by any means currently known to those of skill in the art, or those later developed.

One such process is where the device is formed by injection molding, casting or depositing a material into a mold to produce a dry physiological recording device comprising single piece construction, or optionally multiple piece construction. The lower surface of the device may also be formed by replication techniques such as using a replication roll, which forms the negative image of the desired surface features of the lower surface of the device or by stamping or pressing different materials. In replication, a web of polymer material is heated to soften the material and then passed over or under a replication roll to form the desired surface features of the lower surface of the physiological recording device, generally, hundreds to thousands to possibly even millions of times over the length of the web of polymer material. The replicating roll is either internally cooled causing the web to re-harden during replication, or the web of polymer material is cooled to re-harden the polymer material after replication but prior to re-winding the web. The replicator processed web of polymer material can then be diced or sliced at some point into individual pieces, which form the lower surface of the physiological recording physiological recording device. Similarly, the lower surface of such devices can be stamped or pressed from polymer sheet or polymer powders respectively. In the case of stamped devices, a polymer sheet material is drawn to create the surface features. In the case of pressed devices, polymer powders are pressed then sintered.

Some embodiments of the physiological recording device are preferably formed using an injection molding technique. The injection mold is preferably formed from a metal, more preferably, the mold has sintered mold inserts in the areas requiring fine detail, and most preferably the sintered mold inserts are made out of materials such as Porcerax. Porcerax is a sintered porous metal with porosity in the range of 20 to 30% by volume, and requires complex machining, polishing, cleaning, and maintenance. These sintered porous materials have a system of interconnected pores dispersed throughout the material. These types of materials, when used in appropriate areas, eliminates gas buildup, reduces injection pressure, lowers cycle times, gloss levels and substantially reduces scrap and reject rates. This type of sintered mold insert also allows for the production of the very fine micro-features or surface structures that populate the physiological recording device's lower surface by allowing for the removal of air from the mold when creating these features. The mold is designed such that the imprint, or negative image, of the desired surface features that may include the penetrators, anchors, ridges, columns, detritus troughs, epidermal stops, and combinations thereof are formed to allow the substantial escape of gas during the molding process in the areas where these micro-features are formed. The injection mold may also require a core pin to mold the undercut of the snap stud in once piece, if a snap stud is the method of connection. The snap stud feature is created to maintain compatibility with most existing electrode snap connectors. As described later, however, there are other embodiments that are contemplated which allow for other types of connection of the devices of the present invention with connecting wires or leads. The mold may be filled via injection molding, casting, deposition or other material forming technique to produce the desired physiological recording device. Preferably, the material that actually forms the physiological recording device is a polymer, more preferably the material is a thermoplastic, still more preferably the material is a liquid crystal polymer resin, and even more preferably the material is ABS. ABS is a material that offers unique combinations of toughness, stiffness, low mold shrinkage, and excellent flow properties which are all essential for the production of micro-features.

Once formed by injection molding, the physiological recording devices are ejected and cooled. The physiological recording device is then trimmed to remove any imperfections or to impart any physiological recording device characteristics, which cannot be obtained through molding. Optionally, and as a function of the conductivity of the material utilized, the surface may be further doped to increase the conductivity of the physiological recording device surface or of just the surface features, and also various film layers and leads can be coated onto the physiological recording device to make it individually addressable or to function as desired in an array of electrodes. Preferably, the device is coated with a conductive metal surface via physical vapor deposition (PVD), or sputtering. The deposition material, silver or gold, is transferred to the substrate material with such energy as to cause the metal to intermingle with the substrate at the atomic level. More preferably, however, the device is coated with an electroplating technique using silver or gold coatings. Even more preferably, the device is coated with silver-silver chloride (Ag/Ag—Cl) which results in a non-polarizable device with better ohmic behavior and greater electrical stability (less noise). In coating the device with silver-silver chloride a standard electroplating process is used. The devices after coating, however, are not polished, which maintains a roughened surface thereby improving skin surface contact, and if an adhesive collar is used for adhesion of the collar to the surface of the device.

In embodiments utilizing a multi-part construction comprising a separate encouragement ring and an electrode or recording portion, the separate encouragement ring may be manufactured by the same process as the electrode or recording portion, or may be manufactured by a separate or different process. It is preferable to manufacture the encouragement ring using a less expensive material, and by means of a less expensive process in order to further decrease the cost of the device. Many embodiments of the present invention provide an electrical pathway from the electrode or recording portion's surface features to the connector that travels between the electrode or recording portion and the separate encouragement ring. This allows for minimization of the conductive or ionic compound coating the device, as well as of the amount of more expensive materials required to construct the device. In such embodiments, because the separate encouragement ring need not have any conductive properties, it can be manufactured in the absolute least expensive means possible so long as it still provides the ability to stabilize and secure the electrode or recording portion to the subject's skin. In all embodiments comprising a separate encouragement ring and electrode or recording portion, the manufacturing process may be selected in such a way so as to minimize the cost of the device.

Another preferred method of manufacturing some embodiments of the present invention is by stamping. Preferably, for stamped metal embodiments, a high quality metal is used, such as stainless or surgical steel. Most preferably, only medical grades of metal are used. In such stamping processes, a piece of preferred sheet metal is entered into a press which contains a mold or model of the desired lower surface image of the device. The mold or model is then pressed into the sheet metal, thus forming the desired image into the sheet metal. Because such embodiments of the device are constructed from metal and thus are inherently conductive, they may be used as-is, without providing a conductive coating and/or ionic compound. However, some embodiments may utilize a conductive coating and/or ionic compound with such stamped metal electrodes. In those embodiments still using a conductive coating and/or ionic compound, preferably only the surface features are coated in order to minimize the amount of conductive coating and/or ionic compound required, and thus keep costs low. More preferably, only the tips of the surface features are coated, thus allowing for the nonpolarizing reactions to occur and minimize impedance of the device while minimizing the material cost for applying expensive coating. With regard to the amount of coating used in the stamped metal embodiments, preferably less than 75% of the surface area of the surface features is coated. More preferably, less than 50% of the surface area of the surface features is coated. Even more preferably, less than 40% of the surface area of the surface features is coated. Still more preferably, less than 30% of the surface area of the surface features is coated. Even still more preferably less than 20% of the surface area of the surface features is coated. More preferably still, less than 10% of the surface area of the surface features is coated.

When coating the lower surface of the device in conductive coating and/or ionic compound, it may be preferably, in some embodiments, to coat only the surface features, or only a portion of the surface features to further minimize the amount of conductive coating and/or ionic compound utilized. In such embodiments, it is preferable to coat at least the portion of the surface features that comes into direct contact with at least the outer layer(s) of the subject's skin. Preferably, in many embodiments where the device itself, or at least the electrode or recording portion, is made of a conductive metal or other material, the conductive coating and/or ionic compound, such as Ag/AgCl, is applied in a manner to more directly contact the subject's fluids, which contain chlorine ions, and thus create the desired redox reaction to drive transmission of the biopotential signals. Thus, only the very tip of surface features may need to be coated because that minimal amount of coating or compound may be sufficient to place the conductive coating or ionic compound in contact with fluid from the subject's body as the surface feature displaces, cracks, or perturbs the outer layer(s) of the skin, and thus to create the reaction and allow the device to record a stronger signal from the subject. Thus, only a portion of each surface feature may be coated where not the entire surface feature will contact the skin or penetrate to the layers where the reaction will more readily occur. Preferably, in such embodiments, less than 90% of the surface feature(s)'s distal tip or end is coated in conductive coating and/or ionic compound. More preferably, less than 80% of the surface feature(s)'s distal tip or end is coated in conductive coating and/or ionic compound. Still more preferably, less than 70% of the surface feature(s)'s distal tip or end is coated in conductive coating and/or ionic compound. Yet more preferably, less than 60% of the surface feature(s)'s distal tip or end is coated in conductive coating and/or ionic compound. Even more preferably, less than 50% of the surface feature(s)'s distal tip or end is coated in conductive coating and/or ionic compound. Even still more preferably, less than 40% of the surface feature(s)'s distal tip or end is coated in conductive coating and/or ionic compound. Even yet more preferably, less than 30% of the surface feature(s)'s distal tip or end is coated in conductive coating and/or ionic compound. Still even more preferably, less than 20% of the surface feature(s)'s distal tip or end is coated in conductive coating and/or ionic compound. Further in some embodiments comprising more than one surface feature on the device, it may be preferable to coat only a portion of the surface features. For example, in an embodiment with both penetrators and epidermal stops, there may be little need to coat the epidermal stops, but the penetrators would be coated so that when they penetrate the skin the coating can facilitate the desired redox reaction.

Turning now to a description of the figures, FIG. 1 is an illustration of several embodiments of a monolithic physiological recording device of the present invention from (A) a bottom view, (B) a top view, (C) a cross section, (D) a perspective view, and (E) a side view, as well as an alternate embodiment where the device is decreased in size in one axis, shown from (F) a bottom view, (G) a cross section, and (H) a side view. The monolithic physiological recording device 100 is preferably manufactured from a single piece of a material. In many embodiments, this material is a plastic or polymer which is strong enough to retain its shape and withstand the forces required to attach the device or place it in contact with a subject's body or skin, attach and remove lead wire connectors, and those encountered from the subject's own movement. In various other embodiments, the material may be of a metal, preferably stamped, and also able to withstand the above forces.

FIG. 1A shows a monolithic physiological recording device 100 of the present invention made from a single piece of plastic or polymer and coated with a conductive or ionic compound or material (not shown) from a bottom view, thus depicting the lower surface 101 of the device, with an array of surface features 102 arranged about the center of the lower surface 101 of the device. The surface features 102 are designed to displace, crack, or perturb, but not enter the skin when placed in contact with a subject to allow the device to transmit physiological signals from the conductive layers of the epidermis through the electrode or physiological recording device.

Figure 1C:
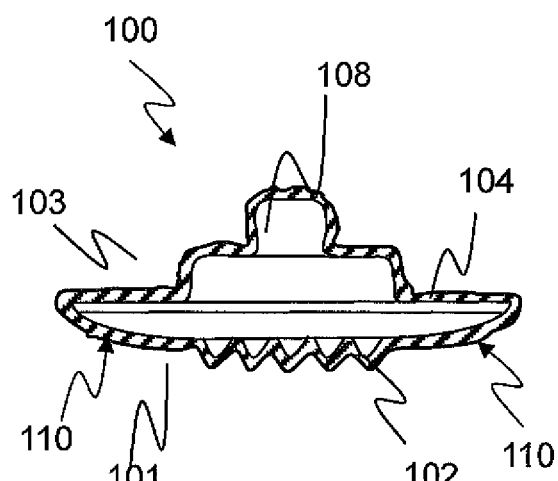
Figure 1B:
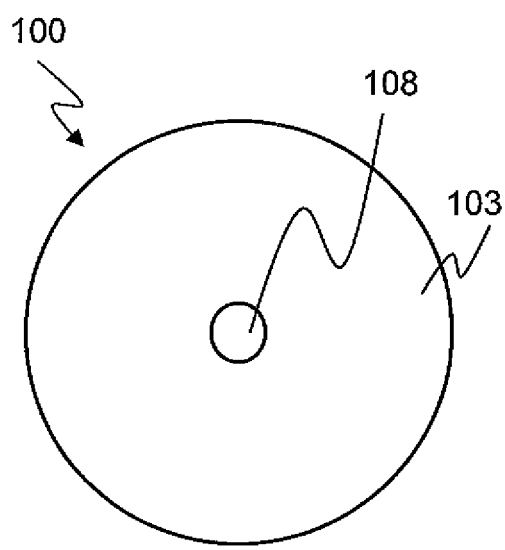

FIG. 1B shows the same monolithic device 100 from FIG. 1A, but from a top view, thus depicting the upper surface 103 of the device. On top of the monolithic device 100 is a connector 108, in this particular depiction a snap connector, for electrically and mechanically connecting the monolithic device 100 to monitoring equipment (not shown) that may use the monolithic device 100 for measuring biopotentials or physiological signals from a subject to whom the monolithic device 100 is attached or applied.

FIG. 1C illustrates a cross section of the monolithic physiological recording device 100. Again, the connector 108 is located on the upper surface 103 of the monolithic device 100, and surface features 102 are located on the lower surface 101 of the monolithic device. Surrounding the base, and constituting the outer edge of the monolithic device, and particularly the lower surface 101 (though the upper surface 103 may be curved as well) is an encouragement lip 110 for helping the monolithic device 100 remain in stable, secure contact with a subject's skin by stabilizing and helping to situate or force the surface features of the device against the subject's skin. The cross section in FIG. 1C also shows a conductive coating and/or ionic compound 104 (depicted as the hatched area surrounding the entire physiological recording device), for example of silver/silver chloride (Ag/AgCl), around the entirety of the monolithic device 100. The conductive coating and/or ionic compound 104 facilitates a reduction-oxygenation (redox) reaction with ions within a subject's biological fluid necessary for recording biopotentials, and further helps minimize electrical impedance and provide a conductive electrical pathway for biopotentials to be transmitted from the lower layers of the patient's skin (not shown) to the monitoring equipment (not shown).

Figure 1D:
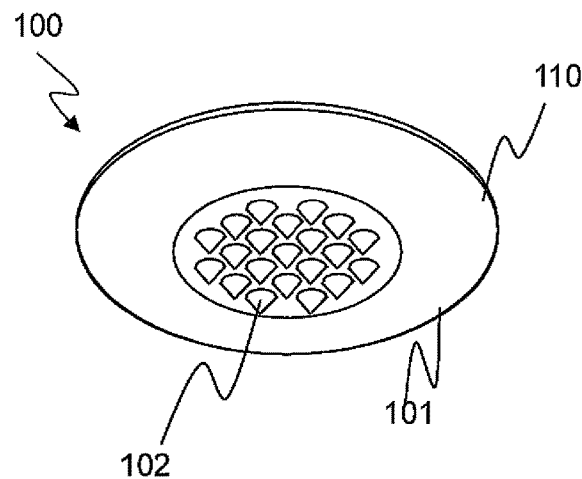

FIG. 1D shows a bottom perspective view of the monolithic device 100. Both the distance and radius of curvature of the encouragement lip 110 are depicted, as well as one embodiment of the surface features 102 in the form of penetrators. In this particular embodiment, the surface features 102 are conical in shape and tend connect the device to the outer layer(s) of the subject's skin, and thus decrease resistance to the transmission of biopotential signals from the lower layers of the skin to the monitoring equipment.

Figure 1E:
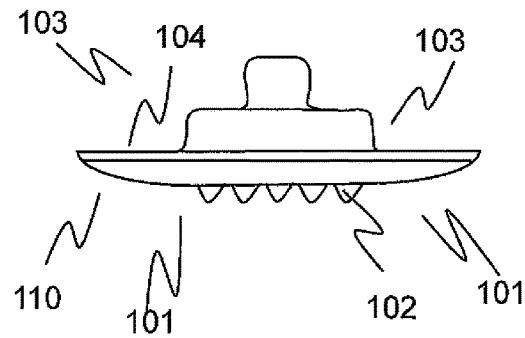

FIG. 1E illustrates a side view of the monolithic device 100. Again, the connector 108 is located on the upper surface 103 with the surface features 102 located on the lower surface 101 of the device. The encouragement lip 110 is shown with the radius of curvature and distance of curvature as the curving upward of the lower surface 101 of the monolithic device 100, which further comprises the surface features 102, and where the encouragement lip extends from the base of the surface features 102 to the outer edge of the device, where the lower surface 101 meets the upper surface 103. This upward curvature from the center helps stabilize and situate the device against the patient's skin. As opposed to FIG. 1C, the conductive coating and/or ionic compound has been left off of this depiction to more clearly show the other features of the device.

Figure 1F:
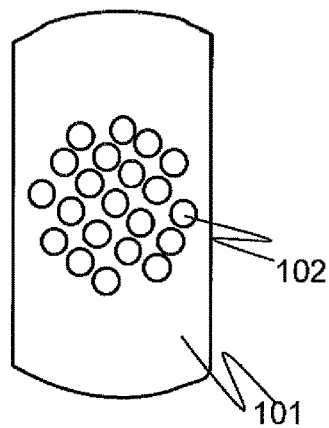
Figure 1G:
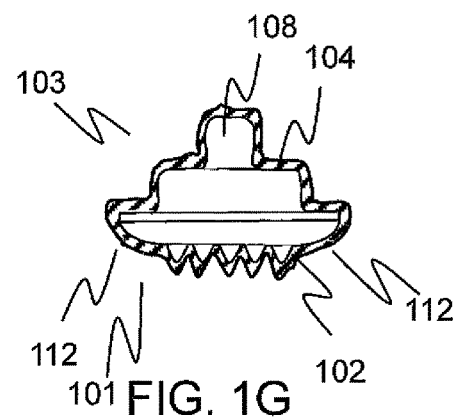
Figure 1H:
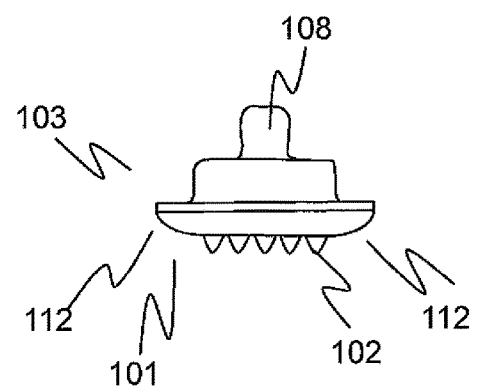

FIGS. 1F, 1G and 1H portray an alternative embodiment of the monolithic physiological recording device wherein the device is reduced in size in a single axis, flattening the sides of the otherwise elliptical or circular device. Such embodiments may be more useful for attachment to or integration into garments, harnesses, or other wearables to be placed on a subject's body. FIG. 1F depicts a bottom view of such alternative embodiment. The lower surface 101 still comprises surface features 102; however, the radius of the device has been reduced in one axis to make the device narrower. FIGS. 1G and 1H depict this alternative embodiment from a cross-section view and side view, respectively. Both show the connector 108 on the upper surface, and the surface features 102 on the lower surface 101 of the device. FIG. 1G further depicts the conductive coating and/or ionic compound 104 which preferably is applied to the nonconductive device in order to facilitate the redox reaction and transmit biopotential or physiological signals from the subject's body to the connector 108. FIG. 1H does not show this coating in order to more clearly show the other features. In such alternative embodiments, the reduction in size in one axis necessarily decreases the distance of curvature of the encouragement lip in that axis. However, it is still preferable to have a radius and distance of curvature on the shortened sides to provide stability. Because of the shortened length on those sides, the curved region 112 becomes a beveled edge encouragement lip with a much smaller radius of curvature and distance of curvature, while still providing stability to the device.

FIG. 2 is an illustration of (A) an independent, separate encouragement ring portion of a physiological recording device, (B) a bottom view of the lower surface of a separate dry recording portion, (C) a top view of the upper surface of an assembled dry physiological recording device comprising an encouragement ring portion and an recording portion, (D) a bottom view of the bottom surface of an assembled dry physiological recording device comprising an encouragement ring portion and an recording portion, and (E) a cross section of an assembled dry physiological recording device comprising an encouragement ring portion and an recording portion as well as conductive coating and/or ionic compound. Additionally, FIGS. 2F, 2G, and 2H depict an alternative embodiment wherein the device is decreased in size in one axis. FIG. 2F shows the separate encouragement ring reduces in size, FIG. 2G shows a bottom view of an assembled device with decreased size in one axis, and FIG. 2H shows a side view of an assembled device with decreased size in one axis.

Figure 2A:
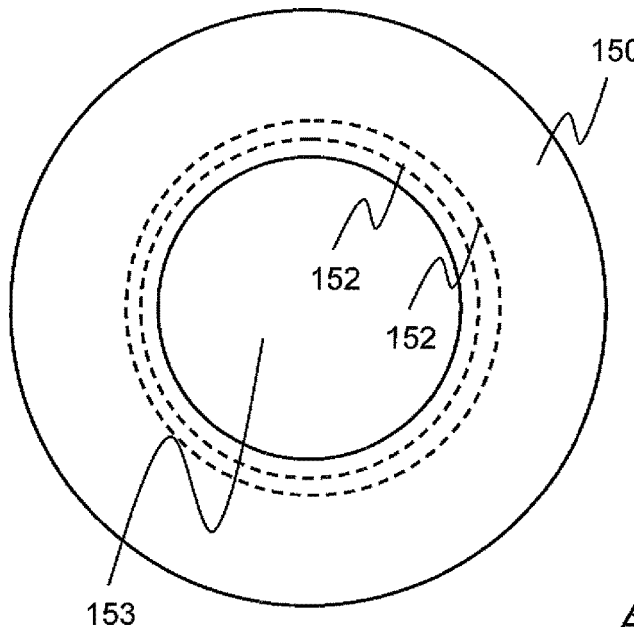
FIG. 2A-H. Illustration of several embodiments of a multi-part dry physiological recording device, including views of such embodiments deconstructed into their various parts, including: (A) an independent, separate encouragement ring portion; (B) a bottom view of a separate dry recording portion; (C) a top view of an assembled dry physiological recording device; (D) a bottom view of an assembled dry physiological recording device; (E) a cross-section of an assembled dry physiological recording device; (F) an alternative reduced size embodiment of a separate encouragement ring portion; (G) a bottom view of an alternative reduced size embodiment of an assembled dry physiological recording device; and (H) a side view of an alternative reduced size embodiment of an assembled dry physiological recording device.
Figure 2C:
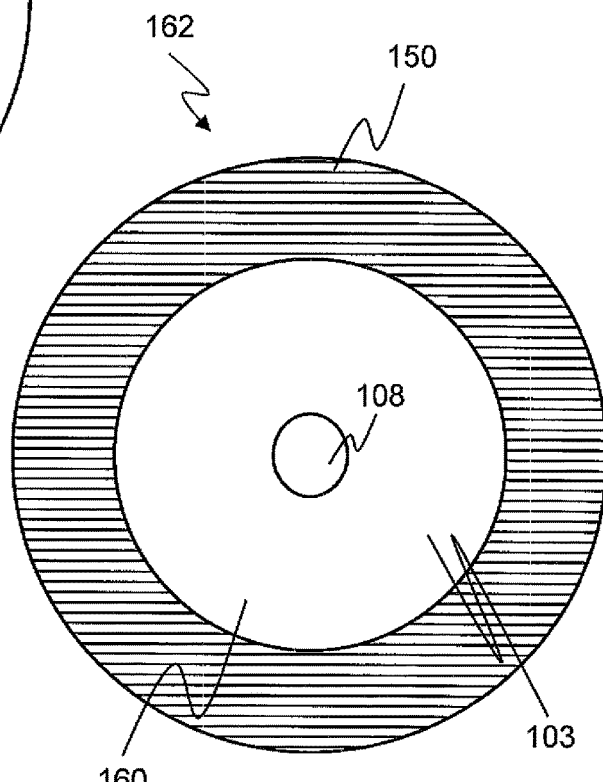
Figure 2B:
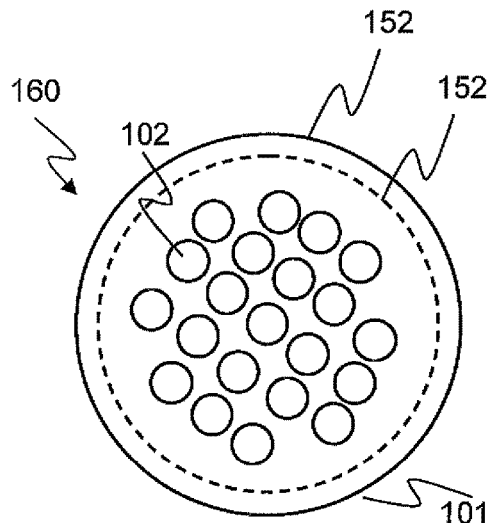

FIG. 2A illustrates an independent, separate encouragement ring portion 150 with a void or opening 153 in its center for connecting the encouragement ring portion 150 to a recording portion (FIG. 2B). Similar to the encouragement lip (not presently show) of the device in a monolithic embodiment (see FIG. 1), the encouragement ring 150 has a lower surface (not shown) that slopes upward, with a radius of curvature and distance of curvature, from its center so as to help stabilize and situate the device against the subject's skin. In the depicted embodiment, threads 152 define the inner edge of the encouragement ring 150 and the outer edge of the void 153 of the encouragement ring portion 150, are used to connect the encouragement ring portion 150 to an recording portion 160 (see FIG. 2B) comprising matching threads 152.

FIG. 2B illustrates a recording portion 160 of a multi-part dry physiological recording device embodiment. The recording portion 160 is preferably connected to the encouragement ring portion 150 (see FIG. 2A) to be placed on a patient or subject and used to record biopotential or physiological signals. As with the monolithic device, the independent recording portion 160 contains surface features 102 on its lower surface for displacing, cracking, or perturbing the skin of a subject. In the depicted embodiment, threads 152 at the outer edge of the independent recording portion 160 match the threads 152 of the independent encouragement ring of FIG. 2A. Although the embodiment of FIGS. 2A and 2B illustrates threads as a method of connecting an independent recording portion 160 and independent encouragement ring portion 150, many other methods are envisioned, such as snap connections, thermal compression, and the like. Preferably, in such embodiments, the recording portion 160 of the device is the only part that comprises any conductive coating and/or ionic compound (not presently shown), such as Ag/AgCl. The separate encouragement ring would receive no such coating, thus minimizing the amount of such coating required to only coat the recording portion 160 either in full or partially.

FIG. 2C shows the upper surface 103 of an assembled physiological recording device 162 comprising a recording portion 160 and encouragement ring portion 150. The connector 108 is located about the center of the upper surface 103 of the recording portion 160 and the encouragement ring portion 150 surrounds and holds the recording portion 160. The recording portion 160 is preferably coated with a layer of conductive coating and/or ionic compound (not presently shown), such as Ag/AgCl, while the encouragement ring portion 150 has no such coating.

Figure 2D:
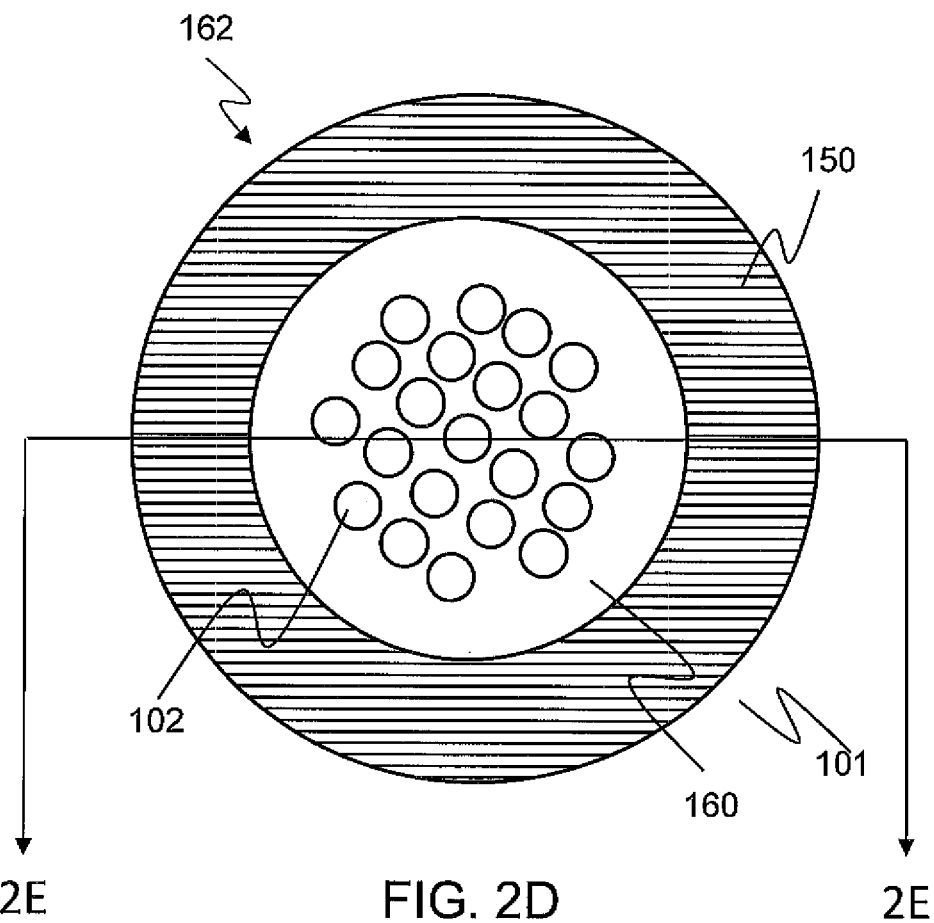

FIG. 2D illustrates the lower surface 101 of an assembled physiological recording device 162 comprising an encouragement ring portion 150 and a recording portion 160. Surface features 102, as previously described, are shown in the on the lower surface 101 of the recording portion 160, with the encouragement ring 150 again shown surrounding and holding the recording portion 160. Again, preferably only the recording portion 160 receives a conductive coating and/or ionic compound (not presently shown) while the encouragement ring portion 150 does not get any such coating.

Figure 2E:
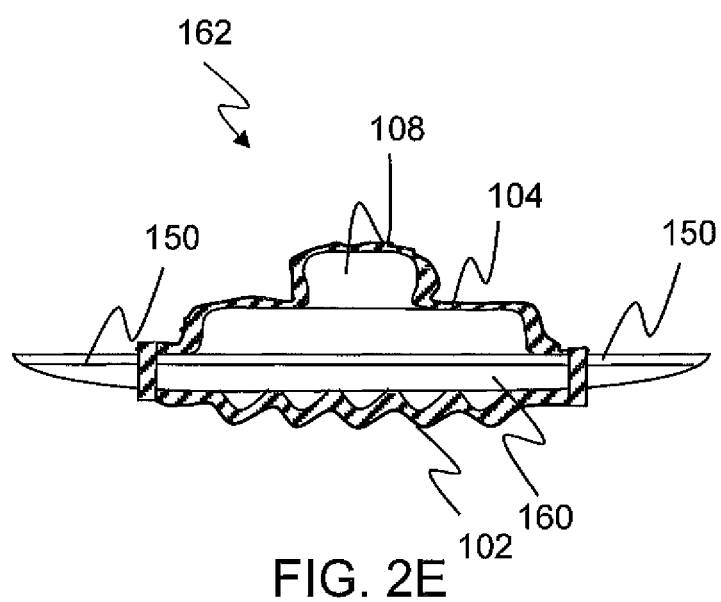

FIG. 2E illustrates a cross section of an assembled multi-part physiological recording device 162 comprising a recording portion 160, an encouragement ring portion 150, and a conductive coating and/or ionic compound 104, depicted by the hatched area. Surface features 102 are again shown on the lower surface of the recording portion 160 and a connector 108 is again shown on the upper surface of the recording portion 160. In the depicted embodiment, the recording portion 160 is made from a nonconductive plastic, and therefore, it is covered with a conductive coating and/or ionic compound 104 (e.g., Ag/AgCl) to help create a redox reaction, and to decrease electrical impedance and facilitate the transmission of biopotentials or physiological signals from the patient to the monitoring equipment (not shown). As shown, preferably only the recording portion 160 is coated in the conductive coating and/or ionic compound 104, and thus such coating traverses the connection points where the recording portion 160 meets and is attached to the encouragement ring portion 150. Because the conductive coating and/or ionic compound 140 is applied separately to only the recording portion 160, the encouragement ring 150 does not actually receive any coating. Lastly, the encouragement ring portion 150 is shown surrounding and holding the recording portion 160 and sloping upward from the lower surface of the device 162. The radius and distance of curvature define the distance over which the encouragement ring 150 curves upward away from the surface features 102 toward the outer edge of the device 162.

Figure 2F:
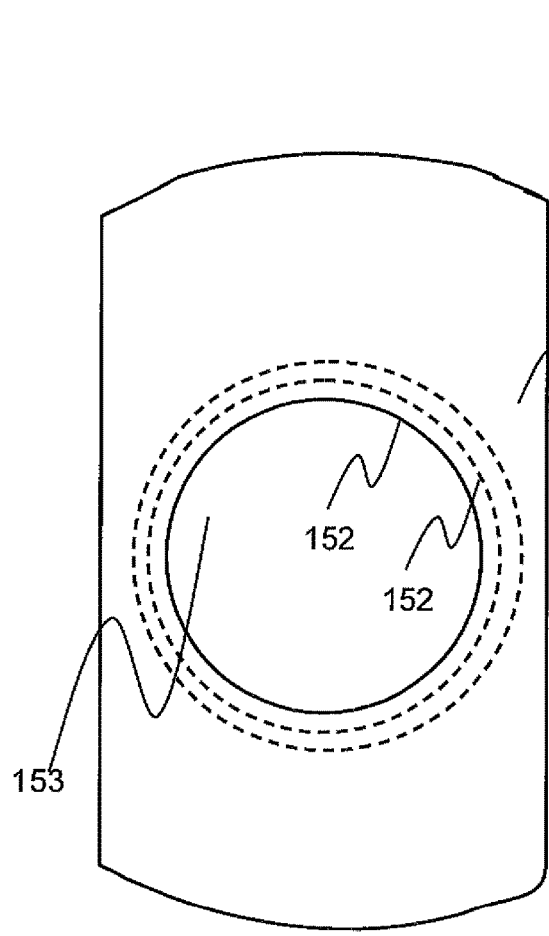
Figure 2G:
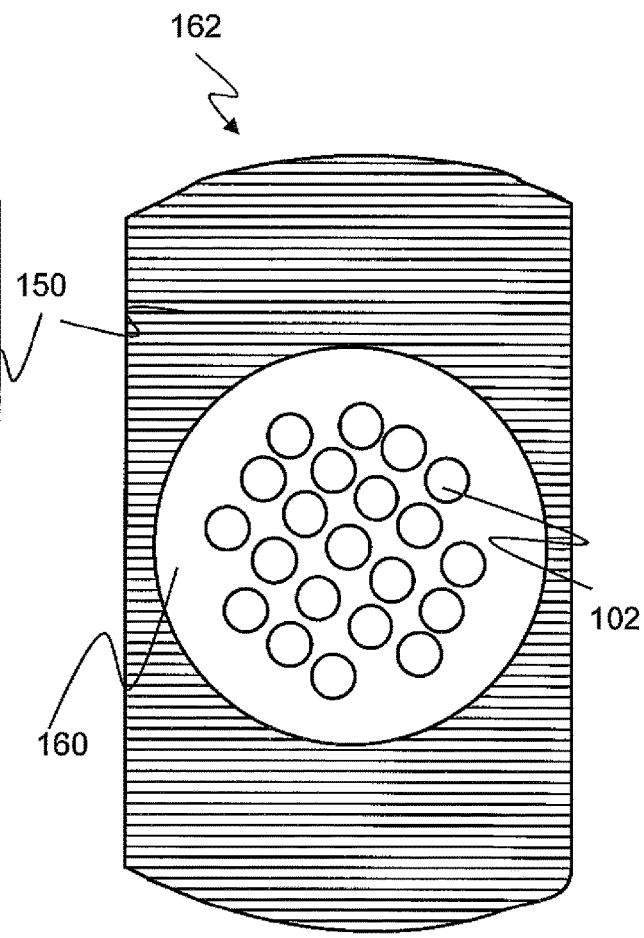
Figure 2H:
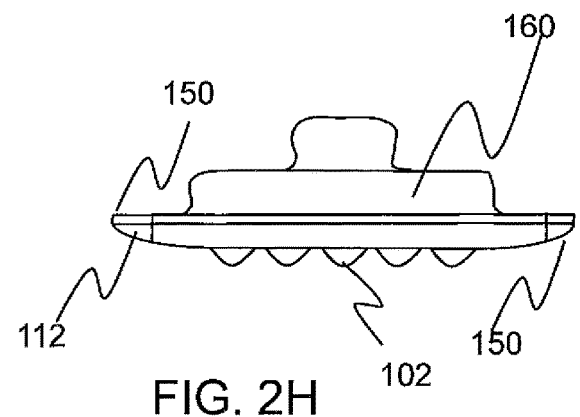

FIGS. 2F, 2G, and 2H depict an alternative embodiment wherein the size of the device is reduced in a single axis. FIG. 2F depicts an encouragement ring portion 150 for such an embodiment where the encouragement ring 150 is decreased in size to come closer to the void or opening 153 into which the recording portion 160 will be placed. FIG. 2G depicts the assembled multi-part physiological recording device with the recording portion 160 placed into the void or opening 153 of the encouragement ring portion 150. Again, the size of the device is reduced in a single axis to make the device smaller and potentially better suited for placement into garments, harnesses, or other wearables to be worn by the subject. FIG. 2H depicts a cross section of the reduced-size embodiment of the device. The recording portion 160 is in the center, surrounded by the encouragement ring portion 150. However, rather than the previously described encouragement ring's radius of curvature and distance of curvature around the entire encouragement ring, the reduced-size embodiment has multiple such radii and distances. The radius of curvature and distance of curvature in the decreased axis are much smaller, and the curved portion effectively is a beveled edge encouragement lip 112.

FIG. 3 illustrates a cross section of an alternative embodiment of a multi-part physiological recording device. In this embodiment, a compression fitting is used to attach the recording portion 198 and the encouragement ring portion 200. The recording portion 198 preferably contains a ridge 202 around the circumference of its outer edge. An encouragement ring portion 200 preferably contains a matching depression around the void or opening at its center. This particular embodiment envisions that the encouragement ring portion 200 is preferably made of a material, that when heated, will expand around the ridge 202 of the recording portion 198. The encouragement ring portion 200 can thus be placed around the ridge 202 of the recording portion 198, and as the encouragement ring portion 200 cools, it will preferably contract around the ridge 202 of the recording portion 198 creating a tight fit. As described above, the electrode is preferably covered in a conductive coating and/or ionic compound 104 to create the redox reaction, and to decrease electrical impedance and facilitate the transmission of biopotentials or physiological signals from the subject to the monitoring equipment (not shown). Therefore, it is important that the contraction of the encouragement ring 200 does not destroy or sever the contiguous conductive coating and/or ionic compound 104 which would prevent or diminish the electrical pathway between the connector (not shown) and the surface features 102 of the recording portion 198.

FIGS. 4 and 5 illustrate a cross section of an assembled multi-part physiological recording device. In embodiments shown in both FIG. 4 and FIG. 5, the encouragement ring portion 150 is again attached to, thus surrounding and holding, a recording portion 160, 170 covered with a conductive coating and/or ionic compound 104 as previously described. Again, preferably only the recording portion 160, 170 is covered in the conductive coating or ionic compound 104, and the encouragement ring 150 is not covered. Surface features 102 are also shown on the lower surface of the recording portion 160 and 170 as previously described. Both embodiments further comprise an adhesive collar 250 surrounding the electrode and attached to the upper surface of the device, particularly the upper surface of the encouragement ring portion 150. The adhesive collar 250 extends beyond the outer edge of the encouragement ring portion 150 such that it may be attached to a subject's skin and hold the assembled device in place on a subject's body. In the embodiment shown in FIG. 4, the recording portion 160 is manufactured so as to comprise an integrated connector 108 as part of the upper surface of the recording portion 160. The embodiment of FIG. 5, however, does not comprise an integrated connector manufactured as part of the recording portion, but rather the separate metal connector portion (not shown) is a separate piece which may be assembled to the separate recording portion 170 using threads, snaps, or similar methods. The particular depicted embodiment comprises a snap fitting whereby the separate metal connector portion (not shown) would be placed on top of the separate recording portion 170, and pressure applied forcing the nesting connecting ring 304, fit into a matching depression or cavity (not shown) on the separate connector portion (not shown). Alternatively, the separate metal connector portion may be constructed not of metal, but of conductive plastic, such as carbon. Such embodiments are envisioned to help keep manufacturing costs low by decreasing the amount of the device constructed of expensive materials, and minimizing the amount of conductive coating and/or ionic compound required.

Figure 6A:
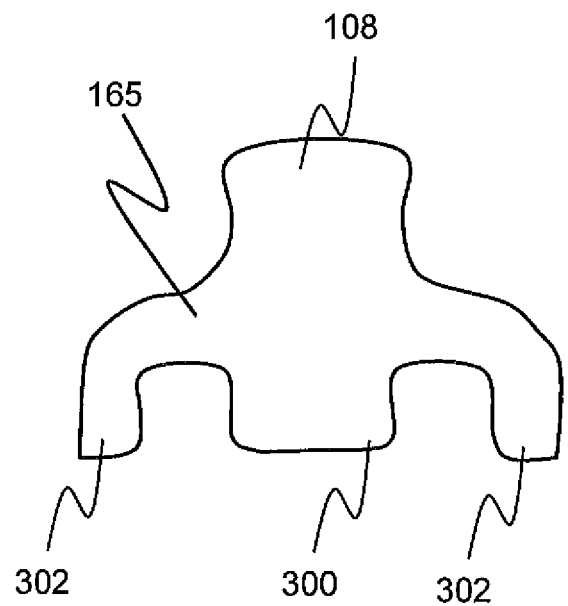
FIG. 6A-B. Cross section of another embodiment of a multi-part dry physiological recording device comprising separate (A) metal connector portion, and (B) recording portion.
Figure 6B:
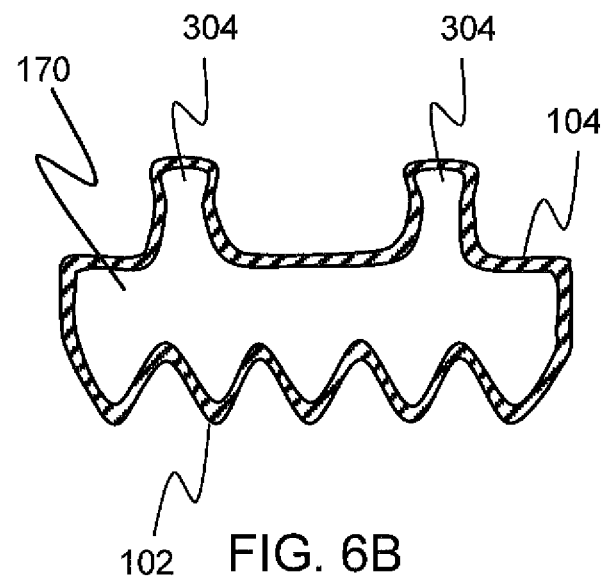

FIG. 6 illustrates a cross-section of the physiological recording device embodiment of FIG. 5 wherein the recording portion comprises two separate pieces: the separate recording portion 170 and a separate metal connector portion 165. FIG. 6A shows an independent metal connector portion 165 comprising the connector 108, an outer ring 302, and an inner ring 300. FIG. 6B shows the separate recording portion 170 comprising surface features 102 and a nesting connecting ring 304 slightly larger in diameter than the inner ring 300 of the connector portion 165, but slightly smaller in diameter than the outer ring 302 of the connector portion 165. Preferably, the separate recording portion 170 of FIG. 6b can be snapped to the connector portion 165 of FIG. 6A by applying pressure and forcing the nesting connecting ring 304 of the separate recording portion 170 between the inner ring 300 and outer ring 302 of the connector portion 165, thereby creating a tight fit such that significant force is required to separate the two pieces. The separate metal connector portion 165 is preferably constructed out of metal, or has a thin metal coating, which reduces or eliminates the need for an expensive conductive coating and/or ionic compound 104 such as Ag/AgCl. The separate recording portion 170 has the conductive coating and/or ionic compound 104, and thus creates the redox reaction and drives the transfer of biopotential or physiological signal from the subject, up to the separate metal connector portion 165, and then to the monitoring equipment (not shown). Reducing the coverage of the expensive conductive coating and/or ionic compound 104 helps keeps the costs of the device low.

Figure 7:
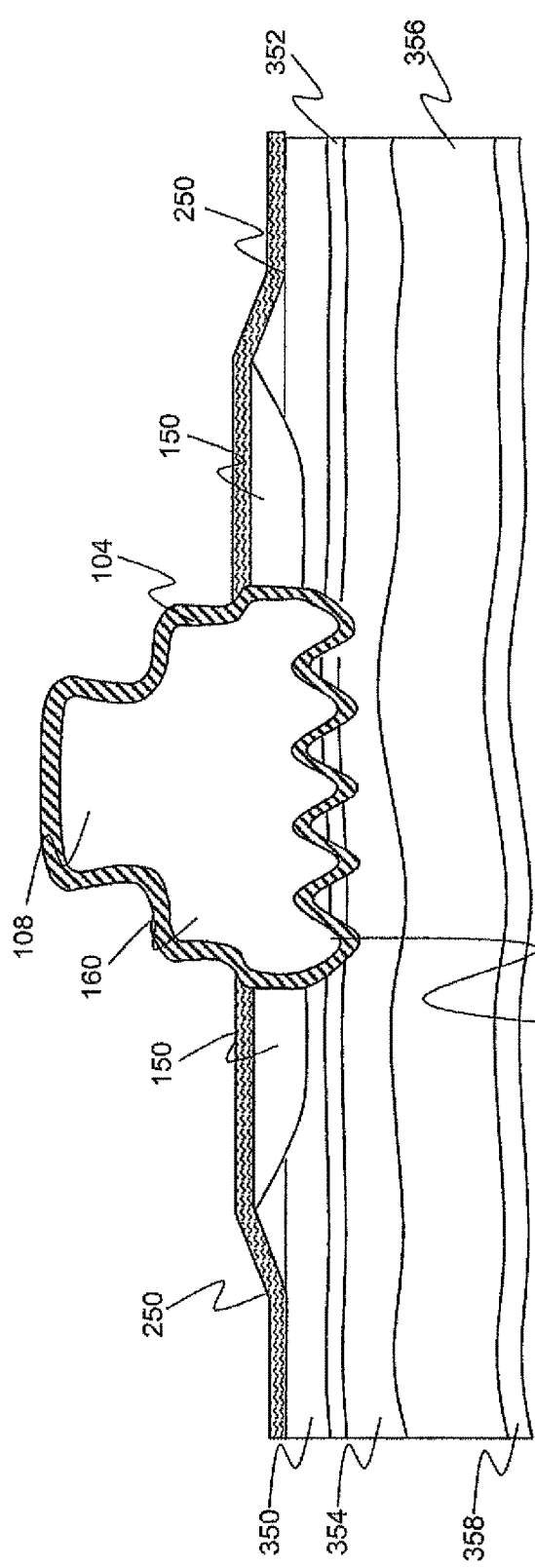
FIG. 7. Cross section of an assembled multi-part dry physiological recording device with adhesive and conductive and/or ionic compound attached to a subject's skin, showing the surface features of the device connecting to lower layers of the subject's skin.

FIG. 7 illustrates a cross section of an assembled multi-part dry physiological recording device comprising an recording portion 160, encouragement ring portion 150, and an adhesive collar 250, attached to subject's skin 350, 352, 354, 356, 358. The particular embodiment depicts the surface features 102 penetrating the outer layers of the subject's skin, but such penetration is not required. In fact, preferably, the surface features 102 merely crack or perturb the skin without penetrating. The recording portion 160 is covered in a conductive coating and/or ionic compound 104 and attached to an encouragement ring portion 150 as described throughout the application. The adhesive collar 250 is preferably capable of attaching to a subject's skin and substantially holding the assembled device in place as its surface features 102 connect the device to the subject's skin. In the particularly depicted embodiment of FIG. 7, the adhesive collar 250 sits on the upper surface of the encouragement ring portion 150 and is attached to the stratum corneum 350, or outermost layer of the skin, which is depressed by the encouragement ring 150. Due to the adhesive collar 250 force holding the assembled device to the skin, and the depression of the stratum corneum 350 by the encouragement ring portion 150, the surface features 102 of the assembled device are able to displace, perturb, or crack the stratum corneum 350, the stratum lucidum 352, and at least into the stratum granulosum 354. In this depiction, the stratum spinosum 356 and stratum basale 358 are shown beneath the stratum granulosum 354. As previously mentioned, such penetration is not required, nor necessarily preferred, but rather is one option for accessing and accurately recording and transmitting biopotentials or physiological signals from the subject, through or around the device to the connector 108, and to the monitoring equipment (not shown).

Figure 8:
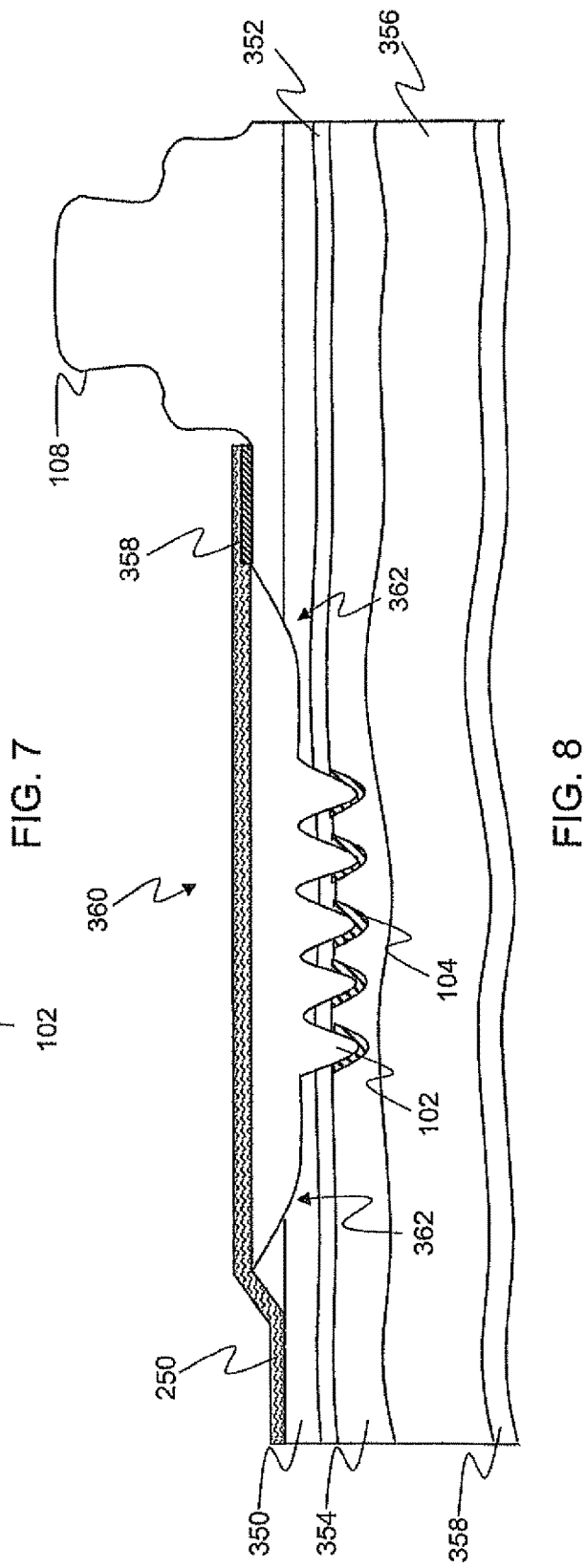
FIG. 8. Cross section of a stamped monolithic dry physiological recording device comprising an encouragement lip, surface features, snap connector, and conductive and/or ionic compound, with adhesive attached to a subject's skin where the surface features of the device connect to lower layers of a subject's skin.

FIG. 8 illustrates a cross section of a stamped metal monolithic device 360 comprising an encouragement lip 362, surface features 102 on the lower surface of the device, connector 108, adhesive collar 250, and silver/silver chloride puck 340, attached to a subject's skin where the surface features 102 connect the device to the outer layers of a subject's skin. In the particularly depicted embodiment of FIG. 8, the entire stamped metal device 360 is made from a stamped metal such as aluminum, steel, tin, lead or the like which is strong enough to resist a change in shape by forces exerted by a subject's skin as surface features 102 of the electrode displace, crack, or perturb the skin and are held in place by the adhesive collar 250. Additionally, the metal should be electrically conductive so as to allow monitoring equipment (not shown) connected to the electrode via the connector 108 to measure biopotentials from the subject. An Ag/AgCl puck 340 is preferably in the electrical pathway, and located on the surface of the stamped metal electrode 360 between the top of the encouragement lip 362 and the connector 1080 in order to decrease impedance and facilitate redox reaction with the ions within the skin. The use of a conductive metal as a base material and a small Ag/AgCl puck prevents the need for coating the entire device in Ag/AgCl as shown in other embodiments of the present invention, and thus reduces the cost of the device. As before, the stratum corneum 350 is preferably depressed by the encouragement lip 362 and the surface features 102 displace, crack, or perturb the stratum corneum 350, stratum lucidum 352, and at least into the stratum granulosum 354. The stratum spinosum 356 and stratum basale 358 are shown below the stratum granulosum 354. Again, the penetration shown in this embodiment is not necessary, or even preferred, as it may be more preferable to merely crack or perturb the skin without penetration. The location of the connector 108 next to the surface features 102 and encouragement lip 362, rather than above them, facilitates the stamped metal manufacturing process as well as provides for strain relief for the surface features 102 from any lead connector (not shown) attached to the connector 108. As the weight from a lead connector attached to the connector 108 pulls on the connector 108, it will not provide the direct force away from the surface of the skin as would normally occur in an embodiment where the connector is directly above and in-line with the surface of the device in contact with the patient's skin. Instead, the offset connector disperses some of the forces pulling the device away from the surface of the skin, and provides a degree of strain relief which helps the device remain more securely attached to the subject for a longer period of time. Further, just the tips or ends of the surface features 102 may be covered in conductive coating and/or ionic compound 104. As described throughout the application, this coating or compound creates a redox reaction which helps reduce the electrical impedance and drive the transmission of biopotentials or physiological signals from the subject to monitoring equipment (not shown). By providing a metallic, conductive device 360, and coating only the tips or ends of the surface features 102 with conductive coating and/or ionic compound 104, the cost of the device is minimized my minimizing the amount of expensive coating 104 such as Ag/AgCl required.

Figure 9:
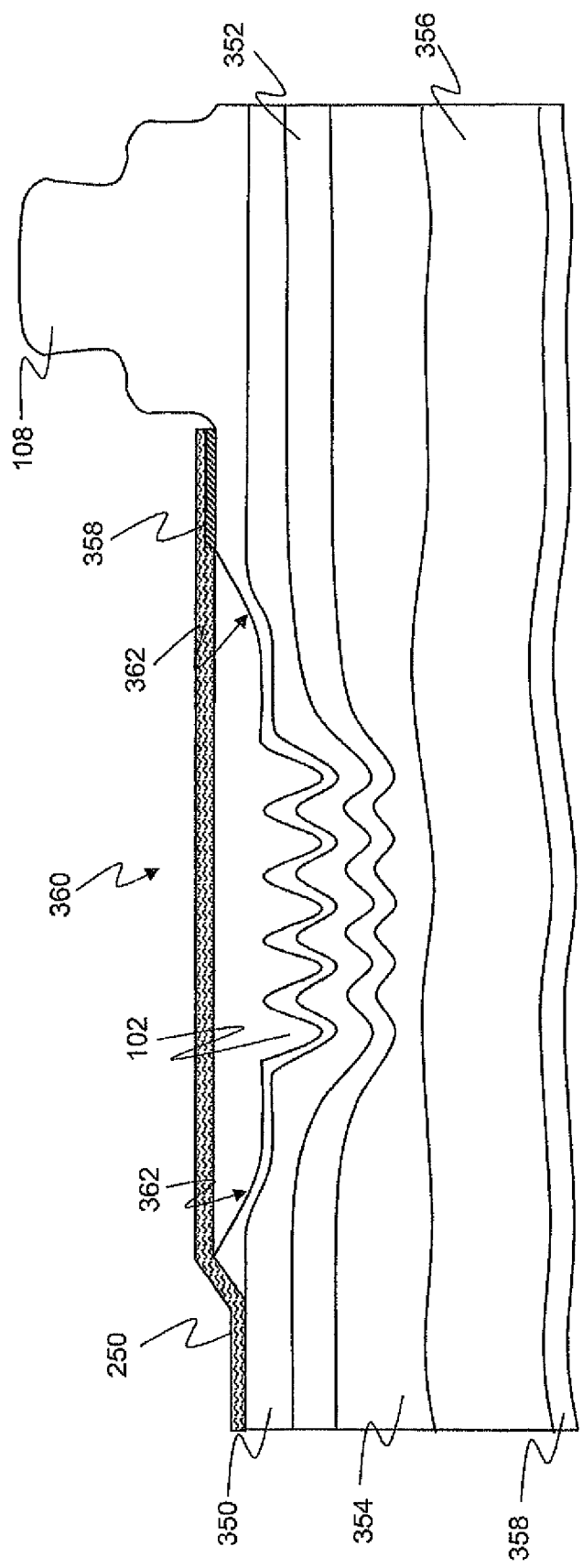
FIG. 9. Cross section of a stamped monolithic dry physiological recording device comprising an encouragement lip, surface features, snap connector, and conductive and/or ionic puck situated away from the subject's skin, with adhesive attached to a subject's skin where the surface features of the device depress but do not fully penetrate a subject's skin while connecting to the lower layer(s).

FIG. 9 illustrates a cross section of the same embodiment of a stamped metal physiological recording device of FIG. 8, but wherein the surface features 102 portray the optional function of depressing, and thus displacing, cracking, or perturbing the skin, without actually penetrating through the outermost layer(s). In this embodiment, the adhesive 250 holds the stamped metal device 360 to the stratum corneum 350, and the encouragement lip 362 and surface features 102 merely depress, and thus displace, crack, or perturb the stratum corneum 350. The stratum granulosum 352, stratum spinosum 354, and stratum basale 354, show similar perturbations; however, with decreasing severity as distance from the stratum corneum 350 increases. An Ag/AgCl puck 340 is shown, as in FIG. 8, and serves to create the redox reaction that drives transmission of the biopotential or physiological signals. Optionally, a conductive coating and/or ionic compound may be included on the device, or more preferably just on the surface features 102, or just the tips or ends of the surface features 102, as described with respect to FIG. 8; however, no such coating or compound is depicted in this figure to more clearly show the desired function of depressing without penetrating the skin by the surface features 102.

FIG. 10 illustrates various embodiments of a cross-section of another embodiment of a stamped metal monolithic physiological recording device comprising an encouragement lip 366, surface features 102, and a connector 108, all similar to the embodiment depicted in FIG. 8. FIG. 10a further comprises an Ag/AgCl puck 340, also similar to FIG. 8. However, the particular embodiment depicted in FIG. 10A comprises a folding stamped metal device wherein the device as manufactured provides a pivot or folding point 365. This folding point 365 allows for the connector portion 363 to be folded over and become oriented above the recording portion 361 which is placed in contact with the subject's or patient's skin. This is merely another embodiment in which a manner of strain relief is provided, similar to the embodiments in FIGS. 8 and 9, wherein forces tending to pull the recording portion away from the subject's skin, are diverted or decreased, thus allowing the recording portion to remain more securely contacting the subject. Further, just the tips or ends of the surface features 102 may be covered in conductive coating and/or ionic compound 104. As described throughout the application, this coating or compound creates a redox reaction which helps reduce the electrical impedance and drive the transmission of biopotentials or physiological signals from the subject to monitoring equipment (not shown). By providing a metallic, conductive device 360, and coating only the tips or ends of the surface features 102 with conductive coating and/or ionic compound 104, the cost of the device is minimized my minimizing the amount of expensive coating 104 such as Ag/AgCl required.

FIG. 10B depicts an embodiment virtually identical to that in FIG. 10A; however there is no Ag/AgCl puck, but rather only the conductive coating and/or ionic compound 104 is provided on the tips or ends of the surface features 102.

Figure 10C:
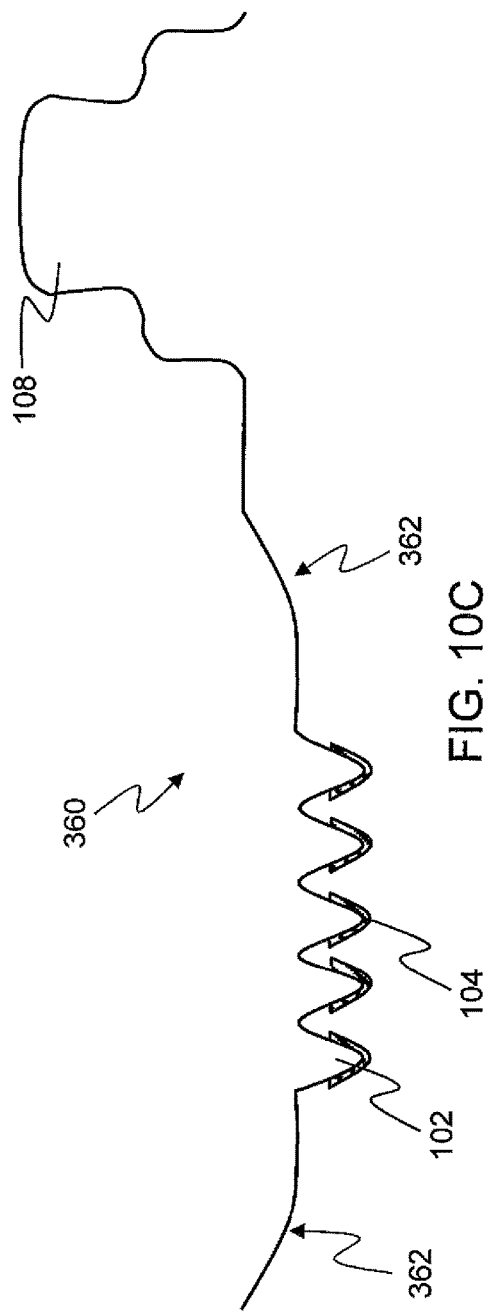

FIG. 10C is another depiction of the physiological recording device of FIGS. 8 and 9. Again, the connector 108 is offset from above the surface features 102 to provide strain relief. The encouragement lip 362 helps to situate, stabilize, and secure the device 360 down onto the subject's skin. In this particular embodiment though, there is no Ag/AgCl puck included, and thus the conductive coating and/or ionic compound 104 provided on the surface features 102 is all such coating or compound used to drive the transmission of signals as described throughout the application. And again, just the tips or ends of the surface features 102 may be covered in conductive coating and/or ionic compound 104. As described throughout the application, this coating or compound creates a redox reaction which helps reduce the electrical impedance and drive the transmission of biopotentials or physiological signals from the subject to monitoring equipment (not shown). By providing a metallic, conductive device 360, and coating only the tips or ends of the surface features 102 with conductive coating and/or ionic compound 104, the cost of the device is minimized my minimizing the amount of expensive coating 104 such as Ag/AgCl required.

Figure 11:
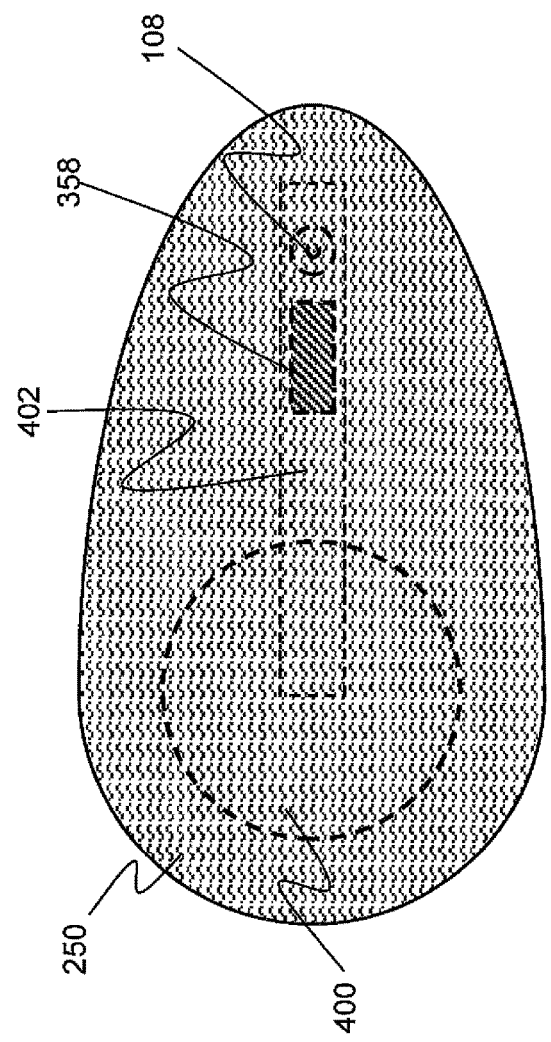
FIG. 11. Top view of another embodiment of a dry physiological recording device whereby the snap connector is offset from the placement of the portion of the device which contacts the subject's skin, wherein the device comprises a recording portion, conductive strip, conductive and/or ionic compound, snap connector, and adhesive.

FIG. 11 illustrates another embodiment of the present invention wherein the connector 108 is offset from directly above and in-line with the recording portion 400, thus providing strain relief as described above. In the present embodiment, a recording portion 400 is connected to a connector 108 via a conductive strip 402. The dry electrode 400 may be made of any variety described herein (e.g., metal, plastic, and the like). The conductive strip 402 acts to provide an electrical pathway between the dry electrode 400 and the connector 108 which may be attached to lead connectors (not shown) and devices (not shown) used for measuring biopotentials. The location of the snap connector 108 a distance away from the electrode 400 acts as strain relief decreasing the likelihood of the device being pulled or separated from the subject's skin. An Ag/AgCl puck 340 located on the conductive strip, in series with the dry electrode 400 and snap connector 108, acts to decrease impedance and facilitate a redox reaction with ions within the skin as previously described. Finally, the entire assembly (recording portion 400, conductive strip 402, Ag/AgCl puck 340) is preferably covered by an adhesive collar 250 used to attach the physiological recording device to a subject's skin. The connector 108 may protrude through the adhesive collar 250, or may alternatively be contained beneath it thus holding the lead connector (not shown) with the adhesive, or other similar arrangements.

FIG. 12 illustrates an embodiment comprising a rivet connector 450 on (A) a stamped metal device with surface features 102 and Ag/AgCl puck 340, (B) a plastic or polymer device 454 covered in a conductive coating and/or ionic compound 104 with surface features 102, and Ag/AgCl puck 340, (C) a plastic or polymer device 454 with a less expensive metallic or conductive coating 460 and conductive coating and/or ionic compound 104 on the tips or ends of the surface features 102, and (D) a stamped metal device 455 with a conductive coating and/or ionic compound 104 just on the tips or ends of the surface features 102. FIG. 12A illustrates a recording device 455, made of a conductive stamped metal, comprising surface features 102 on the lower surface of the device, an encouragement lip 452 as described throughout, an Ag/AgCl puck 340, and a rivet connector 450. Again, the purpose of the Ag/AgCl puck 340 is to facilitate a redox reaction and decrease impedance between conductive surface features 102 and a lead connector (not shown). This embodiment further shows a conductive coating and/or ionic compound 104 applied to just the tips or ends of the surface features 102. This configuration minimizes the amount of the expensive coating, such as Ag/AgCl required, and thus minimizes the cost of the device, while still providing the coating to create the redox reaction and facilitate the transmission of biopotentials or physiological signals from the subject, through the conductive device. The conductive metal body of the device then provides an electrical pathway by which those signals may be transmitted.

Figure 12A:
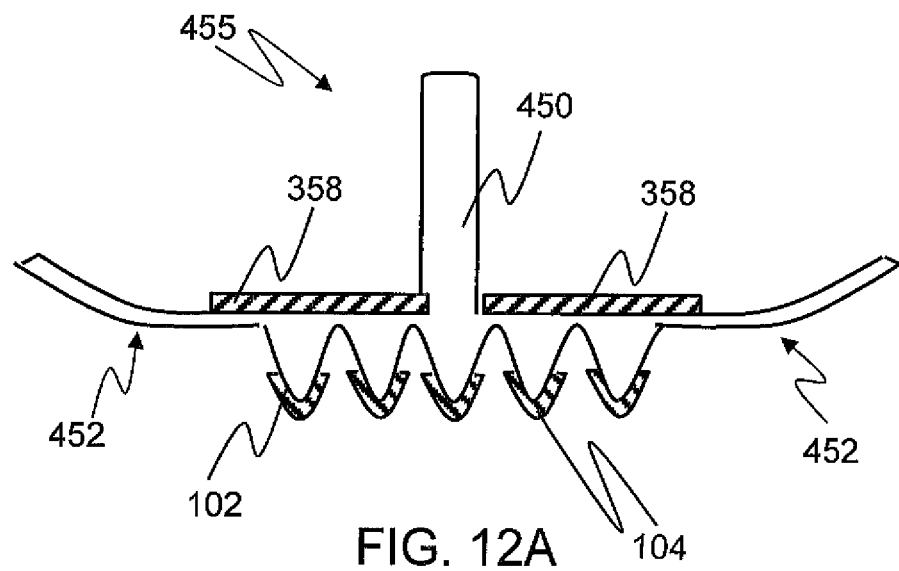
FIG. 12A-D. Cross sections of other embodiments of a dry physiological recording device with a rivet connector, such embodiments including: (A) a recording device made of stamped, conductive metal; (B) a recording device made of a nonconductive material but with a conductive coating and/or ionic compound around the device; (C) another recording device made of nonconductive material and with both an metallic or conductive coating around the device and a conductive coating and/or ionic compound on the surface features; and (D) a recording device made of stamped, conductive metal with a conductive coating and/or ionic compound on the surface features.
Figure 12B:
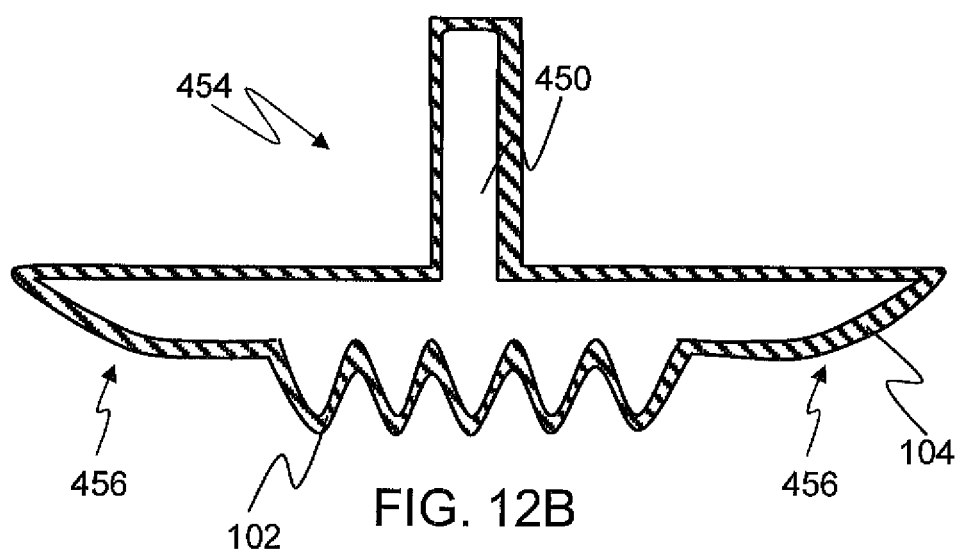

FIG. 12B illustrates a similar device 454 comprising surface features 102 on the lower surface of the device, but made of nonconductive material, such as plastic or polymer, an encouragement 456 lip for helping to situate and stabilize the device on the subject's skin, and a conductive coating and/or ionic compound 104 for facilitating the redox reaction to create a substantially nonpolarized device.

Figure 12C:
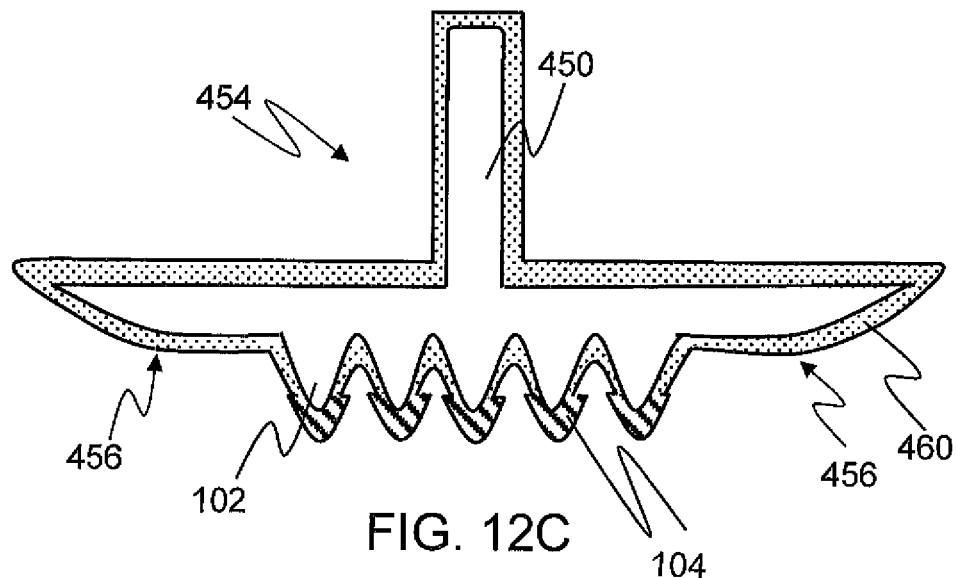

FIG. 12C illustrates another embodiment of a nonconductive plastic or polymer device 454 comprising surface features 102, an encouragement lip 456 for stabilizing and situating the device against the subject's skin, and a rivet connector 450 on the upper surface of the device. However, in the depicted embodiment, the device is not completely coated in the expensive conductive coating and/or ionic compound 104, such as Ag/AgCl, as the embodiment in FIG. 12B, but rather only the tips or ends of the surface features 102 receive this more expensive coating. Instead, the body of the device is completely or mostly covered in a metallic or conductive coating 460 that is much less expensive, yet still allows for electrical transmission of biopotentials or physiological signals. Thus, where the conductive coating and/or ionic compound 104 on the tips or ends of the surface features creates the redox reaction and begins to drive the transmission of biopotentials or physiological signals, the metallic or conductive coating 460 provides an electrical pathway by which those signals may travel from the subject to monitoring equipment (not shown) and costs significantly less than the more expensive conductive coating and/or ionic compound such as Ag/AgCl which coats the tips of the surface features 102. This helps keep the cost of the device low, while still providing functionality in transmitting high quality signals.

Figure 12D:
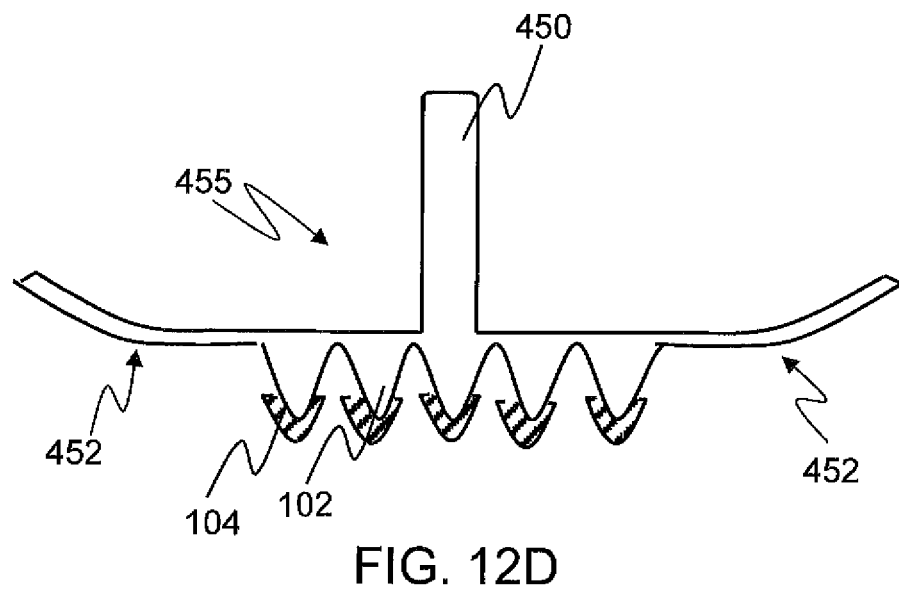

FIG. 12D illustrates another embodiment of a stamped metal physiological recording device 455, wherein the body of the device is constructed or manufactured from a conductive metal. Again, the stamped metal device comprises a rivet connector 450, an encouragement lip 452 as described throughout the application, and surface features 102 on the lower surface of the device. The depicted embodiment further shows a conductive coating and/or ionic compound 104 applied to just the tips or ends of the surface features 102. This configuration minimizes the amount of the expensive coating, such as Ag/AgCl required, and thus minimizes the cost of the device, while still providing the coating to create the redox reaction and facilitate the transmission of biopotentials or physiological signals from the subject, through the conductive device. The conductive metal body of the device then provides an electrical pathway by which those signals may be transmitted.

The embodiments of the dry electrode shown in FIGS. 12A, 12B, 12C, and 12D all comprise a rivet connector 450 protruding from the upper surface of the electrode, above the surface features 102. The purpose of the rivet connector 450 in these figures is to facilitate attachment of the electrode to any wearable (not shown), such as a belt, harness, compression fitting, or any other type of garment, clothing, or the like. By way of a single non-limiting example, the rivet connector electrodes may be attached to a chest strap or arm band and used to measure a subject's heart rate. Attachment with the rivet 450 may be permanent or adjustable, such as with a track system so that the electrode is free to move anywhere on the wearable.

Figure 13A:
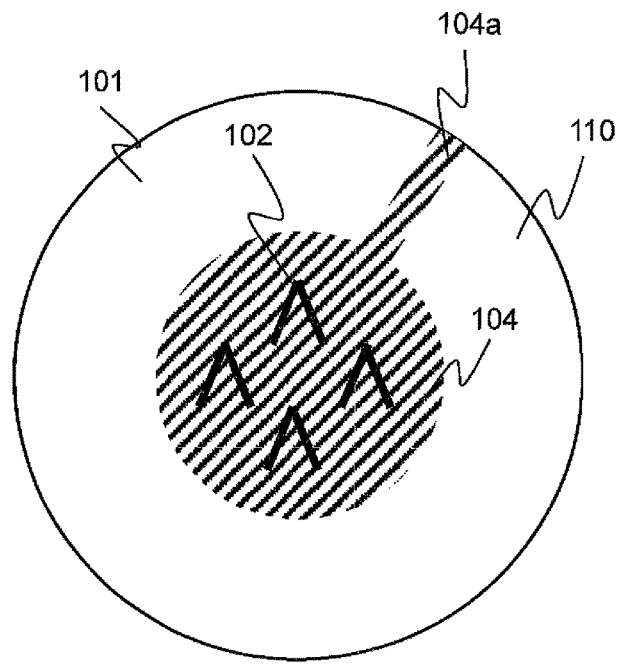
FIG. 13A-C. Illustration of several embodiments of a monolithic dry physiological recording device of the present invention utilizing a minimal amount of conductive coating and/or ionic compound in different patterns requiring less of such coating, such embodiments including: (A) a bottom view depicting a conductive coating and/or ionic compound coating the entirety of the surface features, the area between and immediately outside them, and a conductive or ionic strip; (B) a top view of an alternative embodiment wherein a web or network of conductive coating and/or ionic compound is used to coat the surface features while leaving space between; and (C) a top view depicting the conductive or ionic strip continuing around the edge of the device and to the connector.
Figure 13C:
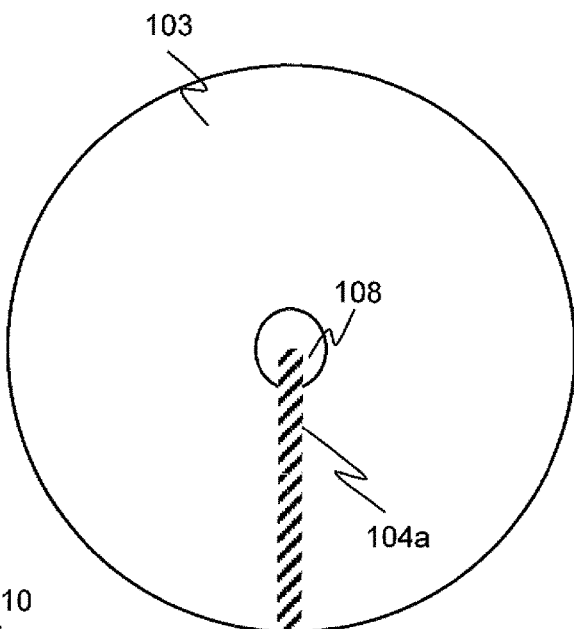
Figure 13B:
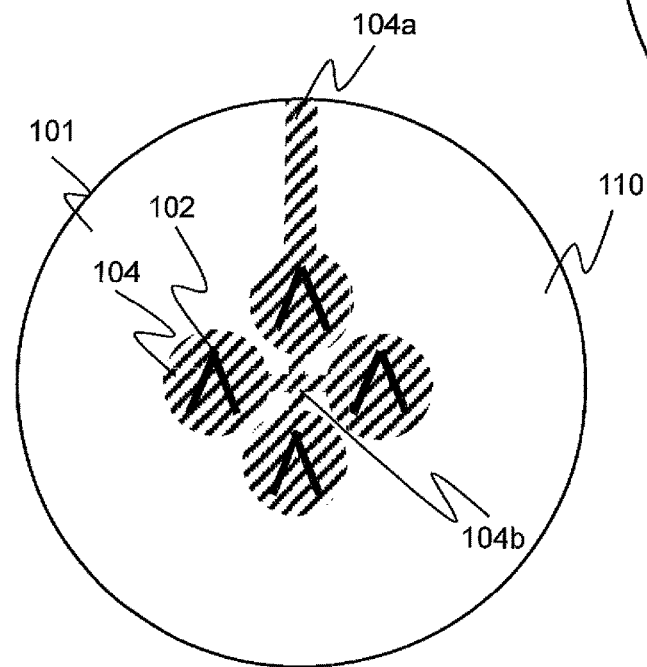

FIG. 13 illustrates several embodiments of a monolithic dry physiological recording device of the present invention whereby the amount of conductive coating and/or ionic compound is minimized. First, FIG. 13A illustrates the lower surface 101 of an embodiment wherein the amount of conductive or ionic compound is reduced by only covering the surface features and the area immediately surrounding them, along with a strip connecting the coated portion of the lower surface to the upper surface. FIG. 13B illustrates the lower surface of another embodiment wherein the amount of conductive coating and/or ionic compound is further minimized by coating the surface features and only a web or network between the surface features, as well as a strip connecting the coated portion of the lower surface to the upper surface. Finally, FIG. 13C depicts the upper surface of the embodiments of FIGS. 13A and 13B, and illustrates the minimized conductive coating and/or ionic compound strip extending from the lower surface to the connector.

FIG. 13A illustrates the lower surface 101 of a polymer or plastic monolithic device comprising a plurality of surface features 102. The conductive coating and/or ionic compound 104 is shown to cover the entirety of the surface features 102, the area between them, and a portion of the lower surface 101 substantially immediately outside the outer radius of the surface features 102. As shown, the area of the lower surface 101 covered by the conductive coating and/or ionic compound 104, is preferably minimized by reducing the radius of the area covered. In the particular embodiment shown, the conductive coating and/or ionic compound 104 is carefully applied to just outside the radius of the surface features, and not extending out to the integrated encouragement lip 110. Preferred coverage of conductive coating and/or ionic compound for such embodiments is described above in great detail. A conductive or ionic strip 104a connects the conductive coating and/or ionic compound 104 on the lower surface 101 to the upper surface 103 as shown in FIG. 13C. The conductive or ionic strip 104a preferably continues without interruption from the conductive coating and/or ionic compound 104 on the lower surface 101 around the edge of the device and across the upper surface 103 to the connector 108 in the middle of the upper surface 103. This continuous conductive coating and/or ionic compound creates a continuous electrical pathway between the surface features 102 on the lower surface 101 and the electrode connector 108 on the upper surface 103, and allows for transmission of the electrical biopotential signals between the patient's or subject's skin (not shown) and the monitoring equipment (not shown). Alternatively, though not shown, the conductive strip 104a may be a different substance from the conductive coating and/or ionic compound 104 that covers the surface features and immediate area surrounding them. For example, a less expensive metallic or conductive coating may be used, similar to embodiments depicted in FIGS. 12C, 14A and 14B. Such alternatives to the depicted embodiment here further decrease the cost of the device by decreasing even further the amount of expensive coating (i.e., Ag/AgCl) required and replacing it with an otherwise conductive, though less expensive substance, and still maintaining the electrical pathway required for transmission of biopotentials or physiological signals.

FIG. 13B illustrates another embodiment for minimizing the conductive coating and/or ionic compound 104 required by coating only the surface features 102 and a web or network 104b between said features, creating a conductive network connecting each of the surface features 102. Because the surface features 102 are each coated individually, they are preferably interconnected with a web or network 104b of the same conductive coating and/or ionic compound material; however, different materials, such as less expensive metallic or conductive coatings, may be used to coat the surface features 102 and interconnect the web or network 104b so long as the materials are electrically conductive. Preferably, where different materials are used, the conductive coating and/or ionic compound 104, such as Ag/AgCl is used to coat at least the tips or ends of the surface features 102, and a different material, such as a metallic or conductive coating that is less expensive, is used to create the conductive web or network 104b between the surface features, and further optionally the conductive strip 104a. Preferably the conductive coating and/or ionic compound 104 is used at least on the tips or ends of the penetrators in order to come in contact with the subject's skin and or fluids, and thus create the redox reaction to reduce electrical impedance and drive transmission of the signals from the subject to the conductive, though less expensive, coating and electrical pathway. As described above, a conductive strip 104a connects the conductive coating and/or ionic compound 104, which comprises the interconnecting web or network 104a between the surface features 102, on the lower surface 101 to the upper surface 103 as shown in FIG. 13C. The conductive strip 104a preferably continues without interruption from the conductive coating and/or ionic compound 104 and 104a on the lower surface 101 around the edge of the device and across the upper surface 103 to the connector 108 in the middle of the upper surface 103. This continuous conductive coating and/or ionic compound creates a continuous electrical pathway between the surface features 102 on the lower surface 101 and the electrode connector 108 on the upper surface 103, and allows for transmission of the electrical biopotential signals between the patient's or subject's skin (not shown) and the monitoring equipment (not shown).

As described above in conjunction with FIGS. 13A and 13B, FIG. 13C illustrates the upper surface 103 of several embodiments of the device comprising a connector 108 and a conductive strip 104a which wraps around the edge of the device and extends along the lower surface 101 to create a continuous conductive pathway for transmitting electrical signals from the patient's or subject's skin (not shown) to the monitoring equipment (not shown).

FIG. 14 illustrates several embodiments of multi-part polymer or plastic physiological recording devices which seek to minimize the cost of the device by minimizing the amount of expensive conductive coating and/or ionic compound, such as Ag/AgCl, used to coat the device. In these embodiments, a secondary metallic or conductive coating, which is significantly less expensive that Ag/AgCl and similar coatings or compounds, to provide an electrical pathway around the non-conductive body of the device.

Figure 14A:
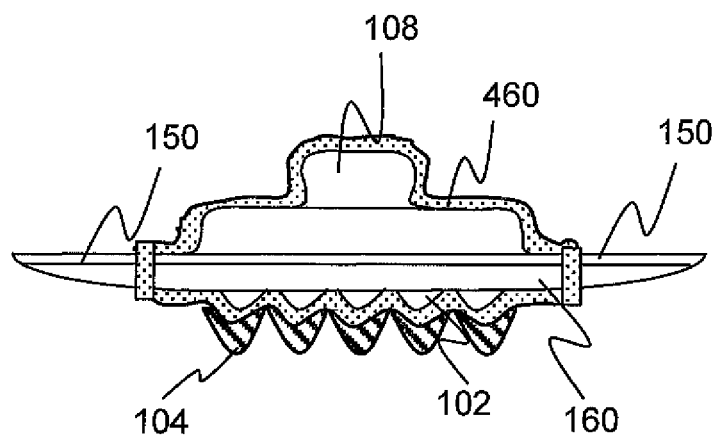
FIG. 14A-B. Cross sections of several embodiments of physiological recording devices which minimize the amount of expensive conductive coating and/or ionic compound by only coating the tips of the surface features, such embodiment including: (A) a multi-part recording device comprising a separate encouragement ring portion and separate recording portion; and (B) monolithic device composed of a single piece.
Figure 14B:
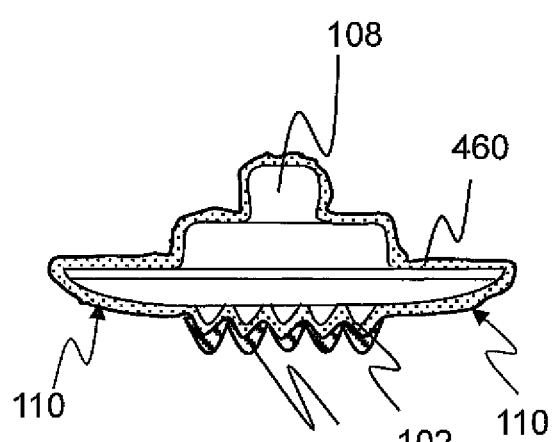

FIG. 14A illustrates a cross-section of a multi-part polymer or plastic physiological recording device comprising a separate encouragement ring 150 and separate recording portion 160. The recording portion 160 is shown attached to or mounted in the separate encouragement ring 150. The recording portion 160 is further shown to comprise surface features 102 for displacing, cracking, or perturbing the subject's skin. The recording portion 160 is further shown to be completely covered by a metallic or conductive coating 460 that is significantly less expensive than the Ag/AgCl coating that is typically used to coat such polymer or plastic electrodes. The separate encouragement ring portion 150 has no coating of either variety as it is less expensive, and more electrically efficient to transmit the biopotentials or physiological signals through the less expensive metallic or conductive coating 460 between the electrode body 160 and the separate encouragement ring 150. The surface features 102 do have such a conductive coating and/or ionic compound 104 (i.e., Ag/AgCl), but it is only covering the tips or ends of the surface features, rather than the whole recording portion 160. This configuration allows the surface features 102 to displace, crack, or perturb the subject's skin in order to access the lower layer(s) of the skin and thus allow the conductive coating and/or ionic compound 104 (i.e., Ag/AgCl) to contact the subject's body fluids, such as blood. The chlorine ions in the subject's fluid interacts with the conductive coating and/or ionic compound 104 to create a redox reaction which significantly decreases the electrical impedance and drives the transmission of biopotentials or physiological signals from the subject to the device. Because the body of the recording portion 160 comprises a non-conductive polymer or plastic, the metallic or conductive coating 460 provides a conductive electrical pathway by which the biopotentials or physiological signals may be transmitted through this coating 460 from the subject to the connector 108, and then through a lead connector (not shown) to the monitoring equipment (not shown). Thus, the expensive conductive coating or ionic compound 104 required to create the redox reaction is minimized, and the electrical pathway is created by the metallic or conductive coating 460 which is significantly less expensive, and the overall cost of the device is greatly decreased while still maintaining, or possibly improving its signal transmitting functionality. FIG. 14B illustrates essentially all of the same features as FIG. 14A; however, the embodiment in FIG. 14B is a monolithic polymer or plastic device, composed of a single piece as opposed to separate electrode and encouragement ring portions. As such, the less expensive metallic or conductive coating 460 covers the entire device body, or at least a path leading from the surface features 102 all the way out the encouragement lip 110 to the edge of the device, and then along the upper surface to the connector 108. Still, only the tips or ends of the surface features 102 receive the more expensive conductive coating and/or ionic compound (i.e., Ag/AgCl) in order to create the redox reaction while minimizing cost.

Figure 15A:
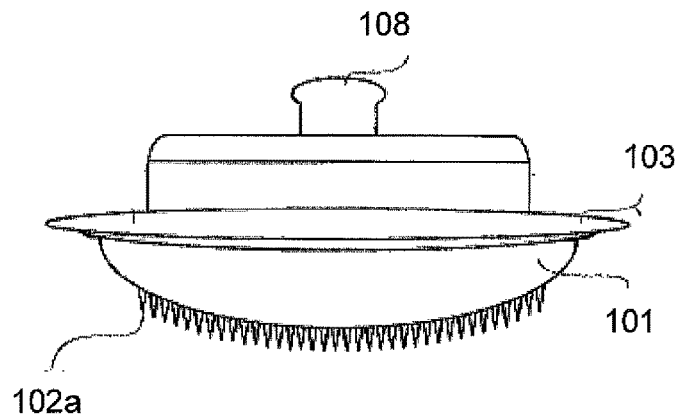
FIG. 15A-D. Depictions of various embodiments of physiological recording devices with varying shapes and configurations of the lower surface of the device, the various embodiments including: (A) a device with a convex lower surface with penetrators each of about the same height; (B) a device with a convex lower surface with penetrators of varying height; (C) a device with a concave lower surface with penetrators each of about the same height; and (D) a device with a concave lower surface with penetrators of varying height.

FIGS. 15A through 15D depict various configurations of surface features and lower surfaces of embodiments of the physiological recording device. FIG. 15A is a side view of a physiological recording device with a convex lower surface 101. The device comprises a both lower 101 and upper 103 surfaces, a connector 108 (depicted as a standard snap type connector, and surface features in the form of penetrators 102a on the lower surface 101 which are needle-like in shape. In the depicted embodiment, each of the penetrators 102a are approximately the same height. The convex nature of the electrode's lower surface 101 may aid in application of the device to an area on a subject that is depressed such as areas near the sternum, armpit and the like. Preferably, penetrators 102a on such a device are of such height that the points of their tips, if connected, would form a curve that is generally parallel to the curvature of the lower surface 101 of the device.

Figure 15B:
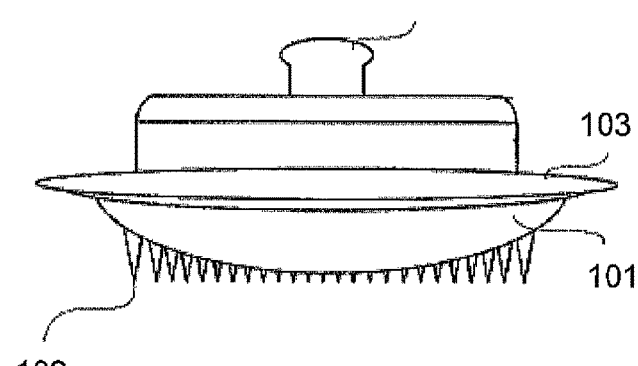

FIG. 15B is a side view of another embodiment of a physiological recording device with a convex lower surface. The device comprises both lower 101 and upper 103 surfaces, and a connector 108 (depicted as a standard snap type connector). The lower surface 101 in the depicted embodiment is convex and is populated with penetrators 102a that are needle-like in shape, and varying in height in proportion to the curvature of the surface so that their tips all are points that if connected would approximate a straight line. The depicted embodiment of the present invention may aid in application to a flat area on the subject's body such as the chest, back, or stomach.

Figure 15C:
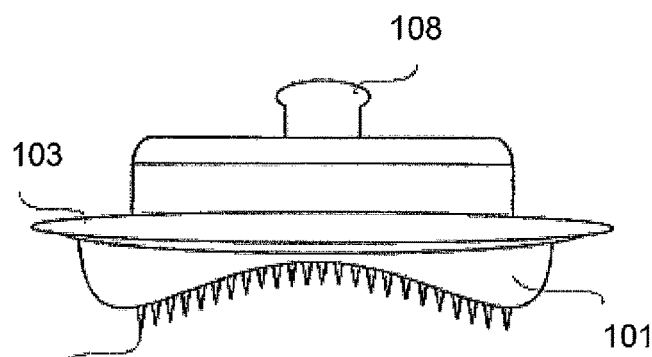

FIG. 15C is a side view of another embodiment of a physiological recording device with a concave lower surface. The device comprises both an upper 103 and a lower surface 101, and a connector 108 (depicted as a standard snap type connector). The lower surface 101 in the depicted embodiment is concave, and is populated with penetrators 102a that are approximately the same height, so that their tips all are points that, if connected, would form a curve that is substantially parallel to the curvature of the lower surface 101. This also may aid in the application of the electrode to a curved or bony area on the subject's body such as a wrist, a finger, ankle, or knee.

Figure 15D:
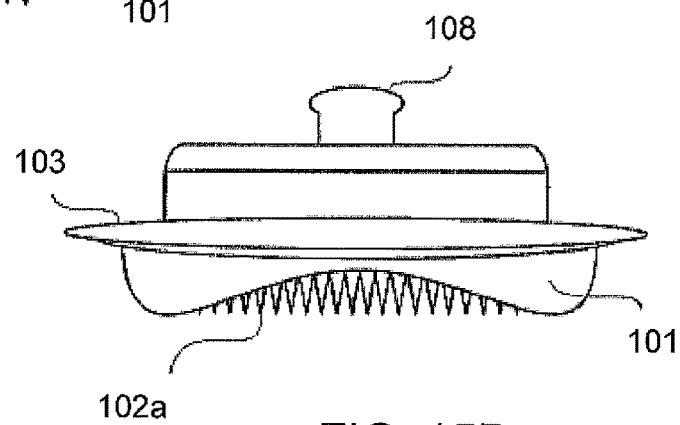

FIG. 15D is a side view of another embodiment of a physiological recording device with a concave lower surface. The device comprises both an upper 103 and a lower surface 101, and a connector 108 (depicted as a standard snap type connector). The lower surface 101 of the depicted embodiment is concave, and is populated with penetrators 102a that are pyramidal in shape and are varying in height in proportion to the curvature of the upper surface 103 so that their tips all are points that if connected would form or approximate a straight line. Such an embodiment may also aid in application to a flat area on the subject's body such as their chest, back, or stomach.

Figure 16A:
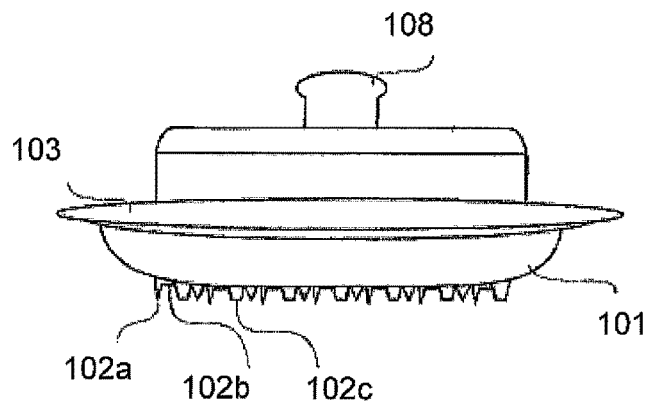
FIG. 16A-D. Depictions of various embodiments of physiological recording devices with varying configurations and types of surface features individually and in combination with each other, such embodiments including: (A) a device with a convex lower surface with penetrators, epidermal stops, and ridges; (B) a device with a convex lower surface with columns; (C) a device with a flat lower surface with penetrators; and (D) a device with a flat lower surface with double penetrators.

FIGS. 16A through 16D illustrate various embodiments of the present invention with different configurations of the lower surface of the device, and alternative forms of surface features in various combinations. FIG. 16A is a side view of another embodiment of a physiological recording device with a convex lower surface. The device comprises an upper 103 and a lower surface 101, and a connector 108 (depicted as a standard snap type connector). The lower surface 101 is convex, and is populated with multiple varieties of surface features including penetrators 102a that are needle-like in shape, ridges 102c with a height slightly lower than the penetrators 102a, and epidermal stops 102b that are significantly shorter than the height than the penetrators 102a. The penetrators 102a readily penetrate the skin, but are limited as to how deep they can penetrate into the skin by both the epidermal stops 102b and the ridges 102c. The ridges 102c further depress the subject's skin allowing for greater surface contact and acting further to limit the depth of penetration of the penetrators 102a. The ridges 102c have a trapezoidal cross section and extend over length (not shown).

Figure 16B:
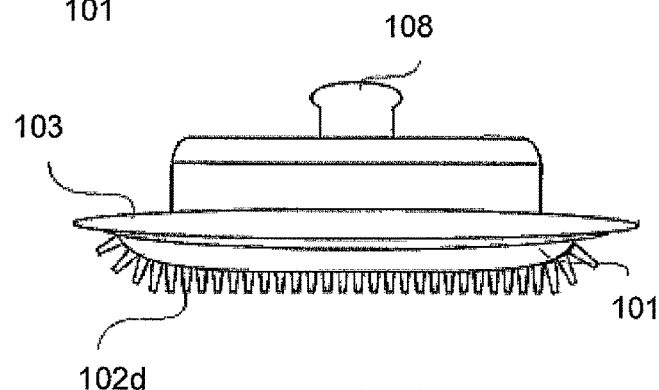

FIG. 16B is a side view of another embodiment of a physiological recording device with a convex lower surface. The device comprises an upper 103 and lower surface 101, and a connector 108 (depicted as a standard snap type connector). The device has a convex lower surface 101 populated surface features in the form of columns 102d that are each approximately the same height, and have a slightly tapered edge. The columns 102d depress the subject's skin increasing the surface area of the lower surface 101 of the device in contact with the subject's skin, but may not penetrate the skin.

Figure 16C:
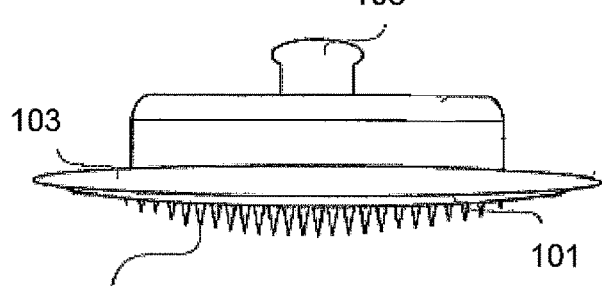

FIG. 16C is a side view of another embodiment of a physiological recording device with a flat lower surface. The device comprises an upper 103 and a lower 101 surface, and a connector 108 (depicted as a standard snap type connector). The device has a flat lower surface 101 populated with surface features in the form of penetrators 102a that are pyramidal in shape and vary in height to form a dome-like shape of penetrator 102a tips.

Figure 16D:
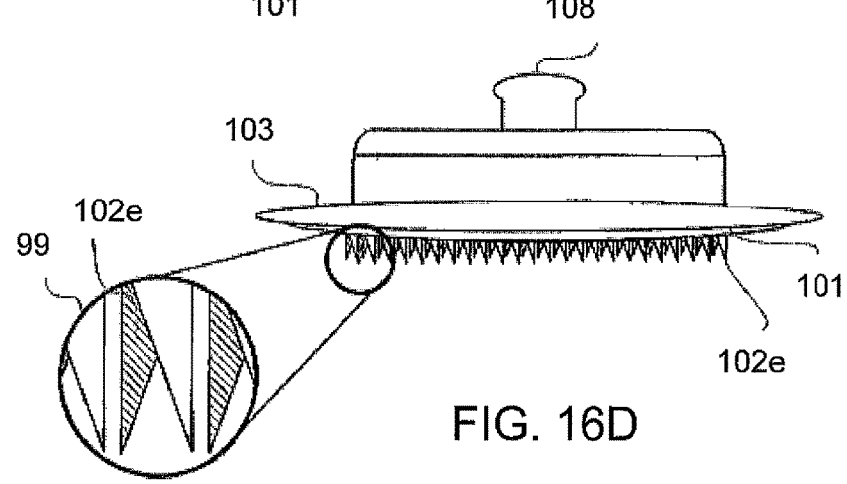

FIG. 16D is a side view of another embodiment of a physiological recording device with a flat lower surface. The device comprises an upper 103 and a lower 101 and a connector 108 (depicted as a standard snap type connector 108). The device has a flat lower surface 101 populated with surface features in the form of thatch-like or double penetrators 102e. The call out 99 shows in greater detail the features of the thatch-like or double penetrators 102e.

Figure 17A:
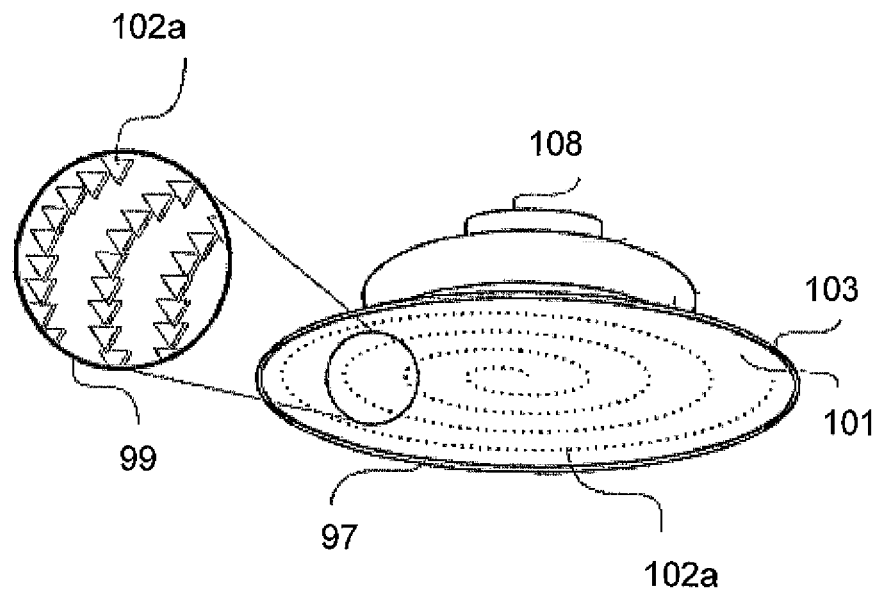
FIG. 17A-M. Perspective views of various embodiments of physiological recording devices with varying configurations of surface features individually and in combination with each other, such embodiments including (A) a device with a flat lower surface with penetrators in a spiral pattern; (B) a device with a flat lower surface with ridges in a circular pattern; (C) a device with a flat lower surface with ridges in a linear pattern; (D) a device with a flat lower surface with ridges in a linear and perpendicular pattern; (E) a device with a flat lower surface with ridges in a non-continuous circular pattern; (F) a device with a flat lower surface with four regions, one of each region containing a different surface feature style including penetrators, ridges, double penetrators, and a combination of ridges, penetrators and epidermal stops; (G) a device with a flat lower surface with penetrators arranged in clusters; (H) a device with a flat lower surface with columns arranged in interlocking L-shapes; (I) a device with a flat lower surface with columns comprising a concave end with micropenetrators; (J) a device with a flat lower surface with clustered columns; (K) a device with a flat lower surface with ridges formed into separate rings; (L) a device with a flat lower surface with ridges arranged in non-concentric rings; and (M) a device with a flat lower surface with columns with pyramidal tips.

FIGS. 17A through 17M illustrate still further configurations of surface features and lower surfaces that may be comprised with the present invention in various combinations. FIG. 17A is an isometric view of another embodiment of a physiological recording device. The device comprises an upper 103 and a lower 101 surface, and a connector 108. The device has on its flat lower surface 101 surface features arranged in a spiral arrangement or pattern 97 in the form of penetrators 102a. The details of the penetrators 102a are better viewed in the call out 99, which shows pyramidal shaped penetrators 102a.

Figure 17B:
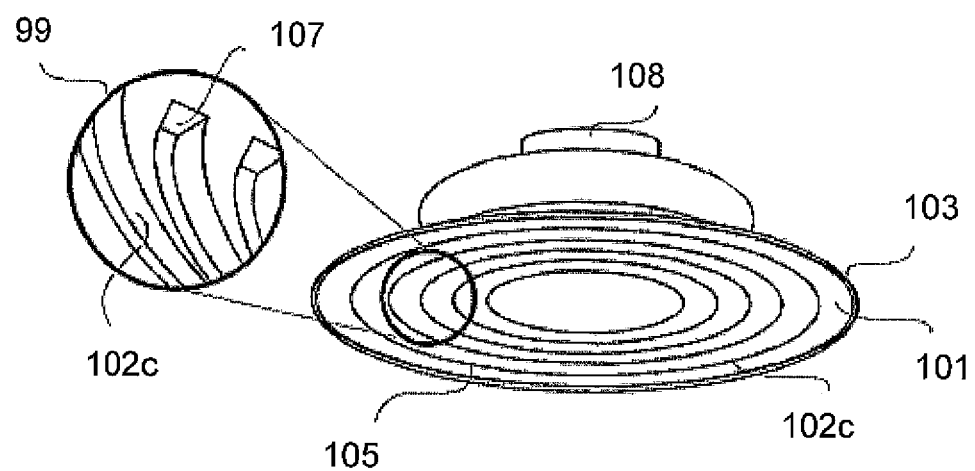

FIG. 17B is an isometric view of another embodiment of a physiological recording device. The device comprises an upper 103 and a lower 101 surface, and a connector 108. The device has on its flat lower surface 101 surface features arranged in concentric rings or a circular arrangement or pattern 105 and in the form of ridges 102c. The details of the ridges 102c are better viewed in the call out 99, which shows a ridge 102c with a trapezoidal cross section 107 over a length of a ridge 102c. The circular arrangement or pattern 105 of ridges 102c enhance the electrode-skin interface, and improve subject comfort by creating space for hair, detritus, air, and/or moisture to flow or collect.

Figure 17C:
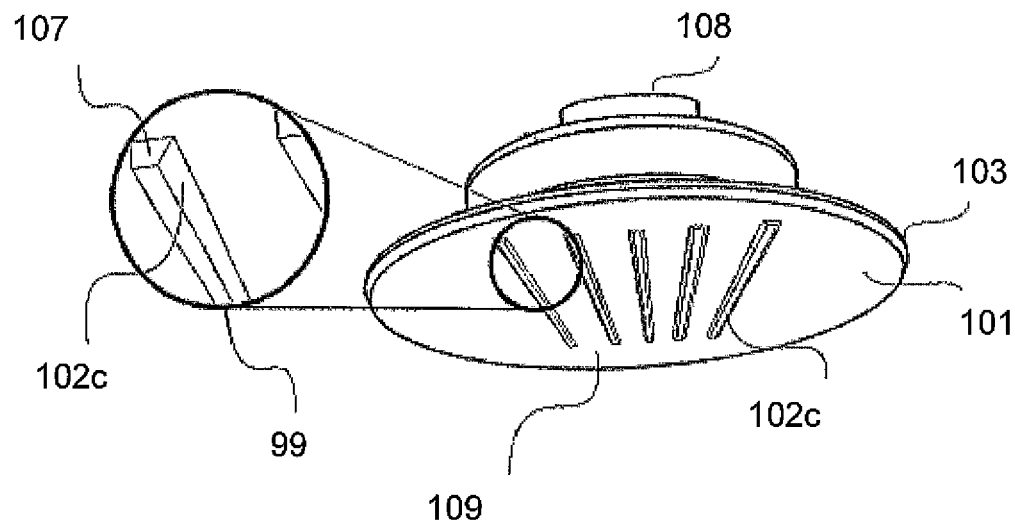

FIG. 17C is an isometric view of another embodiment of a physiological recording device. The device comprises an upper 103 and a lower 101 surface, and a connector 108. The device has on its flat lower surface 101 five straight ridges 102c extending over a length. The details of the ridges 102c are better viewed in the call out 99, which shows a ridge 102c with a trapezoidal cross section 107 over a length of a ridge 102c. The linear spacing of the ridges 102c also enhances the electrode-skin interface, and improves subject comfort by creating space or detritus trough 109 for hair, detritus, air, and/or moisture to flow or collect.

Figure 17D:
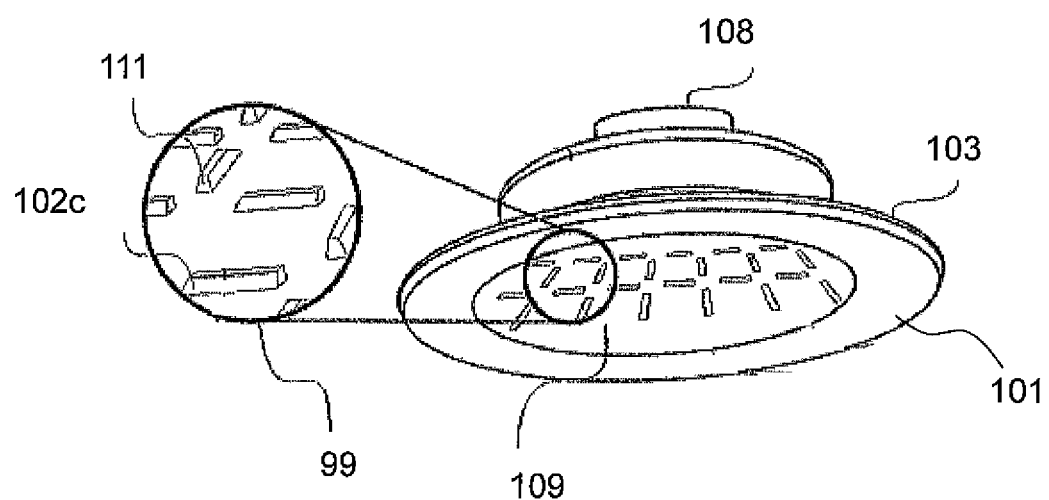

FIG. 17D is an isometric view of another embodiment of a physiological recording device. The device comprises an upper 103 and a lower 101 surface, and a connector 108. The device has on its flat lower surface 101 twelve groupings of a first ridge 102c perpendicularly positioned with respect to a second ridge 102c. The details of the ridges 102c are better viewed in the call out 99, which shows ridges 102c with trapezoidal cross sections 107 over a length of a ridge 102c. The linear and perpendicular spacing/placement of the ridges 102c also enhances the electrode-skin interface, and improves subject comfort by creating space or detritus trough 109 for hair, detritus, air, and/or moisture to flow or collect.

Figure 17E:
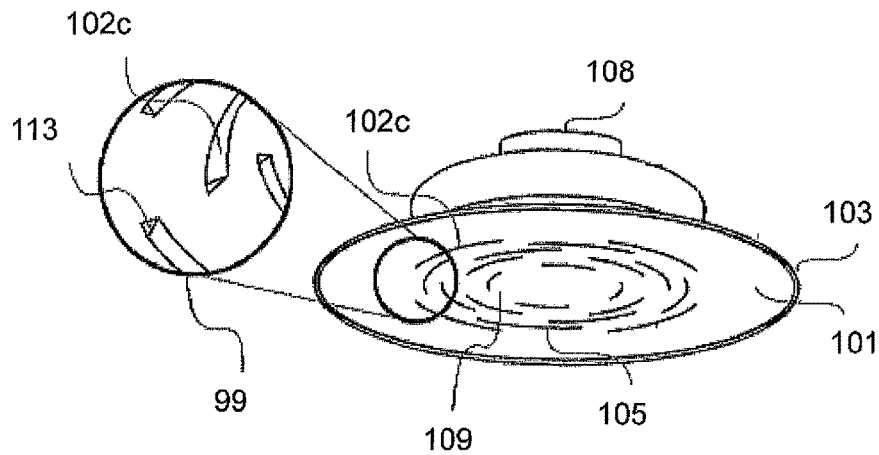

FIG. 17E is an isometric view of another embodiment of a physiological recording device. The device comprises an upper 103 and a lower 101 surface, and a connector 108. The device has on its flat lower surface 101 non-continuous concentric rings or a circular arrangement or pattern 105 of ridges 102c. The details of the ridges 102c are better viewed in the call out 99, which shows a ridge 102c with a triangular cross section 113 over a length of a ridge 102c. The non-continuous concentric arrangement of rings 105 enhances the electrode-skin interface, and improves subject comfort by creating space or a detritus trough 109 for hair, detritus, air, and/or moisture to flow or collect.

Figure 17F:
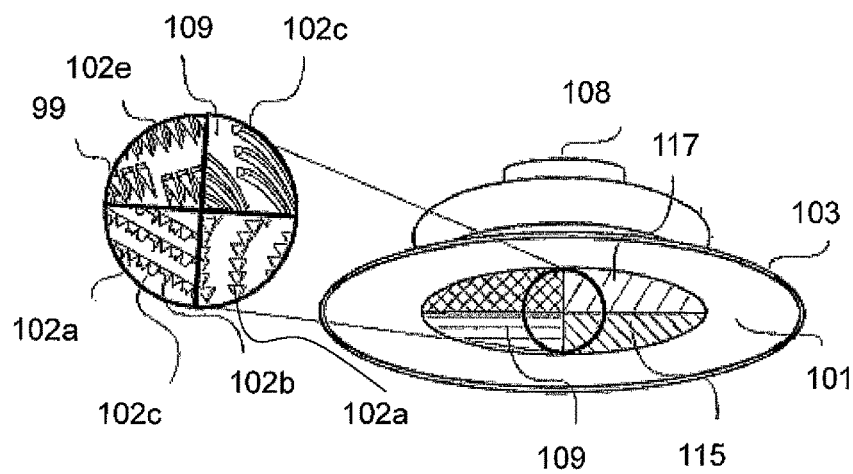

FIG. 17F is an isometric view of another embodiment of a physiological recording device. The device comprises an upper 103 and a lower 101 surface, and a connector 108. The device has four varying topographic regions or multiple surface structures 115 on its lower surface 101. The call out 99 of the multiple surface structure regions 115 shows pyramidal penetrators 102a in one region, ridges 102c in another region, thatch-like or double penetrators 102e in another region, and a combination of ridges 102c, penetrators 102a and epidermal stops 102b in another region in quadrants 117 on the device's flat lower surface 101. The arrangement of varying surface features enhance the electrode-skin interface, lowers the impedance and improve the subject's comfort by creating space or a detritus trough 109 for hair, detritus, air, and/or moisture to flow or collect.

Figure 17G:
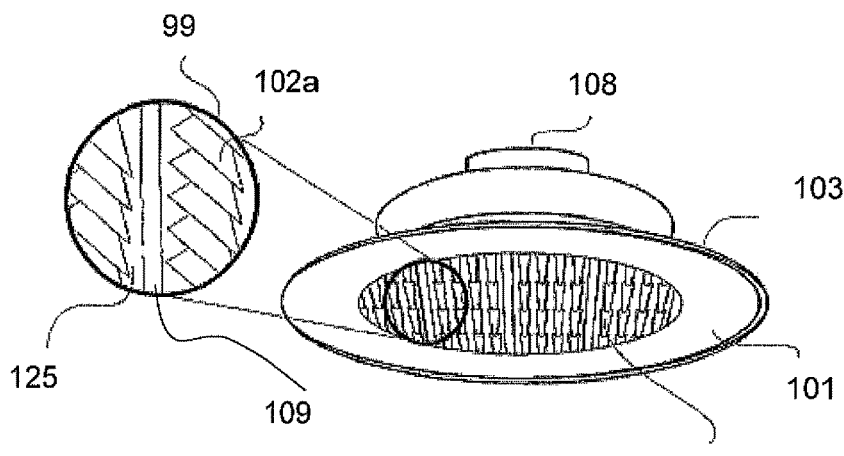

FIG. 17G is an isometric view of another embodiment of a physiological recording device. The device comprises an upper 103 and a lower 101 surface, and connector 108. The device as shown in the callout 99 comprises penetrators 102a that are pyramidal in shape on its flat lower surface 101 arranged in clusters with channels 125 on the device's lower surface 101. The arrangement of clustered penetrators 102a enhances the electrode-skin interface, and improves subject comfort by creating space or a detritus trough 109 for hair, detritus, air, and/or moisture to flow or collect.

Figure 17H:
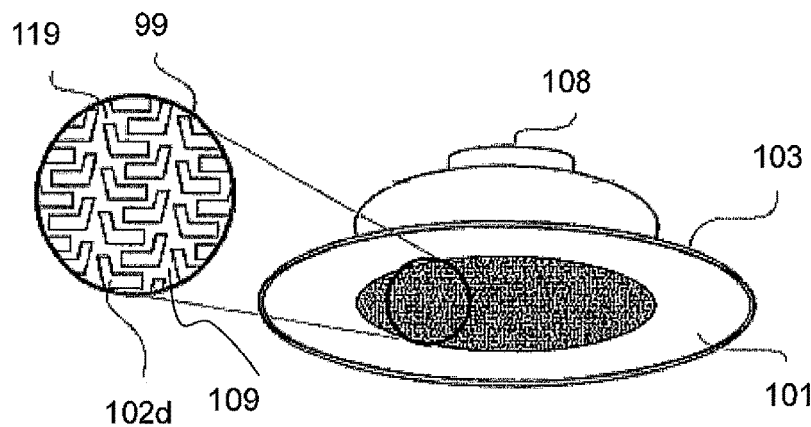

FIG. 17H is an isometric view of another embodiment of a physiological recording device. The device comprises an upper 103 and a lower 101 surface, and a connector 108. The device has various raised surface features 119 on the lower surface 101 in an almost L-shape. The call out 99 shows in greater detail that these raised surface features 119 are interlocking columns 102d. The arrangement of interlocking 119 columns 102d enhances the electrode-skin interface, and improves subject comfort by creating space or detritus troughs 109 for hair, detritus, air, and/or moisture to flow or collect.

Figure 17I:
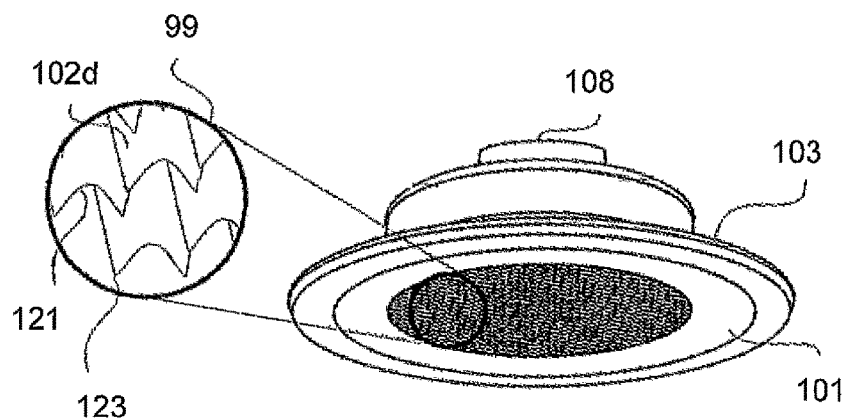

FIG. 17I is an isometric view of another embodiment of a physiological recording device. The device comprises an upper 103 and a lower 101 surface, and connector 108. The device has a large number of columns 102d on the lower surface 101. In the call out 99, the columns 102d are shown in greater detail to have a concave or cup end 121 with two micropenetrators 123. The arrangement of cup-ended columns 102d enhances the electrode-skin interface, and improves subject comfort by creating space or a detritus trough (not shown) for hair, detritus, air, and/or moisture to flow or collect.

Figure 17J:
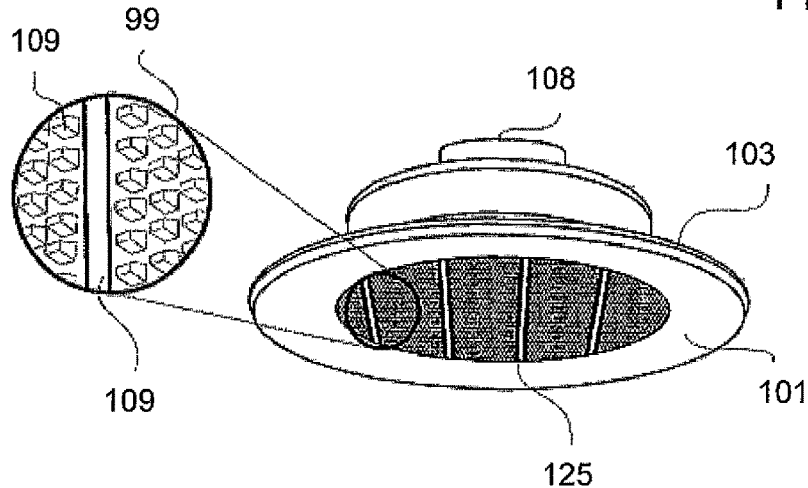

FIG. 17J is an isometric view of another embodiment of a physiological recording device. The device comprises an upper 103 and a lower 101 surface, and a connector 108. The device is depicted to have trapezoidal columns 109 on its flat lower surface 101 arranged in clusters with channels 125. The arrangement of clustered columns 109 enhance the electrode-skin interface, and improve subject comfort by creating space or a detritus trough 109 for hair, detritus, air, and/or moisture to flow or collect.

Figure 17K:
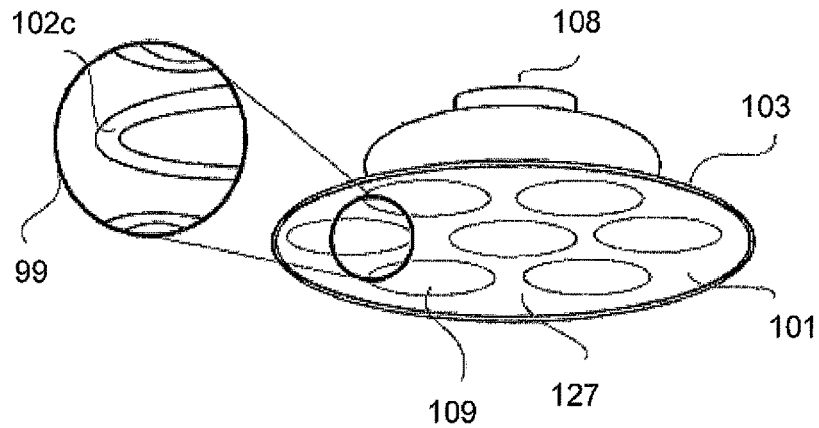

FIG. 17K is an isometric view of another embodiment of a physiological recording device. The device comprises an upper 103 and a lower 101 surface, and a connector 108. The device as shown in the cutout 30 with ridges 102c on its flat lower surface 101 arranged in a pattern of seven small rings 127. The arrangement of seven small rings 127 enhances the electrode-skin interface, and improves subject comfort by creating space or a detritus trough 109 for hair, detritus, air, and/or moisture to flow or collect.

Figure 17L:
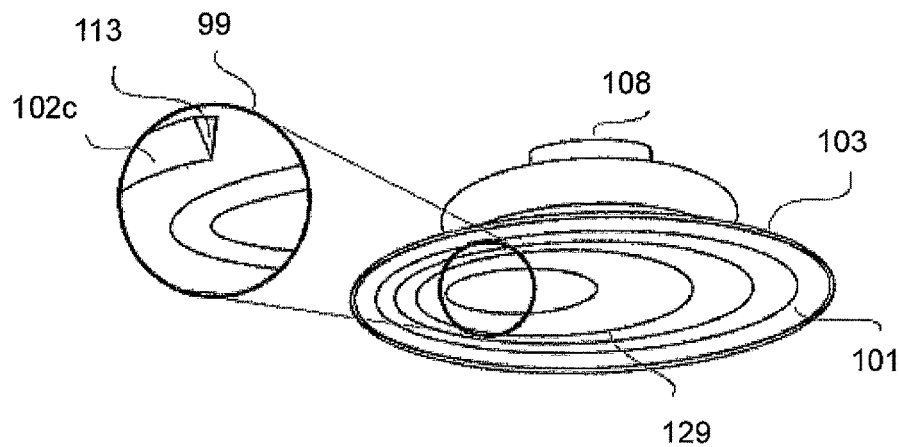

FIG. 17L is an isometric view of another embodiment of a physiological recording device. The device comprises an upper 103 and a lower 101 surface, and a connector 108. The device as shown in the call out 99 with ridges 102c with triangular cross section 113 on its flat lower surface 101 arranged in non-concentric rings 129. The arrangement of non-concentric rings 129 shown better in the call out 99 enhances the electrode-skin interface, and improves subject comfort by creating space or a detritus trough (not shown) for hair, detritus, air, and/or moisture to flow or collect.

Figure 17M:
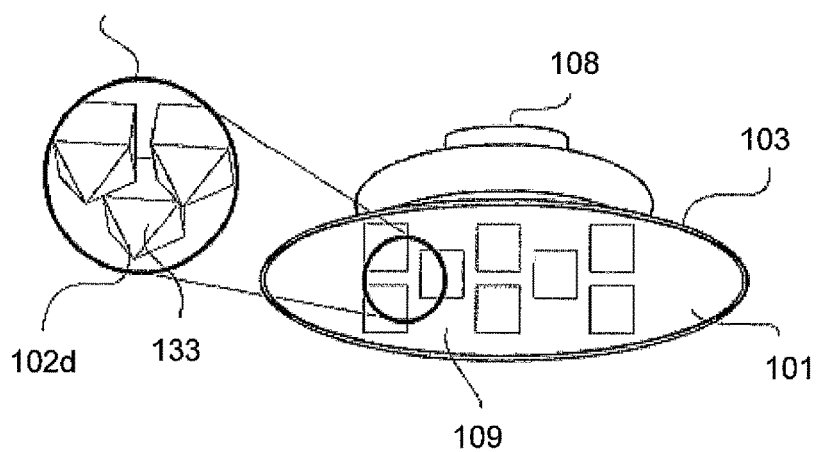

FIG. 17M is an isometric view of another embodiment of a physiological recording device. The device comprises an upper 103 and a lower 101 surface, and a connector 108. The device is shown in the call out 99 with columns 102d with pyramidal caps 133 on its flat lower surface 101. The arrangement of pyramidal columns 102d, 133 shown better in the call out 99 enhances the electrode-skin interface, and improves subject comfort by creating space or a detritus trough 109 for hair, detritus, air, and/or moisture to flow or collect. These columns 102d do not penetrate the skin, like a pyramidal penetrator, but rather merely depress the skin to anchor the electrode.

Figure 18A:
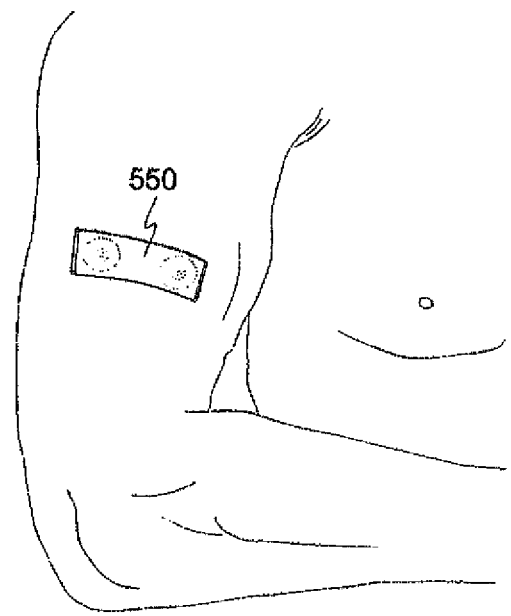
FIG. 18A-C. Pictures depicting various embodiments of physiological recording devices attached to a garment, specifically an arm band for the subject to wear about the arm to record physiological signals, such embodiments including (A) an adhesive garment; (B) a harness; and (C) a band.
Figure 18B:
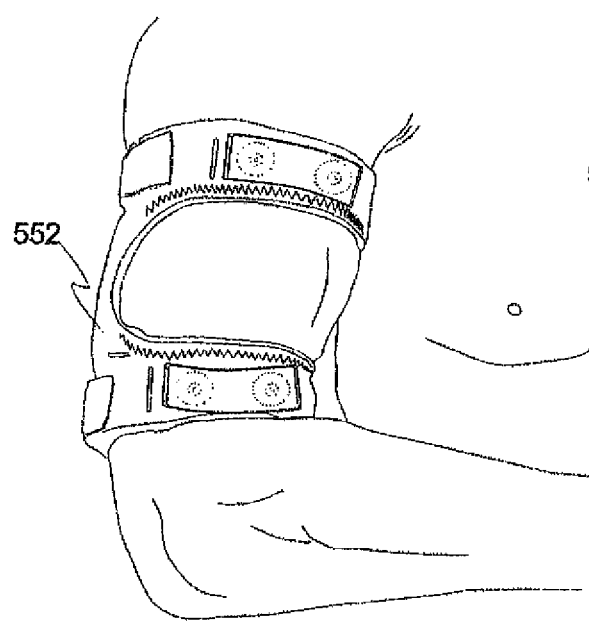
Figure 18C:
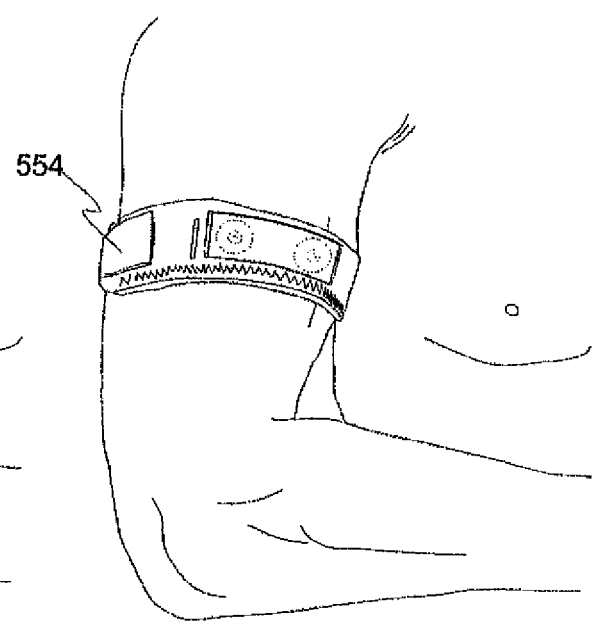

FIG. 18 illustrates various embodiments of the present invention wherein the dry physiological recording device is attached to or embedded into a wearable such as a garment, harness, or other means of attaching the device to a subject's skin. Such embodiments may utilize a rivet connector, such as depicted in FIGS. 12A through 12D, or may use standard snap connectors. However, it is intended that the devices be able to be attached to such garments, harnesses, or other wearable equipment by any means currently known to those of skill in the art, or later developed. The physiological recording devices may be attached or embedded to the wearable in a stationary manner, or in an adjustable manner, such as in a track or path along which the devices may be moved once attached to the wearable. The physiological recording devices can be packaged by conventional packaging techniques, either individually or in groups of more than one device. Preferably the packaging provides at least 1) adequate structural support for the device so it can be handled roughly (i.e., dropped, crushed, etc.) without damage; 2) a means (i.e., a spring, or the like) to force the device against the subject's skin with a consistent pressure; 3) a low impedance path 33 from the device's surface to the package's output connector 34; and 4) a design which allows for easy cleaning and sterilization for applications requiring reuse. These devices can thus be packaged together or individually, and individual devices or packages of devices can be mounted to the skin using conventional techniques such as adhesives 550, harnesses 552 or bands 554. Other wearables may be utilized as well, such as attaching or integrating the devices into typical clothing such as clothing, footwear, and the like (not shown).

FIG. 19 depicts a top view (19A) and a cross-section (19B) of another embodiment of a physiological recording device wherein the device is a single piece of stamped metal. The stamped metal device 455 in the present embodiment is manufactured via a stamping process as described herein, but further comprises an integrated connector 180 that is formed as part of the device 455 during the stamping process. The process of manufacturing the device 455 via stamping, as disclosed herein, involves pressing a negative mold of the desired device shape into a piece of metal, and thus forming in said metal the desired shape. In this particular embodiment, the mold used for shaping the device 455 would be partially a negative image and partially a positive image, such that the negative image would allow the surface features 102 and lower surface 101 to be formed, while the positive image presses into the metal and forms the connector 180 rising from the upper surface 103. It can be envisioned where the stamping mold may be reversed and the negative and positive images form the opposite portion of the device, or where two separate molds are used to press the piece of metal between them and form the shape of the device as desired.

Figure 19A:
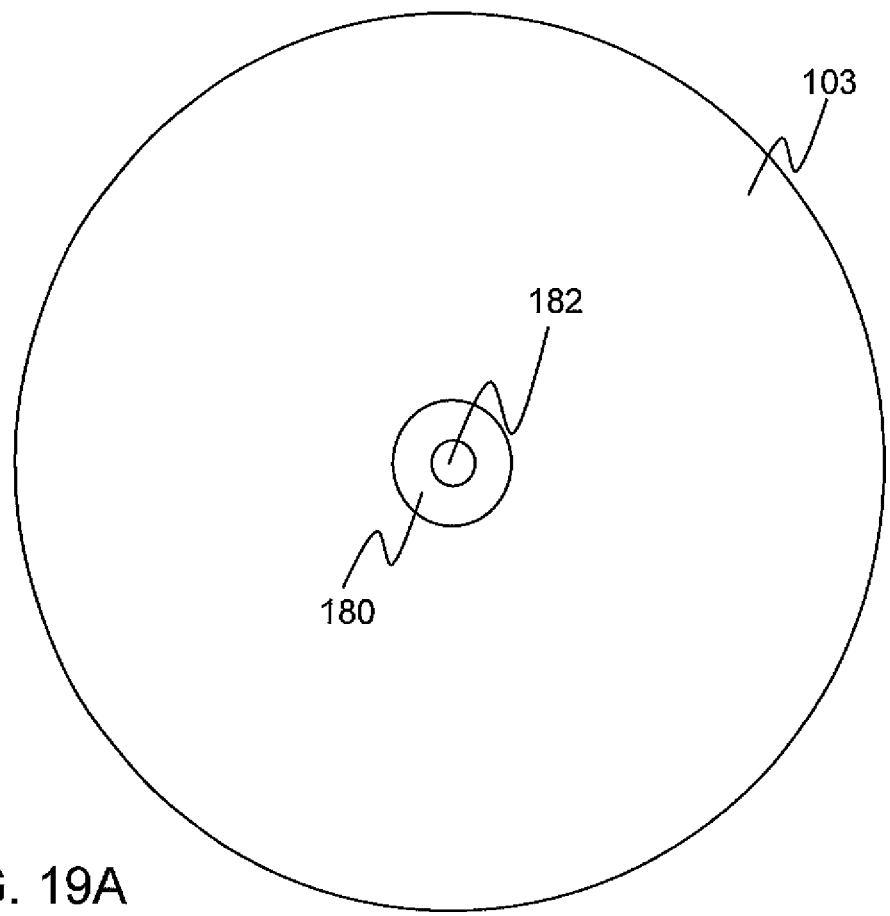
FIG. 19A-B. Depiction of a (A) top and (B) cross-section view of various embodiments of a stamped metal physiological recording device where the entire device is manufactured via a stamping process, including the integrated connector.

FIG. 19A depicts a top view of the device 455 such that the upper surface 103 is shown with a connector 180 in the center of said upper surface 103. This top view further depicts an optional feature of this particular stamped metal embodiment of the device 455 wherein the stamping process leaves an opening, aperture or hole 182 in the top of the connector 180. This opening, aperture or hole may be formed by using a stamping mold with an extended portion used to corm the connector 180 whereby the extended portion actually punches through the piece of metal during stamping. The opening, aperture or hole 182 may serve several purposes. First, the opening, aperture or hole 182 allows for less metal to be used in the manufacturing of each device and thus reduces costs of manufacture. Second, the opening, aperture or hole allows a portion of the metal that would otherwise be stretched to form a complete, whole connector 180 to remain in the sides and stem of the connector 180, and thus ensure that the connector 180 is a stronger and more resilient. This added material and strength in the sides and step of the connector makes the device more stable when attached to the subject and/or a wearable or other garment, and increases the usable life of the device.

Figure 19B:
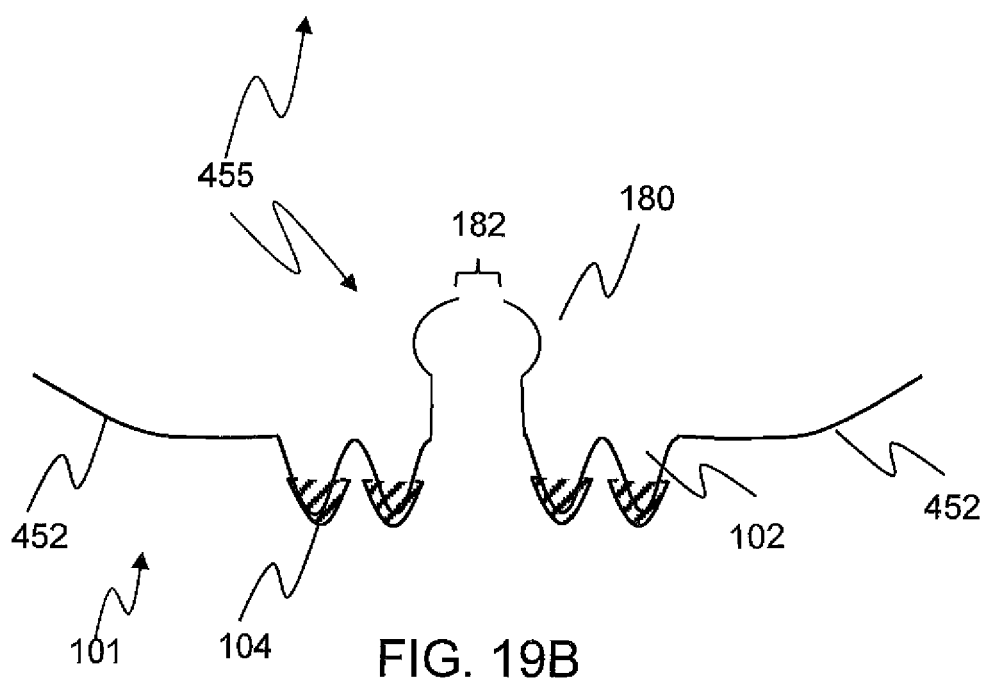

FIG. 19B depicts a cross section of the stamped metal device 455 embodiment with an integrated connector 180. The lower surface 101 of the device 455 comprises surface features 102 as described throughout, but lacks a center surface feature due to the nature of the stamping process used to form the device including the integrated connector 180. AS the connector 180 is formed, it creates a depression or gap in the lower surface 101 corresponding to the pressing of the metal piece up to form the connector as part of the upper surface 103. Both the lower surface 101 and the upper surface 103 are depicted as having the characteristic curvature of an encouragement lip, though it is possible in some embodiments for only the lower surface to have the curvature of the encouragement lip 452. The connector 180 again shows the optional opening, aperture or hole 182 in the top of the connector 180. The single piece construction of the device requires minimal materials to manufacture the device 455 and thus minimizes the costs of production. The device 455 being made of metal allows for the entire body of the device to be a good conductor and to facilitate the transmission of biopotential signals from the subject's body to the monitoring equipment. As discussed throughout, the surface features 102 create a stronger connection with the subject's body fluids, and the conductive coating and/or ionic compound 104 may be used to coat all, or more preferably, just a portion of the surface features 102 to facilitate the required redox reaction to drive the transmission of the biopotential signals. The conductive metal body with a minimal amount of material, along with the minimal amount of conductive coating and/or ionic compound 104 required to create the required reaction, allows the device's cost to be minimized on multiple levels.

FIG. 20 is an illustration of (A) an independent, separate encouragement ring portion of a physiological recording device with an interior lip or edge, (B) a side view of an independent, separate encouragement ring portion with an interior lip or edge, (C) a side view of a separate dry recording portion comprising an external lip or edge with channels or depressions, and (D) a bottom view of the lower surface of a separate dry recording portion with channels or depressions. In the depicted embodiment(s), the separate recording portion 160 fits into the opening or void 153 of the separate encouragement ring portion 150 by inserting the separate recording portion into the opening or void of the separate encouragement ring portion. In one preferred embodiment where the recording portion 160, and thus the opening or void 153 in the encouragement ring portion 150 are circular in shape, preferably the radius of the recording portion and the radius of the opening or void 153 in the encouragement ring portion 150 are substantially similar, with the radius of the recording portion being marginally smaller than that of the opening or void in the encouragement ring portion. This allows the recording portion to fit inside of the opening or void in the encouragement ring portion securely, and when a conductive coating or ionic compound is applied to the recording portion, the gap between the two is filled providing an even more secure sit. The lip or edge 210, 215 of each separate portion compliments each other's shape and thus prevent the separate recording portion 160 from pushing entirely through the separate encouragement ring portion 150. This mechanism allows for the separate recording portion to receive a conductive coating and/or ionic compound (not shown) while the separate encouragement ring portion 150 does not, and when the two are assembled for the resultant assembled device (not shown) to be solid and stable for placement onto the subject's skin.

FIG. 20A depicts a top view of the upper surface 103 of the separate encouragement ring portion 150. The encouragement ring portion 150 has an opening or void 153 in the center into which a separate recording portion 160 (FIGS. 20C and 20D) can be inserted to form a physiological recording device. The inner edge of the separate encouragement ring portion forms a lip or edge 210 which matches with a lip or edge on the separate recording portion when the separate pieces are joined together. The separate recording portion may be inserted into the opening or void 153 of the encouragement ring portion 150 such that the lower surface of the two separate portions are aligned, as are the upper surfaces 103. FIG. 20B depicts a side view of the separate encouragement ring portion 150. The dashed lines represent the inner edge of the encouragement ring portion surrounding or creating the opening or void 153 through the center of the encouragement ring. Said inner edge is shown to have a step approximately half way through the thickness of the encouragement ring thus creating the edge or lip 210 which serves to create a stopping point for the separate recording portion 160 when inserted into the encouragement ring portion 150. Though the edges or lips 210, 215 of each portion are shown in such a manner that the recording portion 160 would inserted into the opening or void 153 via the upper surface of the encouragement ring portion 150, it may be envisioned that the lips or edges 210, 215 could be reversed such that the recording portion 160 would be inserted into the opening or void 153 via the lower surface of the encouragement ring portion. Preferably, the separate encouragement ring portion 150 receives no conductive coating and/or ionic compound. Thus, the overall cost of the device may be reduced by making this encouragement ring portion from a sturdy yet less expensive material, and by not placing the expensive conductive coating and/or ionic compound on this portion.

FIG. 20C depicts a side view of the separate recording portion 160 comprising surface features 102 on the lower surface 101, a connector 108 on the upper surface 103, and channels or depressions 212 in the outer edge, and FIG. 20D depicts a bottom view of the recording portion showing the lower surface 101 of the recording portion and a plurality of surface features 102. The surface features 102 may be of any type described herein, as may be the connector. Though the connector 108 shown is a standard snap connector, any type of connector may be constructed as part of the device, or attached as a separate piece. In many embodiments, the separate recording portion 160 may receive a conductive coating and/or ionic compound (not shown). However, by the nature of assembling the separate, coated recording portion with the separate encouragement ring portion, the conductive coating and/or ionic compound may be scraped away from the outer edge of the recording portion 160 when rubbed or scraped against the inner edge of the encouragement ring portion while placing the recording portion into the opening or void 153 of the encouragement ring portion. Therefore, the recording portion 160 in such embodiments preferably has channels or depressions in its outer edge that provide a recessed pathway for the conductive coating and/or ionic compound without being scraped away when the two separate pieces are assembled together. Therefore, when the recording portion is placed into the encouragement ring portion, the two pieces preferably fit together securely and snugly such that the recording portion cannot simply slide out from the assembled position, but rather direct, purposeful force should be required to separate the assembled device. The channels or depressions allow the conductive coating and/or ionic compound to maintain a continuous pathway from the lower surface 101 of the recording portion 160 to the upper surface 103. Thus, the conductive coating and/or ionic compound is placed on the lower surface 101, or a portion thereof, of the recording portion 160, and at least on some portion of the rest of the recording portion, preferably through at least one channel or depression, such that the conductive coating and/or ionic compound travels from the lower surface to the upper surface 103 and to the connector 108 creating a continuous pathway such that the coating or compound may facilitate the required redox reaction and transmit biopotential signals from the subject to the connector and to the monitoring equipment (not shown). This embodiment allows the device cost to be minimized be decreasing the amount of expensive materials, including the conductive coating or ionic compound required, and allowing the separate encouragement ring portion to be manufactured from an inexpensive material. Some embodiments may further decrease the cost of the device by only placing the conductive coating and/or ionic compound on the surface features 102, or a portion thereof, and using a less expensive metallic or conductive coating to create an electrical pathway around the rest of the recording portion. In such embodiments, the more expensive conductive coating and/or ionic compound (such as Ag/AgCl) connects the device to the subject's skin and facilitates the required redox reaction, and the biopotential signals are transmitted from the subject, through the conductive coating and/or ionic compound into the less expensive metallic or conductive coating, and through said less expensive metallic or conductive coating (through the channels or depressions) to the connector 108 and then to the monitoring equipment (not shown).

It will be apparent to those skilled in the art that various modifications and variations can be made to the present invention without departing from the spirit and scope of the invention. Thus, it is intended that the present invention cover the various modifications and variations of this invention provided they come within the scope of the appended claims and their equivalents.

The invention claimed is:

1. A physiological recording device comprising:
   a garment, harness, or wearable adapted to be worn or attached to the subject and comprising at least one electrode connector; and
   at least one electrode having a radius and comprising an upper surface and a lower surface, the lower surface comprising at least one surface feature adapted to not penetrate the subject's skin, the at least one surface feature further adapted to in part transmit at least one physiological signal from the lower layers of a subject's skin, the upper surface comprising a connector adapted to connect the electrode to the at last one electrode connector of the garment, harness, or wearable, the at least one electrode further comprising an encouragement lip extending radially outward and curving away from the lower surface and from the subject's skin when attached thereto, the encouragement lip adapted to anchor the electrode of the physiological recording device to the subject's skin, wherein the encouragement lip has a radius of curvature over substantially all of a distance of curvature greater than 1.0 cm.

2. The physiological recording device of claim 1, wherein the at least one electrode is a monolithic polymer or plastic electrode.

3. The physiological recording device of claim 1, comprising at least three electrodes connected to at least three electrode connectors comprised on the garment, harness, or wearable, at least one of the at least three electrodes being a monolithic polymer or plastic electrode and at least one electrode being removably connected to the garment, harness, or wearable.

4. The physiological recording device of claim 3, wherein at least one of the at least three electrodes comprises a plurality of surface features arranged in a circular pattern.

5. The physiological recording device of claim 4, wherein the physiological recording device is specifically adapted to acquire electrocardiogram (ECG) signals from at least one subject.

6. The physiological recording device of claim 5, wherein at least a portion of the lower surface and the at least one surface feature of each electrode are coated with a conductive coating and/or ionic compound.

7. The physiological recording device of claim 6, wherein the lower surface comprises a plurality of surface features adapted to not penetrate the subject's skin, and fewer than all of the plurality of such surface features are at least partially coated with a conductive coating and/or ionic compound.

8. A physiological recording device comprising:
a garment, harness, or wearable adapted to be worn or attached to the subject and comprising at least one electrode connector; and
at least one electrode having a radius and comprising an upper surface and a lower surface, the lower surface comprising at least one surface feature adapted to not penetrate the subject's skin, the at least one surface feature further adapted to in part transmit at least one physiological signal from the lower layers of a subject's skin, the upper surface comprising a connector adapted to connect the electrode to the at last one electrode connector of the garment, harness, or wearable, the at least one electrode further comprising an encouragement lip extending radially outward and curving away from the lower surface and from the subject's skin when attached thereto, the encouragement lip adapted to anchor the electrode of the physiological recording device to the subject's skin,
wherein the physiological recording device is specifically adapted to acquire electrocardiogram (ECG) signals from at least one subject, and the encouragement lip has a radius of curvature over substantially all of a distance of curvature greater than 1.0 cm.

9. The physiological recording device of claim 8, wherein the at least one electrode is a monolithic polymer or plastic electrode.

10. The physiological recording device of claim 8, comprising at least three electrodes connected to at least three electrode connectors comprised on the garment, harness, or wearable, at least one of the at least three electrodes being a monolithic polymer or plastic electrode and at least one electrode being removably connected to the garment, harness, or wearable.

11. The physiological recording electrode of claim 10, wherein at least one of the at least three electrodes comprises a plurality of surface features arranged in a circular pattern.

12. The physiological recording device of claim 11, wherein the physiological recording device is specifically adapted to acquire electrocardiogram (ECG) signals from at least one subject.

13. The physiological recording device of claim 12, wherein at least a portion of the lower surface and the at least one surface feature of each electrode are coated with a conductive coating and/or ionic compound.

14. The physiological recording device of claim 13, wherein the lower surface comprises a plurality of surface features adapted to not penetrate the subject's skin, and fewer than all of the plurality of such surface features are at least partially coated with a conductive coating and/or ionic compound.

15. A physiological recording device comprising:
a garment, harness, or wearable adapted to be worn or attached to the subject and comprising at least one electrode connector; and
at least one monolithic polymer or plastic electrode having a radius and comprising an upper surface and a lower surface, the lower surface comprising at least one surface feature adapted to not penetrate the subject's skin, the at least one surface feature further adapted to in part transmit at least one physiological signal from the lower layers of a subject's skin, the upper surface comprising a connector adapted to connect the electrode to the at last one electrode connector of the garment, harness, or wearable, the at least one electrode further comprising an encouragement lip extending radially outward and curving away from the lower surface and from the subject's skin when attached thereto, the encouragement lip adapted to anchor the electrode of the physiological recording device to the subject's skin,
wherein the encouragement lip has a radius of curvature over substantially all of a distance of curvature greater than 1.0 cm.

16. The physiological recording device of claim 15, comprising at least three electrodes connected to at least three electrode connectors comprised on the garment, harness, or wearable, at least one electrode being removably connected to the garment, harness, or wearable.

17. The physiological recording device of claim 16, wherein at least one of the at least three electrodes comprises a plurality of surface features arranged in a circular pattern.

18. The physiological recording device of claim 17, wherein the physiological recording device is specifically adapted to acquire electrocardiogram (ECG) signals from at least one subject.

19. The physiological recording device of claim 18, wherein at least a portion of the lower surface and the at least one surface feature of each electrode are coated with a conductive coating and/or ionic compound.

20. The physiological recording device of claim 19, wherein the lower surface comprises a plurality of surface features adapted to not penetrate the subject's skin, and fewer than all of the plurality of such surface features are at least partially coated with a conductive coating and/or ionic compound.

\* \* \* \* \*